(12) United States Patent
Shibayama et al.

(10) Patent No.: US 12,091,461 B2
(45) Date of Patent: *Sep. 17, 2024

(54) BISPECIFIC ANTIBODY

(71) Applicant: ONO PHARMACEUTICAL CO., LTD., Osaka (JP)

(72) Inventors: Shiro Shibayama, Ibaraki (JP); Takuya Shimbo, Ibaraki (JP); Tomoya Tezuka, Ibaraki (JP); Mark Throsby, Utrecht (NL); Cornelis Adriaan de Kruif, Utrecht (NL); Pieter Fokko van Loo, Utrecht (NL); Rinse Klooster, Utrecht (NL)

(73) Assignee: ONO PHARMACEUTICAL CO., LTD., Osaka (JP)

( * ) Notice: Subject to any disclaimer, the term of this patent is extended or adjusted under 35 U.S.C. 154(b) by 306 days.

This patent is subject to a terminal disclaimer.

(21) Appl. No.: 17/366,878

(22) Filed: Jul. 2, 2021

(65) Prior Publication Data

US 2021/0332134 A1     Oct. 28, 2021

Related U.S. Application Data

(63) Continuation of application No. 16/967,668, filed as application No. PCT/JP2019/004551 on Feb. 8, 2019, now Pat. No. 11,091,550.

(30) Foreign Application Priority Data

Feb. 9, 2018 (JP) .................. 2018-021498
Aug. 16, 2018 (JP) .................. 2018-153149

(51) Int. Cl.
| C07K 16/28 | (2006.01) |
|---|---|
| A61K 45/06 | (2006.01) |
| A61P 37/02 | (2006.01) |
| C07K 16/46 | (2006.01) |
| A61K 39/00 | (2006.01) |

(52) U.S. Cl.
CPC .......... C07K 16/2818 (2013.01); A61K 45/06 (2013.01); A61P 37/02 (2018.01); C07K 16/468 (2013.01); A61K 2039/505 (2013.01)

(58) Field of Classification Search
None
See application file for complete search history.

(56) References Cited

U.S. PATENT DOCUMENTS

| 5,585,097 A | 12/1996 | Bolt et al. |
|---|---|---|
| 5,834,597 A | 11/1998 | Tso et al. |
| 5,932,449 A | 8/1999 | Emanuel et al. |
| 6,111,079 A | 8/2000 | Wylie et al. |
| 6,808,710 B1 | 10/2004 | Wood et al. |
| 7,029,674 B2 | 4/2006 | Carreno et al. |
| 7,563,869 B2 | 7/2009 | Honjo et al. |
| 7,883,703 B2 | 2/2011 | Weiner et al. |
| 7,998,479 B2 | 8/2011 | Honjo et al. |
| 8,008,449 B2 | 8/2011 | Korman et al. |
| 8,246,955 B2 | 8/2012 | Honjo et al. |
| 8,481,022 B2 | 7/2013 | Lodie et al. |
| 8,951,518 B2 | 2/2015 | Honjo et al. |
| 9,701,749 B2 | 7/2017 | Shibayama et al. |
| 9,783,609 B2 | 10/2017 | Honjo et al. |
| 10,266,593 B2 | 4/2019 | Bakker et al. |
| 10,647,770 B2 | 5/2020 | Shibayama et al. |
| 11,091,550 B2 * | 8/2021 | Shibayama ........ C07K 16/2818 |
| 2002/0160000 A1 | 10/2002 | Wood et al. |
| 2004/0241745 A1 | 12/2004 | Honjo et al. |
| 2005/0004352 A1 | 1/2005 | Kontermann et al. |
| 2006/0210567 A1 | 9/2006 | Collins et al. |
| 2007/0092504 A1 | 4/2007 | Carreno |
| 2007/0202100 A1 | 8/2007 | Wood et al. |
| 2008/0025979 A1 | 1/2008 | Honjo et al. |
| 2009/0076250 A1 | 3/2009 | Honjo et al. |
| 2009/0217401 A1 | 8/2009 | Korman et al. |
| 2009/0263865 A1 | 10/2009 | Honjo et al. |
| 2009/0324609 A1 | 12/2009 | Lodie et al. |
| 2011/0104148 A1 | 5/2011 | Mössner et al. |
| 2011/0171215 A1 | 7/2011 | Davis et al. |
| 2011/0229461 A1 | 9/2011 | Tyson |
| 2011/0280878 A1 | 11/2011 | Honjo et al. |
| 2012/0003210 A1 | 1/2012 | Farrington et al. |

(Continued)

FOREIGN PATENT DOCUMENTS

| CN | 114174343 A | 3/2022 |
|---|---|---|
| EP | 1 334 659 A1 | 8/2003 |

(Continued)

OTHER PUBLICATIONS

Khan et al. Sci. Rep. (2017) 7, 45163; doi: 10.1038/srep45163 (12 pages).*
Zhu et al. Cell (2015) 161: 1280-1292.*
Lee et al. Nature Medicine (2016) 22: 1456-1464.*
Abdiche et al. mAbs (2016) 8: 264-277.*
Konitzer et al. mAbs (2017) 9: 536-549.*
Ferrara et al. mAbs (2015) 7: 32-41.*
Parola et al. Immunology (2018) 153: 31-41.*

(Continued)

*Primary Examiner* — Ilia I Ouspenski
(74) *Attorney, Agent, or Firm* — Sughrue Mion, PLLC

(57) ABSTRACT

A bispecific antibody which is capable of specifically binding to PD-1 and CD3 is disclosed. The bispecific antibody is suitable for preventing, suppressing symptom progression or recurrence of, and/or treating autoimmune diseases. Also disclosed is a formulation which can reduce occurrence of adverse infusion reactions or adverse reaction called cytokine release syndrome. The bispecific antibody has the feature to allow interaction between PD-1 and PD-L1 as its ligand, contributes enhancement or duration of its effects.

36 Claims, 17 Drawing Sheets
Specification includes a Sequence Listing.

(56) References Cited

U.S. PATENT DOCUMENTS

| | | | |
|---|---|---|---|
| 2013/0022629 | A1 | 1/2013 | Sharpe et al. |
| 2013/0058936 | A1 | 3/2013 | Bruenker et al. |
| 2013/0164294 | A1 | 6/2013 | Honjo et al. |
| 2014/0120096 | A1 | 5/2014 | Bakker et al. |
| 2014/0220021 | A1 | 8/2014 | Shibayama et al. |
| 2015/0030622 | A1 | 1/2015 | Marshall et al. |
| 2015/0118234 | A1 | 4/2015 | Honjo et al. |
| 2015/0274845 | A1 | 10/2015 | Bruenker et al. |
| 2016/0075795 | A1 | 3/2016 | Mössner et al. |
| 2016/0368988 | A1 | 12/2016 | Bakker et al. |
| 2017/0320949 | A1 | 11/2017 | Shibayama et al. |
| 2018/0186875 | A1 | 7/2018 | Grogan et al. |
| 2018/0289802 | A1 | 10/2018 | Banks et al. |
| 2018/0355061 | A1 | 12/2018 | Chen et al. |
| 2019/0211100 | A1 | 7/2019 | Bakker et al. |
| 2020/0317783 | A1 | 10/2020 | Shibayama et al. |
| 2022/0281977 | A1 | 9/2022 | Shibayama et al. |

FOREIGN PATENT DOCUMENTS

| | | | |
|---|---|---|---|
| EP | 1 445 264 | A1 | 8/2004 |
| EP | 1 591 527 | A1 | 11/2005 |
| EP | 1 944 034 | A1 | 7/2008 |
| EP | 2 147 594 | A1 | 1/2010 |
| EP | 2 270 051 | A2 | 1/2011 |
| EP | 2 556 747 | A2 | 2/2013 |
| EP | 2 742 953 | A1 | 6/2014 |
| EP | 3 456 190 | A1 | 3/2019 |
| EP | 3 456 191 | A1 | 3/2019 |
| EP | 3 456 192 | A1 | 3/2019 |
| EP | 3 456 193 | A1 | 3/2019 |
| JP | 2000-201678 | A | 7/2000 |
| JP | 2010-229134 | A | 10/2010 |
| JP | 2011-525808 | A | 9/2011 |
| JP | 2015-532278 | A | 11/2015 |
| RU | 2 570 554 | C2 | 12/2015 |
| RU | 2 605 390 | C2 | 12/2016 |
| WO | 01/14557 | A1 | 3/2001 |
| WO | 01/64249 | A1 | 9/2001 |
| WO | 02/078731 | A1 | 10/2002 |
| WO | 03/011911 | A1 | 2/2003 |
| WO | 2004/072286 | A1 | 8/2004 |
| WO | 2009/157771 | A2 | 12/2009 |
| WO | 2013/003625 | A2 | 1/2013 |
| WO | 2013/022091 | A1 | 2/2013 |
| WO | 2017/010874 | A1 | 1/2017 |
| WO | 2019/009727 | A1 | 1/2019 |
| WO | 2019/070047 | A1 | 10/2020 |
| WO | 2020/204152 | A1 | 10/2020 |
| WO | 2021/006199 | A1 | 1/2021 |

OTHER PUBLICATIONS

Boyd et al. Current Opinion in Immunology 2016, 40: 103-109.*
Damschroder et al. Molecular Immunology (2004) 41: 985-1000.*
Van Regenmortel MHV. Front. Immunol. (2018) vol. 8, Article 2009 (11 pages).*
Kanyavuz et al. Nat Rev Immunol. 2019; 19(6): 355-368.*
Conroy et al. Methods (2017) 116: 12-22.*
Sheehan et al. Microbiol. Spectr. (2015) 3(1): AID-0028-2014; 17 pages.*
EP Communication dated Jun. 30, 2023 from the European Patent Office in EP Patent Application No. 20846826.4.
Xuan Gao et al., "Effect of Individual Fc Methionine Oxidation on FcRn Binding: Met252 Oxidation Impairs FcRn Binding More Profoundly than Met428 Oxidation" Journal of Pharmaceutical Sciences, Vo. 104, Issue 2, Feb. 2015, pp. 368-377 (also available at https://doi.org/10.1002/jps.24136, pp. 1-4).
Rebecca To,. et al., "Isolation of Monomeric Human VHS by a Phage Selection", Journal of Biological Chemistry, American Society for Biochemistry and Molecular Biology, US, vol. 280, No. 50, Dec. 16, 2005, pp. 41395-41403, DOI 10.1074/jbc.M5C9900200.

Simon Krah, et al., "Engineering IgG-Like Bispecific Antibodies—An Overview", Antibodies, vol. 7, No. 3, Aug. 1, 2018, pp. 1-10, doi:10.3390/antib7030028.
Christopher Paluch, et al., "Immune Checkpoints as Therapeutic Targets in Auto immunity", Frontiers in Immunology, vol. 9, Oct. 8, 2018, pp. 1-11, doi: 10.3389/fimmu.2018.02306.
Office Action dated Sep. 8, 2023, issued by European Patent Office in European Patent Application No. 19751922.6.
Communication dated Aug. 30, 2023 by Intellectual Property Office of New Zealand for New Zealand Patent Application No. 761547.
Communication dated Jun. 6, 2023 from the Japan Patent Office in Japanese Patent Application No. 2021-014538.
Office Action dated Dec. 28, 2022, issued by the Japan Patent Office in Japanese Patent Application No. 2021-014538.
Communication dated Nov. 15, 2021 issued by the European Patent Office in application No. 21184351.1.
Bluemel, C., et al., Epitope distance to the target cell membrane and antigen size determine the potency of T cell-mediated lysis by BiTE antibodies specific for a large melanoma surface antigen, Cancer Immunology, Immunotherapy, vol. 59, No. 8, Mar. 23, 2010, XP019842190, pp. 1197-1209.
Dickopf, S., et al., "Format and geometrics matter: Structure-based design defines the functionality of biospecific antibodies", Computational and Structural Biotechnology Journal, vol. 18, May 14, 2020, XP055740966, pp. 1221-1227.
Roda-Navarro, P., et al., " Understanding the Spatial Topology of Artificial Immunological Synapses Assembled in T Cell-Redirecting Strategies: A Major Issue in Cancer Immunotherapy", Frontiers in Cell and Developmental Biology, vol. 7, Jan. 10, 2020, XP55830746, pp. 1-5.
Supplemental European Search Report dated Apr. 11, 2006 in EP 04704324.5.
Communication dated Oct. 27, 2016, issued by the European Patent Office in European Application No. 12821886.4.
Communication dated Mar. 18, 2016, issued by the European Patent Office in European Patent Application No. 12821886.4.
Extended European Search Report dated Mar. 11, 2015 issued by the European Patent Office in European Application No. 12821886.4.
Communication from the European Patent Office dated Sep. 19, 2011, in European Application No. 04704324.5.
Communication dated Jan. 7, 2013, issued by the European Patent Office in European Application No. 10 176 748.1.
Communication dated Jan. 7, 2013, issued by the European Patent Office in European Applicant No. 04 704 324.5.
Communication dated Nov. 21, 2018, issued by the European patent Office in European Application No. 12821886.4.
International Search Report, dated Nov. 6, 2012, issued by the International Searching Authority in International Application No. PCT/JP2012/070498.
"PD-1 Antibody (J43)", Retrieved from the Internet: URL:https://www.novusbio.com/products/pd-1-antibody-j43_nbp1-43110, 2016, total 7 pages.
Declaration by Shiro Shibayama, filed on Apr. 1, 2011 in U.S. Appl. No. 12/469,188 (2 pages).
Sequence Alignment, Sequence 18 of U.S. Pat. No. 6,111,079, 2008.
Notification of Reasons for Refusal dated Oct. 27, 2016, issued by the Japanese Patent Office in Japanese Application No. 2013-528081.
Office Action dated May 23, 2014 issued by the Japanese Patent Office in Japanese Patent Application No. 2012-256828.
Office Action, dated Aug. 24, 2015, issued by the Japanese Patent Office in Japanese Patent Application No. 2012-256828.
Communication dated Oct. 6, 2017 by the Japanese Patent Office in Japanese Patent Application No. 2017-024163.
Communication dated May 18, 2016, issued by the Japanese Patent Office in Japanese Patent Application No. 2013-528081.
Communication dated Nov. 17, 2016, issued by the Japanese Patent Office in Japanese Patent Application No. 2015-239678.
Thibult et al., "PD-1 is a novel regulator of human B-cell activation", International Immunology, Feb. 2013, vol. 25, No. 2, pp. 129-137 (total 9 pages).

(56) References Cited

OTHER PUBLICATIONS

Okazaki et al., "PD-1 and PD-1 ligands: from discovery to clinical application," International Immunology, vol. 19, No. 7, 2007, pp. 813-824.

Keymeulen et al., "Insulin Needs after CD3-Antibody Therapy in New-Onset Type 1 Diabetes," The New England Journal of Medicine; vol. 352, No. 25; Jun. 23, 2005; pp. 2598-2608.

Kasagi et al., "Anti-PD-1 antibody reduces CD4+PD-1+T cells and relieves the lupus-like nephritis of NZB/W F1 mice," Proceedings of the Japanese Society for Immunology; vol. 39; Nov. 10, 2009; p. 160 (2 pages total).

Abiru, Norio, "Antigen specific treatment for the inhibition and remission of type 1 diabetes," The Japan Society for Clinical Immunology; vol. 31, No. 6; Dec. 2008; pp. 432-439.

W Chen, et al., "Attenuation of the programmed cell death-1 pathway increases the M1 polarization of macrophages induced by zymosan", Cell Death & Disease 2016, vol. 7, 2016, p. e2115, total 10 pages.

Tina Volkel et al., "Optimized linker sequences for the expression of monomeric and dimeric bispecific single-chain diabodies", Protein Engineering, 2001, 14(10): 815-823.

Teresa K. Attwood, "The Babel of Bioinfomatics", Science, 2000, 290: 471-473.

Jeffrey Skolnick et al., "From genes to protein structure and function: novel applications of computational approaches in the genomic era", Tibtech, 2000, 18(1): 34-39.

Margitta Alt et al., "Novel tetravalent and bispecific IgG-like antibody molecules combining single-chain diabodies with the immunoglobin ?1 Fc or CH3 region", FEBS Letters, 1999, 454: 90-94.

Laura L. Carter et al., "PD-1: PD-L inhibitory pathway affects both CD4+ and CD8+ T cells and is overcome by IL-2", Eur. J. Immunol., 2002, 32: 634-643.

Bennett et al. "Program Death-1 Engagement Upon TCR Activation has Distinct Effects on Costimulation and Cytokine-driven Proliferation: Attenuation of ICOS, IL-4, and IL-21, but not CD28, IL-7, and IL-15 Responses." The Journal of Immunology, vol. 170, Jan. 1, 2003 (Jan. 1, 2003): 711-718. XP055048008, ISSN:0022-1767.

Zuberek K, et al., "The Role of In Vivo Pd-1/Pd-L1 Interactions In Syngeneic and Allogeneic Antitumor Responses in Murine Tumor Models", Blood, American Society of Hematology, US, vol. 98, No. 11, Part 02, Dec. 11, 2001 (Dec. 11, 2001), p. 42B, ABSTRACT3772, XP008068416, ISSN : 0006-4971. (3 pages total).

Gordon J. Freeman et al., "Engagement of the PD-1 Immunoinhibitory Receptor by a Novel B7 Family Member Leads to Negative Regulation of Lymphocyte Activation", J. Exp. Med., 2000, 192(7): 1027-1034.

Engin Ozkaynak et al., "Programmed Death-1 Targeting Can Promote Allograft Survival", The Journal of Immunology, 2002, vol. 169, 6546-6553.

Peter J. Hudson et al., "High avidity scFv multimers; diabodies and triabodies", Journal of Immunological Methods, 1999, 231: 177-189.

Holliger, Philipp, et al., ""Diabodies": Small bivalent and bispecific antibody fragments", Proc. Natl. Acad. Sci. USA: Biophysics, Jul. 1993, vol. 90, pp. 6444-6448.

Takemura, Shin-ichi, et al., "Construction of a diabody (small recombinant bispecific antibody) using a refolding system", Protein Engineering, 2000, vol. 13, No. 8, pp. 583-588.

Godeau, Francois, et al., "Purification and Ligand Binding of a Soluble Class I Major Histocompatibility Complex Molecule Consisting of the First Three Domains of H-2Kd Fused to ß2-Microglobulin Expressed in the Baculovirus-Insect Cell System", The Journal of Biological Chemistry, The American Society for Biochemistry and Molecular Biology, Inc., 1992, vol. 267, No. 34, Issue Dec. 5, 1992, pp. 24223-24229.

R.L. Rabin et al., "The nexus between atopic disease and autoimmunity: a review of the epidemiological and mechanistic literature", Clinical & Experimental Immunology, 2008, 153: 19-30.

Perisic, Olga, et al., "Crystal structure of a diabody, a bivalent antibody fragment," Current Biology Ltd., ISSN 0969-2126, 1994, vol. 2, No. 12, pp. 1217-1226.

Ziwei Huang, "Structural chemistry and therapeutic intervention of protein-protein interactions in immune response, human immunodeficiency virus entry, and apoptosis", Pharmacology & Therapeutics, 2000, 86: 201-215.

Bruce R. Blazar et al., "Infusion of Anti-B7.1 (CD80) and Anti-B7.2 (CD86) Monoclonal Antibodies Inhibits Murine Graft-Versus-Host Disease Lethality in Part via Direct Effects on CD4+ and CD8+ T Cells1", The Journal of Immunology, 1996, 157: 3250-3259.

Anonymous, OKT 3 (ATCC® CRL-8001™), 2019, 2 pages total.

Rose, N, "Prediction and Prevention of Autoimmune Disease in the 21st Century: A Review and Preview", 2016, American Journal of Epidemiology, vol. 183, No. 5 (4 pages).

Salama, Alan D. et al., "Critical Role of the Programmed Death-1 (PD-1) Pathway in Regulation of Experimental Autoimmune Encephalomyelitis", The Journal of Experimental Medicine, Jul. 1, 2003, vol. 198, No. 1, pp. 71-78.

Ansari, Mohammed Javeed I., "The Programmed Death-1 (PD-1) Pathway Regulates Autoimmune Diabetes in Non-obese Diabetic (NOD) Mice", The Journal of Experimental Medicine, Jul. 7, 2003, vol. 198, No. 1, pp. 63-69.

Terawaki, Seigo et al., "Specific and high-affinity binding of tetramerized PD-L1 extracellular domain to PD-1-expressing cells: possible application to enhance T cell function", International Immunology, Jul. 2, 2017, vol. 19, No. 7, pp. 881-890.

Kasagi, Shimpei et al., "Anti-Programmed Cell Death 1 Antibody Reduces CD4+PD-1+ T Cells and Relieves the Lupus-Like Nephritis of NZB/W F1 Mice", The Journal of Immunology, 2010, vol. 184, pp. 2337-2347.

Mayo Clinic Staff, "Type 1 diabetes", MAYO CLINIC, retrieved from the internet on Sep. 13, 2012, [http://www.mayoclinic.com/health/type-1-diabetes/DS00329], pp. 1-20.

Aly et al., "Immunotherapeutic Approaches to Prevent, Ameliorate, and Cure Type 1 Diabetes", American Journal of Therapeutics, 2005, vol. 12, pp. 481-490.

International Searching Authority, International Preliminary Report on Patentability dated Aug. 11, 2020 in International Application No. PCT/JP2019/004551.

International Searching Authority, Written Opinion dated May 14, 2019 in International Application No. PCT/JP2019/004551.

Extended European Search Report dated Apr. 12, 2022, issued by the European Patent Office in counterpart European Patent Application No. 19751922.6.

Office Action dated Feb. 28, 2023 by the National Intellectual Property Administration, PRC in corresponding Chinese Application No. 201980011156.0.

Zhongqing Zheng et al., "Research Progress on Regulation of Lymphocyte Differentiation and Involvement in Onset of Autoimmune Diseases by PD-1 Pathway", Journal of Tianjin Medical University, vol. 22, No. 6, Nov. 2016, (10 pages).

Search Report dated Dec. 5, 2022 by the Russian Patent Office for Russian Patent Application No. 2020125508.

Office Action dated Dec. 5, 2022 by the Russian Patent Office for Russian Patent Application No. 2020125508.

Communication dated Jun. 14, 2023 from the European Patent Office in EP Patent Application No. 20836994.2.

Hermann, Monika, et al., "Bifunctional PD-1 × αCD3 × αCD33 fusion protein reverses adaptive immune escape in acute myeloid leukemia", Blood, vol. 132, No. 23, Dec. 6, 2018, pp. 2484-2494, doi:10.1182/blood-2018-05-849802.

Tsirigotis, Panagiotis, et al., "Programmed death-1 immune checkpoint blockade in the treatment of hematological malignancies", Annals of Medicine, vol. 48, No. 6, Aug. 17, 2016, pp. 428-439, https://doi.org/10.1080/07853890.2016.1186827.

Li, Ling, et al., "PD-1/PD-L1 expression and interaction by automated quantitative immunofluorescent analysis show adverse prognostic impact in patients with diffuse large B-cell lymphoma having T-cell infiltration: a study from the International DLBCL Consortium Program", Nature Publishing Group, GB, vol. 32, No. 6, Jan. 21, 2019, pp. 741-754, https://d0i.0rg/10.1038/S41379-018-0193-5.

(56) References Cited

OTHER PUBLICATIONS

Duell, Johannes, et al., "Bispecific Antibodies in the Treatment of Hematologic Malignancies", Clinical Pharmacology and Therapeutics, vol. 106, No. 4, Mar. 29, 2019 , pp. 781-791, doi:10.1G02/cpt.I3S6.
Hirotake, Shiraiwa, et al., "Engineering a bispecific antibody with a common light chain: Identification and optimization of an anti-CD3 epsilon and anti-GPC3 bispecific antibody, ERY974", Methods, vol. 154, Feb. 1, 2019, pp. 10-20, https://doi.org/10.1016/j.ymeth.2018.10.005.
Annibali, O., et al., "PD-1 /PD-L1 checkpoint in hematological malignancies", Leukemia Research, vol. 67, Apr. 1, 2018, pp. 45-55, https://doi.org/10.1016/j.lenkre.2018.01.014.
Extended European Search Report dated Oct. 13, 2023 by the European Patent Office in European Patent Application No. 20846826.4.
Office Action dated Oct. 27, 2023 by the Indonesian Patent Office in Indonesian Patent Application No. P00202200716.
Communication issued Nov. 21, 2023 by the Russian Federation in Russian Patent Application No. 2022101682.
Extended European Search Report dated Apr. 8, 2024, issued by the European Patent Office in counterpart European Patent Application No. 21788761.1.
Japanese Patent Office, Notice of Reasons for Refusal issued May 7, 2024, in copending Japanese Application No. 2021-025286.
Japanese Patent Office, Office Action mailed May 27, 2004 in copending Application No. 2021-067509.
Inaba et al., "Angioiiwnunoblastic T-cell lymphoma: AITL", Journal of Clinical Laboratory Medicine, 2013, 57, pp. 1634-1637, with English translation.
Huang, et al., "A skewed distribution and increased PD-1+Vβ+ CD4+/CD8+ T cells in patients with acute myeloid leukemia", J. Leukoc. Biol., May 28, 2019, 106, pp. 725-732.
Korean Patent Office, Office Action issued Jun. 27, 2024 in copending Korean Application No. 10-2020-7022608 with English translation.
Japanese Office Action issued Jul. 10, 2024, in copending Application No. 2021-025286, with English translation.

* cited by examiner

Figure 1

| Common Light Chain | SEQ ID No. | Amino Acid Sequence |
|---|---|---|
| Variable Region | 25 | DIQMTQSPSSLSASVGDRVTITCRASQSISSYLNWYQQKPGKAPK LLIYAASSLQSGVPSRFSGSGSGTDFTLTISSLQPEDFATYYCQQS YSTPPTFGQGTKVEIK |
| Constant Region | 29 | RTVAAPSVFIFPPSDEQLKSGTASVVCLLNNFYPREAKVQWKVD NALQSGNSQESVTEQDSKDSTYSLSSTLTLSKADYEKHKVYACE VTHQGLSSPVTKSFNRGEC |

*Figure 2*

| Common Light Chain | SEQ ID No. | CDR1 | SEQ ID No. | CDR2 | SEQ ID No. | CDR3 |
|---|---|---|---|---|---|---|
| CDRs | 26 | RASQSISSYLN | 27 | AASSLQS | 28 | QQSYSTPPT |

Figure 3

| Germline V gene | SEQ ID No. | Amino Acid Sequence |
|---|---|---|
| IGHV7-4-1 | 21 | QVQLVQSGSELKKPGASVKVSCKASGYTFTSYAMNWVRQAPGQGLEWMGWINTNTGNPTYAQGFTGRFVFSLDTSVSTAYLQICSLKAEDTAVYYCAR |
| IGHV3-33 | 22 | QVQLVESGGGVVQPGRSLRLSCAASGFTFSSYGMHWVRQAPGKGLEWVAVIWYDGSNKYYADSVKGRFTISRDNSKNTLYIQMNSLRAEDTAVYYCAR |

Figure 4

Alignment between each VH of PD1-1 to PD1-5 and IGHV7-4-1/JH6c

|  | ——FR1—— | —CDR1— | ——FR2—— | ———CDR2——— |
|---|---|---|---|---|
| IGHV7-4-1 (SEQ ID No. 21) | QVQLVQSGSELKKPGASVKVSCKASGYTFT | SYAMN | WVRQAPGQGLEWMG | WINTNTGNPTYAQGFTG |
| PD1-1 VH (SEQ ID No. 1) | ------------Q----------------- | H-GLH | -------------- | --L--------E---F- |
| PD1-2 VH (SEQ ID No. 2) | ------------Q-V--------------- | H-GLH | -------------- | --L--------E---F- |
| PD1-3 VH (SEQ ID No. 3) | --------------M---------Q----- | H--LH | -------------- | --L--------E---F- |
| PD1-4 VH (SEQ ID No. 4) | ------------Q----------------- | H--LH | -------------- | --L--------E---F- |
| PD1-5 VH (SEQ ID No. 5) | ------------Q----------------- | H--LH | -L------------ | --L--------E---F- |

|  | ————FR3———— | ——CDR3—— | —FR4— |
|---|---|---|---|
| IGHV7-4-1 (SEQ ID No. 21) | RFVFSLDTSVSTAYLQICSLKAEDTAVYYCAR | | |
| D gene (unknown) | | HYYYYYYMDV | |
| JH6c | | | WGKGTTVTVSS |
| PD1-1 VH (SEQ ID No. 1) | ------------------S------------T | GDMVVPTTIWN---HF | ---------N--L |
| PD1-2 VH (SEQ ID No. 2) | ------------------S------------- | GDLVVPTTIWN---H--E | ------------L |
| PD1-3 VH (SEQ ID No. 3) | ------------------N------------T | GDMVVPTTIWN--- | -------------- |
| PD1-4 VH (SEQ ID No. 4) | ------------------S------------T | GDMVVPTTIWN---HF | ---------N--- |
| PD1-5 VH (SEQ ID No. 5) | ------------------S------------T | GDMVVPTTIWN---HF | ---------Q--- |

*Figure 5*

| Clone No. | SEQ ID No. | Amino Acid Sequence |
|---|---|---|
| PD1-1 | 1 | QVQLVQSGSELKQPGASVKVSCKASGYTFTHYGLHWVRQAPGQGLEWMGW LNTNENPTFAQGFTGRFVFSLDTSVTAYLQISSLKAEDTAVYYCARGDMV VPTTWNYYHFMDVWGNGTLVTVSS |
| PD1-2 | 2 | QVQLVQSGSELKQPGVSVKVSCKASGYTFTHYGLHWVRQAPGQGLEWMGWI NTNTGNPTYAQGFTGRFVFSLDTSVSTAYLQISSLKAEDTAVYYCARGDLVV PTTIWNYYHYMEVWGKGTLVTVSS |
| PD1-3 | 3 | QVQLVQSGSELKKPGASVMVSCKASGYTFTHYALHWVRQAPGQGLEWMGW LNTNENPTYAQGFTGRFVFSLDTSVTAYLQINSLKAEDTAVYYCARGDMV VPTTIWNYYYYMDVWGKGTVTVSS |
| PD1-4 | 4 | QVQLVQSGSELKQPGASVKVSCKASGYTFTHYALHWLRQAPGQGLEWMGWL NTNENPTFAQGFTGRFVFSLDTSVTTAYLQISSLKAEDTAVYYCARGDMVV PTTIWNYYHFMDVWGNGTTVTVSS |
| PD1-5 | 5 | QVQLVQSGSELKQPGASVKVSCKASGYTFTHYALHWLRQAPGQGLEWMGWL NTNENPTFAQGFTGRFVFSLDTSVTTAYLQISSLKAEDTAVYYCARGDMVV PTTIWNYYHFMDVWGQGTTVTVSS |

Figure 6

| Clone No. | SEQ ID No. | CDR1  | SEQ ID No. | CDR2              | SEQ ID No. | CDR3              |
|-----------|------------|-------|------------|-------------------|------------|-------------------|
| PD1-1     | 6          | HYGLH | 7          | WLNTNTENPTFAQGFTG | 8          | GDMVVPTTIWNYYHFMDV |
| PD1-2     | 9          | HYGLH | 10         | WINTNTGNPTYAQGFTG | 11         | GDLVVPTTIWNYYHYMEV |
| PD1-3     | 12         | HYALH | 13         | WLNTNTENPTYAQGFTG | 14         | GDMVVPTTIWNYYYYMDV |
| PD1-4     | 15         | HYALH | 16         | WLNTNTENPTFAQGFTG | 17         | GDMVVPTTIWNYYHFMDV |
| PD1-5     | 18         | HYALH | 19         | WLNTNTENPTFAQGFTG | 20         | GDMVVPTTIWNYYHFMDV |

Figure 7

| Clone No. | SEQ ID No. | Amino Acid Sequence |
|---|---|---|
| CD3-2 | 36 | QVQLVQSGGGVVQPGRSLRLSCVASGFTFSSYGMHWVRQAPGKGLEWV AQIWYNARKQEYSDSVKGRFTISRDNSKNTLYLQMNSLRAEDTAVYYCT RGTGYNWFDPWGQGTLVTVSS |

*Figure 8*

| Clone No. | SEQ ID No. | CDR1 | SEQ ID No. | CDR2 | SEQ ID No. | CDR3 |
|---|---|---|---|---|---|---|
| CD3-2 | 37 | SYGMH | 38 | QIWYNARKQEYSDSVKG | 39 | GTGYNWFDP |

*Figure 9*

| | SEQ ID No. | Amino Acid Sequence |
|---|---|---|
| Heavy chain constant region having the VH of the first arm specifically binding to PD-1 | 23 | ASTKGPSVFPLAPSSKSTSGGTAALGCLVKDYFPEPVTVSWNSGALTSGVHTFPA VLQSSGLYSLSSVVTVPSSSLGTQTYICNVNHKPSNTKVDKRVEPKSCDKTHTCPP CPAPELGRGPSVFLFPPKPKDTLMISRTPEVTCVVVDVSHEDPEVKFNWYVDGVE VHNAKTKPREEQYNSTYRVVSVLTVLHQDWLNGKEYKCKVSNKALPAPIEKTISK AKGQPREPQVYTDPPSREEMTKNQVSLTCEVKGFYPSDIAVEWESNGQPENNYK TTPPVLDSDGSFFLYSKLTVDKSRWQQGNVFSCSVMHEALHNHYTQKSLSLSPG |
| Heavy chain constant region having the VH of the second arm specifically binding to CD3 | 24 | ASTKGPSVFPLAPSSKSTSGGTAALGCLVKDYFPEPVTVSWNSGALTSGVHTFPA VLQSSGLYSLSSVVTVPSSSLGTQTYICNVNHKPSNTKVDKRVEPKSCDKTHTCPP CPAPELGRGPSVFLFPPKPKDTLMISRTPEVTCVVVDVSHEDPEVKFNWYVDGVE VHNAKTKPREEQYNSTYRVVSVLTVLHQDWLNGKEYKCKVSNKALPAPIEKTISK AKGQPREPQVYTKPPSREEMTKNQVSLKCLVKGFYPSDIAVEWESNGQPENNYK TTPPVLDSDGSFFLYSKLTVDKSRWQQGNVFSCSVMHEALHNHYTQKSLSLSPG |

*Figure 10*

Amino acid sequence of the VH of the 15C3 clone

QVQLVQSGGGVVQPGRSLRLSCVASGFTFSSYGMHWVRQAPGKGLEWVAAIWYNGRKQDYADSVKGRFTISRDNSKN
TLYLQMNSLRAEDTAVYYCTRGTGYNWFDPWGQGTLVTVSS

Figure 11

| Binding activity to PD-1 of the first arm | | |
|---|---|---|
| Clone No. | HumanPD-1 | Cynomolgus monkey PD-1 |
| | Kd (nmol/L) | Kd (nmol/L) |
| PD1-1(Bi) | 0.6 | 0.3 |
| PD1-2(Bi) | 0.7 | 0.4 |
| PD1-3(Bi) | 3.8 | 2.0 |
| PD1-4(Bi) | 0.9 | 0.7 |
| PD1-5(Bi) | 0.7 | 0.4 |
| PD1-6(Bi) | 0.8 | 21.8 |
| Binding activity to CD3 of the second arm | | |
| Clone No. | Human CD3δ/CD3ε | |
| | Kd (nmol/L) | |
| CD3-2 | 19.2 | |

BISPECIFIC ANTIBODY

CROSS REFERENCE TO RELATED APPLICATIONS

This is a Continuation of application Ser. No. 16/967,668 filed Aug. 5, 2020, which is National Stage of International Application No. PCT/JP2019/004551 filed Feb. 8, 2019, which claims priority based on Japanese Patent Application Nos. 2018-021498 filed Feb. 9, 2018 and 2018-153149 filed Aug. 16, 2018, the contents of all of which are incorporated herein by reference in their entirety.

TECHNICAL FIELD

The present invention relates to a bispecific antibody capable of specifically binding to PD-1 and CD3 respectively (hereinafter, which is abbreviated as a "PD-1/CD3 bispecific antibody"), and a pharmaceutical composition containing the same as an active ingredient, as well as pharmaceutical therapeutic use thereof.

BACKGROUND ART

PD-1 is an immunosuppressive receptor belonging to an immunoglobulin family and is a molecule having a function of suppressing the immune activation signals of T-cells activated by stimulation through an antigen receptor. From analysis of PD-1 knock-out mice or the like, it is known that PD-1 signals play important roles in suppression of autoimmune diseases such as autoimmune dilated cardiomyopathy, lupus-like syndrome, autoimmune encephalomyelitis, systemic lupus erythematosus, graft-versus-host disease, type I diabetes mellitus, and rheumatoid arthritis. Accordingly, it is pointed out that an agent enhancing the PD-1 signal could be a prophylactic or therapeutic agent for autoimmune diseases.

Bispecific antibodies recognizing PD-1 have been known as an agent enhancing a PD-1 signal (Patent references 1 to 3) before. The bispecific antibodies are composed of an antigen-recognition site of an antibody recognizing CD3 that is a member of a T-cell receptor complex, and an antigen-recognition site of an antibody recognizing PD-1 linked to each other using genetic engineering. The bispecific antibodies have an action of enhancing the inhibitory signal of PD-1 against the T-cell receptor complex by increasing the frequency of bringing PD-1 to the vicinity of the T-cell receptor complex. Furthermore, the Patent Literatures also state that PD-1 bispecific antibodies can be used for prophylaxis or therapy of autoimmune diseases.

Incidentally, in protein formulation, expression of adverse reactions called infusion reaction or cytokine release syndrome immediately after administration have been concerned. Formulations in which such reactions are reduced or suppressed have been demanded.

In the PD-1/CD3 bispecific antibody of the present invention, cytokine production stimulation after administration, which is considered to be a cause of the above-mentioned adverse reactions, is sufficiently reduced. Therefore, the PD-1/CD3 bispecific antibody is expected to be a pharmaceutical in which expression of the concerned adverse reaction is suppressed.

Bispecific antibodies having such characteristics have not been reported to date.

CITATION LIST

Patent References

Patent Reference 1: International Publication No. WO2003/011911
Patent Reference 2: International Publication No. WO2004/072286
Patent Reference 3: International Publication No. WO2013/022091

SUMMARY OF INVENTION

Technical Problem

The object of the present invention is to provide a new pharmaceutical agent for preventing, suppressing symptom progression or recurrence of or treating autoimmune diseases and the like.

Solution to Problem

The present inventors have diligently studied and have focused on the PD-1/CD3 bispecific antibody of the present invention as an agent capable of solving the above-mentioned problem. The present inventors further have verified that the PD-1/CD3 bispecific antibody could be an agent in which expression of reactions called infusion reaction or cytokine release syndrome is reduced, and have completed the present invention.

Furthermore, the inventors of the present invention have found that the PD-1/CD3 bispecific antibody has characteristics of allowing interaction between the PD-1 and PD-L1 as its ligand, and found that such characteristics contribute to enhancing or sustaining of the effect of the PD-1/CD3 bispecific antibody.

That is, the present invention relates to the followings.

[1] A PD-1/CD3 bispecific antibody or antibody fragment thereof, having the first arm specifically binding to PD-1 and the second arm specifically binding to CD3, wherein the first arm specifically binding to PD-1 contains any one of VH selected from:

(A) a heavy chain variable region (hereinafter, the "heavy chain variable region" may be abbreviated as "VH") having
  (a) a complementary determining region 1 of the heavy chain variable region (hereinafter, the "complementary determining region 1 of the heavy chain variable region" may be abbreviated as "VH-CDR1") comprising an amino acid sequence set forth in SEQ ID No. 6;
  (b) a complementary determining region 2 of the heavy chain variable region (hereinafter, the "complementary determining region 2 of the heavy chain variable region" may be abbreviated as "VH-CDR2") comprising an amino acid sequence set forth in SEQ ID No. 7; and
  (c) a complementary determining region 3 of the heavy chain variable region (hereinafter, the "complementary determining region 3 of the heavy chain variable region" may be abbreviated as "VH-CDR3") comprising an amino acid sequence set forth in SEQ ID No. 8;

(B) a VH having
  (a) a VH-CDR1 comprising an amino acid sequence set forth in SEQ ID No. 9;

(b) a VH-CDR2 comprising an amino acid sequence set forth in SEQ ID No. 10; and
(c) a VH-CDR3 comprising an amino acid sequence set forth in SEQ ID No. 11;
(C) a VH having
(a) a VH-CDR1 comprising an amino acid sequence set forth in SEQ ID No. 12;
(b) a VH-CDR2 comprising an amino acid sequence set forth in SEQ ID No. 13, and
(c) a VH-CDR3 comprising an amino acid sequence set forth in SEQ ID No. 14;
(D) a VH having
(a) a VH-CDR1 comprising an amino acid sequence set forth in SEQ ID No. 15;
(b) a VH-CDR2 comprising an amino acid sequence set forth in SEQ ID No. 16; and
(c) a VH-CDR3 comprising an amino acid sequence set forth in SEQ ID No. 17; and
(E) a VH having
(a) a VH-CDR1 comprising an amino acid sequence set forth in SEQ ID No. 18;
(b) a VH-CDR2 comprising an amino acid sequence set forth in SEQ ID No. 19; and
(c) a VH-CDR3 comprising an amino acid sequence set forth in SEQ ID No. 20; and
wherein the second arm specifically binding to CD3 contains a VH having
(a) a VH-CDR1 comprising an amino acid sequence set forth in SEQ ID No.37;
(b) a VH-CDR2 comprising an amino acid sequence set forth in SEQ ID No.38; and
(c) a VH-CDR3 comprising an amino acid sequence set forth in SEQ ID No.39.

[2] The PD-1/CD3 bispecific antibody or antibody fragment thereof according to the preceding item [1], wherein one to five arbitrary amino acid residue(s) may be respectively substituted with other amino acid(s) (preferably, conservative amino acid(s) thereof) in any one or more of VH-CDR(s) selected from the VH-CDR1, VH-CDR2 and VH-CDR3 in the first arm specifically binding to PD-1; and/or one to five arbitrary amino acid residue(s) may be respectively substituted with other amino acid(s) (preferably, conservative amino acid(s) thereof) in any one or more of VH-CDR(s) selected from the VH-CDR1, VH-CDR2 and VH-CDR3 in the second arm specifically binding to CD3.

[3] The PD-1/CD3 bispecific antibody or antibody fragment thereof according to the preceding item [1] or [2], wherein
(i) the VH of the first arm specifically binding to PD-1 has:
(a) the VH-CDR1 comprising the amino acid sequence set forth in SEQ ID No. 6,
(b) the VH-CDR2 comprising the amino acid sequence set forth in SEQ ID No. 7, and
(c) the VH-CDR3 comprising the amino acid sequence set forth in SEQ ID No. 8; and
(ii) the VH of the second arm specifically binding to CD3 has:
(a) the VH-CDR1 comprising the amino acid sequence set forth in SEQ ID No. 37,
(b) the VH-CDR2 comprising the amino acid sequence set forth in SEQ ID No. 38, and
(c) the VH-CDR3 comprising the amino acid sequence set forth in SEQ ID No. 39.

[4] The PD-1/CD3 bispecific antibody or antibody fragment thereof according to the preceding item [1] or [2], wherein
(i) the VH of the first arm specifically binding to PD-1 has:
(a) the VH-CDR1 comprising the amino acid sequence set forth in SEQ ID No. 9,
(b) the VH-CDR2 comprising the amino acid sequence set forth in SEQ ID No. 10, and
(c) the VH-CDR3 comprising the amino acid sequence set forth in SEQ ID No. 11; and
(ii) the VH of the second arm specifically binding to CD3 has:
(a) the VH-CDR1 comprising the amino acid sequence set forth in SEQ ID No. 37,
(b) the VH-CDR2 comprising the amino acid sequence set forth in SEQ ID No. 38, and
(c) the VH-CDR3 comprising the amino acid sequence set forth in SEQ ID No. 39.

[5] The PD-1/CD3 bispecific antibody or antibody fragment thereof according to the preceding item [1] or [2], wherein
(i) the VH of the first arm specifically binding to PD-1 has
(a) the VH-CDR1 comprising the amino acid sequence set forth in SEQ ID No. 12,
(b) the VH-CDR2 comprising the amino acid sequence set forth in SEQ ID No. 13, and
(c) the VH-CDR3 comprising the amino acid sequence set forth in SEQ ID No. 14, and
(ii) the VH of the second arm specifically binding to CD3 has:
(a) the VH-CDR1 comprising the amino acid sequence set forth in SEQ ID No. 37,
(b) the VH-CDR2 comprising the amino acid sequence set forth in SEQ ID No. 38, and
(c) the VH-CDR3 comprising the amino acid sequence set forth in SEQ ID No. 39.

[6] The PD-1/CD3 bispecific antibody or antibody fragment thereof according to the preceding item [1] or [2], wherein
(i) the VH of the first arm specifically binding to PD-1 has:
(a) the VH-CDR1 comprising the amino acid sequence set forth in SEQ ID No. 15,
(b) the VH-CDR2 comprising the amino acid sequence set forth in SEQ ID No. 16, and
(c) the VH-CDR3 comprising the amino acid sequence set forth in SEQ ID No. 17; and
(ii) the VH of the second arm specifically binding to CD3 has:
(a) the VH-CDR1 comprising the amino acid sequence set forth in SEQ ID No. 37,
(b) the VH-CDR2 comprising the amino acid sequence set forth in SEQ ID No. 38, and
(c) the VH-CDR3 comprising the amino acid sequence set forth in SEQ ID No. 39.

[7] The PD-1/CD3 bispecific antibody or an antibody fragment thereof according to the preceding item [1] or [2], wherein
(i) the VH of the first arm specifically binding to PD-1 has:
(a) the VH-CDR1 comprising the amino acid sequence set forth in SEQ ID No. 18,
(b) the VH-CDR2 comprising the amino acid sequence set forth in SEQ ID No. 19, and (c) the VH-CDR3 comprising the amino acid sequence set forth in SEQ ID No. 20; and
(ii) the VH of the second arm specifically binding to CD3 has:
(a) the VH-CDR1 comprising the amino acid sequence set forth in SEQ ID No. 37,
(b) the VH-CDR2 comprising the amino acid sequence set forth in SEQ ID No. 38, and
(c) the VH-CDR3 comprising the amino acid sequence set forth in SEQ ID No. 39.

[8] A PD-1/CD3 bispecific antibody or antibody fragment thereof, having the first arm specifically binding to PD-1 and the second arm specifically binding to CD3, wherein the first arm specifically binding to PD-1 contains a VH having;
(a) a VH-CDR1 comprising an amino acid sequence represented by HYJ$^1$LH [wherein J$^1$ represents G (glycine) or A (alanine), and alphabets represented by J$^1$ or other represent one-letter amino-acid abbreviation, respectively],
(b) a VH-CDR2 comprising an amino acid sequence represented by WJ$^2$NTNTU$^2$NPTX$^2$AQGFTG [wherein J$^2$ represents L (leucine) or I (isoleucine), U$^2$ represents E (glutamic acid) or G (glycine), X$^2$ represents F (phenylalanine) or Y (tyrosine), and alphabets represented by J$^2$, U$^2$ or X$^2$, or other represent the same as the above, respectively], and
(c) a VH-CDR3 comprising an amino acid sequence represented by GDJ$^3$VVPTTIWNYYU$^3$X$^3$MZ$^3$V [wherein J$^3$ represents M (methionine) or L (leucine), U$^3$ represents H (histidine) or Y (tyrosine), X$^3$ represents F (phenylalanine) or Y (tyrosine), Z$^3$ represents D (aspartic acid) or E (glutamic acid), and alphabets represented by J$^3$, U$^3$, X$^3$ or Z$^3$, or other alphabets represent the same as the above, respectively], and;
wherein the second arm specifically binding to CD3 contains the VH having:
(a) the VH-CDR1 comprising the amino acid sequence set forth in SEQ ID No. 37,
(b) the VH-CDR2 comprising the amino acid sequence set forth in SEQ ID No. 38, and
(c) the VH-CDR3 comprising the amino acid sequence set forth in SEQ ID No. 39.

[9] The PD-1/CD3 bispecific antibody or antibody fragment thereof according to the preceding item [8], wherein
(a) J$^1$ represents G (glycine), J$^2$ represents L (leucine), U$^2$ represents E (glutamic acid), X$^2$ represents F (phenylalanine), J$^3$ represents M (methionine), U$^3$ represents H (histidine), X$^3$ represents F (phenylalanine), and Z$^3$ represents D (aspartic acid);
(b) J$^1$ represents G (glycine), J$^2$ represents I (isoleucine), U$^2$ represents G (glycine), X$^2$ represents Y (tyrosine), J$^3$ represents L (leucine), U$^3$ represents H (histidine), X$^3$ represents Y (tyrosine), and Z$^3$ represents E (glutamic acid);
(c) J$^1$ represents A (alanine), J$^2$ represents L (leucine), U$^2$ represents E (glutamic acid), X$^2$ represents Y (tyrosine), J$^3$ represents M (methionine), U$^3$ represents Y (tyrosine), X$^3$ represents Y (tyrosine), and Z$^3$ represents D (aspartic acid); or
(d) J$^1$ represents A (alanine), J$^2$ represents L (leucine), U$^2$ represents E (glutamic acid), X$^2$ represents F (phenylalanine), J$^3$ represents M (methionine), U$^3$ represents H (histidine), X$^3$ represents F (phenylalanine), and Z$^3$ represents D (aspartic acid).

[10] The PD-1/CD3 bispecific antibody or an antibody fragment thereof according to any one of the preceding items [1] to [9], wherein the framework region 1 (hereinafter, may be abbreviated as "FR1"), the framework region 2 (hereinafter, may be abbreviated as "FR2") and the framework region 3 (hereinafter, may be abbreviated as "FR3") in a framework region (hereinafter, "framework" may be abbreviated as "FR") in the VH of the first arm specifically binding to PD-1 correspond to amino acid sequences encoded by the germ-line V gene IGHV7-4-1 or gene thereof with somatic mutation(s), respectively.

[11] The PD-1/CD3 bispecific antibody or antibody fragment thereof according to the preceding item [10], wherein the framework 4 (hereinafter, "the framework 4" may be abbreviated as "FR4") region in the VH of the first arm specifically binding to PD-1 includes an amino acid sequence (excluding the amino acid sequence included in the VH-CDR3) encoded by the germ-line J gene JH6c or gene thereof with somatic mutation(s).

[12] The PD-1/CD3 bispecific antibody or antibody fragment thereof according to the preceding item [10] or [11], wherein the FR region in the VH of the first arm specifically binding to PD-1 is encoded by the germ-line V gene IGHV7-4-1 with somatic mutation(s), and wherein the FR region contains the FR1 region in which in the amino acid sequence set forth in SEQ ID No. 21, by the somatic mutation, lysine at position 13 is or may be substituted with glutamine, alanine at position 16 is or may be substituted with valine, or lysine at position 19 is or may be substituted with methionine, respectively, or which are or may be carried out in arbitrary combination of a plurality thereof.

[13] The PD-1/CD3 bispecific antibody or antibody fragment thereof according to any one of the preceding items [10] to [12], wherein the FR region of the VH in the first arm specifically binding to PD-1 is encoded by the germ-line V gene IGHV7-4-1 with somatic mutation(s), and wherein the FR region contains the FR2 region in which in the amino acid sequence set forth in SEQ ID No. 21, valine at position 37 is or may be substituted with leucine, by the somatic mutation.

[14] The PD-1/CD3 bispecific antibody or antibody fragment thereof according to any one of the preceding items [10] to [13], wherein the FR region of the VH in the first arm specifically binding to PD-1 is encoded by the germ-line V gene IGHV7-4-1 with somatic mutation(s), and wherein the FR region contains the FR3 region in which in the amino acid sequence set forth in SEQ ID No. 21, by the somatic mutation, serine at position 77 is or may be substituted with threonine or cysteine at position 84 is or may be substituted with serine or asparagine, respectively, or which are or may be carried out in arbitrary combination of a plurality thereof.

[15] The PD-1/CD3 bispecific antibody or antibody fragment thereof according to any one of the preceding items [10] to [14], wherein the FR4 region of the VH of the first arm specifically binding to PD-1 is encoded by the germ-line J gene JH6c with somatic mutation(s) (excluding the gene region encoding VH-CDR3), and wherein in the amino acid sequence (Trp-Gly-Lys-Gly-Thr-Thr*-Val-Thr-Val-Ser-Ser)(SEQ ID No. 41) of the FR4 region, lysine (Lys) is or may be substituted with glutamine or asparagine and/or threonine (Thr) marked with an asterisk is or may be substituted with leucine.

[16] The PD-1/CD3 bispecific antibody or antibody fragment thereof according to any one of the preceding items [1] to [15], wherein the VH of the first arm specifically binding to PD-1 comprises the amino acid sequence set forth in any one selected from SEQ ID No. 1, SEQ ID No. 2, SEQ ID No. 3, SEQ ID No. 4, and SEQ ID No. 5, or an amino acid sequence having an identity of at least 80%, 90%, 95%, 98% or 99% to amino acid sequence thereof.

[17] The PD-1/CD3 bispecific antibody or antibody fragment thereof according to any one of the preceding items [1] and [3] to [7], wherein the VH of the first arm specifically binding to PD-1 comprises the amino acid sequence set forth in any one selected from SEQ ID No. 1, SEQ ID No. 2, SEQ ID No. 3, SEQ ID No. 4, and SEQ ID No. 5.

[18] The PD-1/CD3 bispecific antibody or antibody fragment thereof according to any one of the preceding items [1] to [17], wherein the VH of the second arm specifically binding to CD3 comprises an amino acid sequence set forth in SEQ ID No. 36 or an amino acid sequence having an identity of at least 80%, 90%, 95%, 98% or 99% to amino acid sequence thereof.

[19] The PD-1/CD3 bispecific antibody or antibody fragment thereof according to any one of the preceding items [1] and [3] to [18], wherein the VH of the second arm specifically binding to CD3 comprises the amino acid sequence set forth in SEQ ID No. 36.

[20] The PD-1/CD3 bispecific antibody or antibody fragment thereof according to the preceding item [1], wherein the VH of the first arm specifically binding to PD-1 comprises the amino acid sequence set forth in any one selected from SEQ ID No. 1, SEQ ID No. 2, SEQ ID No. 3, SEQ ID No. 4, and SEQ ID No. 5; and the VH of the second arm specifically binding to CD3 comprises the amino acid sequence set forth in SEQ ID No. 36.

[21] A PD-1/CD3 bispecific antibody or antibody fragment thereof, having the first arm specifically binding to PD-1 and the second arm specifically binding to CD3, wherein the VH of the first arm specifically binding to PD-1 comprises the amino acid sequence set forth in any one selected from SEQ ID No. 1, SEQ ID No. 2, SEQ ID No. 3, SEQ ID No. 4, and SEQ ID No. 5, or an amino acid sequence having an identity of at least 80%, 90%, 95%, 98% or 99% to amino acid sequence thereof; and wherein the VH of the second arm specifically binding to CD3 comprises the amino acid sequence set forth in SEQ ID No. 36 or an amino acid having an identity of at least 80%, 90%, 95%, 98% or 99% to amino acid sequence thereof.

[22] The PD-1/CD3 bispecific antibody or antibody fragment thereof according to the preceding item [1] or [3], wherein the VH of the first arm specifically binding to PD-1 comprises the amino acid sequence set forth in SEQ ID No. 1; and wherein the VH of the second arm specifically binding to CD3 comprises the amino acid sequence set forth in SEQ ID No. 36.

[23] The PD-1/CD3 bispecific antibody or antibody fragment thereof according to the preceding item [1] or [4], wherein the VH of the first arm specifically binding to PD-1 comprises the amino acid sequence set forth in SEQ ID No. 2; and wherein the VH of the second arm specifically binding to CD3 comprises the amino acid sequence set forth in SEQ ID No. 36.

[24] The PD-1/CD3 bispecific antibody or antibody fragment thereof according to the preceding item [1] or [5], wherein the VH of the first arm specifically binding to PD-1 comprises the amino acid sequence set forth in SEQ ID No. 3; and wherein the VH of the second arm specifically binding to CD3 comprises the amino acid sequence set forth in SEQ ID No. 36.

[25] The PD-1/CD3 bispecific antibody or an antibody fragment thereof according to the preceding item [1] or [6], wherein the VH of the first arm specifically binding to PD-1 comprises the amino acid sequence set forth in SEQ ID No. 4; and wherein the VH of the second arm specifically binding to CD3 comprises the amino acid sequence set forth in SEQ ID No. 36.

[26] The PD-1/CD3 bispecific antibody or antibody fragment thereof according to the preceding item [1] or [7], wherein the VH of the first arm specifically binding to PD-1 comprises the amino acid sequence set forth in SEQ ID No. 5; and wherein the VH of the second arm specifically binding to CD3 comprises the amino acid sequence set forth in SEQ ID No. 36.

[27] The PD-1/CD3 bispecific antibody or antibody fragment thereof according to any one of the preceding items [1] to [26], wherein the first arm specifically binding to PD-1 and/or the second arm specifically binding to CD3 has a light chain variable region (hereinafter, "light chain variable region" may be abbreviated as "VL") having (a) a complementary determining region 1 of light chain variable region (hereinafter, the "complementary determining region 1 of light chain variable region" may be abbreviated as "VL-CDR1") comprising an amino acid sequence set forth in SEQ ID No. 26;

(b) a complementary determining region 2 of light chain variable region (hereinafter, the "complementary determining region 2 of light chain variable region" may be abbreviated as "VL-CDR2") comprising an amino acid sequence set forth in SEQ ID No. 27; and (c) a complementary determining region 3 of light chain variable region (hereinafter, the "complementary determining region 3 of light chain variable region" may be abbreviated as "VL-CDR3") comprising an amino acid sequence set forth in SEQ ID No. 28, respectively.

[28] The PD-1/CD3 bispecific antibody or antibody fragment thereof according to any one of the preceding items [1] to [27], wherein the first arm specifically binding to PD-1 and/or the second arm specifically binding to CD3 have the VL comprising an amino acid sequence set forth in SEQ ID No. 25, respectively.

[29] A PD-1/CD3 bispecific antibody or antibody fragment thereof, having the first arm specifically binding to PD-1 and the second arm specifically binding to CD3, wherein (A) the first arm specifically binding to PD-1 has the VH comprising the amino acid sequence set forth in any one selected from SEQ ID No. 1, SEQ ID No. 2, SEQ ID No. 3, SEQ ID No. 4, and SEQ ID No. 5, and the VL comprising the amino acid sequence set forth in SEQ ID No. 25; and (B) the second arm specifically binding to CD3 has the VH comprising the amino acid sequence set forth in SEQ ID No. 36; and the VL comprising the amino acid sequence set forth in SEQ ID No. 25.

[30] A PD-1/CD3 bispecific antibody or antibody fragment thereof, having the first arm specifically binding to PD-1 and the second arm specifically binding to CD3, wherein the first arm specifically binding to PD-1 cross-competes for (1) the binding to PD-1 with the first arm specifically binding to PD-1 having a VH comprising the amino acid sequence set forth in any one selected from SEQ ID No. 1, SEQ ID No. 2, SEQ ID No. 3, SEQ ID No. 4, and SEQ ID No. 5; and the VL comprising the amino acid of SEQ ID No. 25, or (2) the binding to PD-1 with a variable region of a monoclonal antibody specifically binding to PD-1 having the same VH and VL.

[31] A PD-1/CD3 bispecific antibody or antibody fragment thereof, having the first arm specifically binding to PD-1 and the second arm specifically binding to CD3, wherein the binding to PD-1 with the first arm specifically binding to PD-1 is cross-competed (1) by the first arm specifically binding to PD-1 having an VH comprising the amino acid sequence set forth in any one selected from SEQ ID No. 1, SEQ ID No. 2, SEQ ID No. 3, SEQ ID No. 4, and SEQ ID No. 5; and the VL comprising the amino acid of SEQ ID No. 25, or (2) by a variable region of a monoclonal antibody specifically binding to PD-1 having the same VH and VL.

[32] The PD-1/CD3 bispecific antibody or antibody fragment thereof according to item [30] or [31], wherein the second arm specifically binding to CD3 further cross-competes for (1) the binding to CD3 with the second arm specifically binding to CD3 having the VH comprising the amino acid sequence set forth SEQ ID No. 36; and the VL comprising the amino acid sequence set forth in SEQ ID No. 25, or (2) the binding to CD3 with a variable region of a monoclonal antibody specifically binding to CD3 having the same VH and VL.

[33] The PD-1/CD3 bispecific antibody or antibody fragment thereof according to item [30] or [31], wherein the second arm specifically binding to CD3 contains a VH having:
(a) the VH-CDR1 comprising the amino acid sequence set forth in SEQ ID No.37;
(b) the VH-CDR2 comprising the amino acid sequence set forth in SEQ ID No.38; and
(c) the VH-CDR3 comprising the amino acid sequence set forth in SEQ ID No.39.

[34] The PD-1/CD3 bispecific antibody or antibody fragment thereof according to any one of items [30], [31] and [33], wherein the VH in the second arm specifically binding to CD3 comprises the amino acid sequence set forth in SEQ ID No. 36 or the amino acid sequence having an identity of at least 80%, 90%, 95%, 98% or 99% to amino acid sequence thereof.

[35] The PD-1/CD3 bispecific antibody or antibody fragment thereof according to item [30] or [31], wherein the VH of the second arm specifically binding to CD3 comprises the amino acid sequence set forth in SEQ ID No. 36.

[36] The PD-1/CD3 bispecific antibody or antibody fragment thereof according to any one of items [30], [31], and [33] to [35], wherein the second arm specifically binding to CD3 has the VL having:
(a) the VL-CDR1 comprising the amino acid sequence set forth in SEQ ID No. 26;
(b) the VL-CDR2 comprising the amino acid sequence set forth in SEQ ID No. 27; and
(c) the VL-CDR3 comprising the amino acid sequence set forth in SEQ ID No. 28.

[37] The PD-1/CD3 bispecific antibody or antibody fragment thereof according to any one of items [30], [31], and [33] to [35], wherein the second arm specifically binding to CD3 has the VL comprising the amino acid sequence set forth in SEQ ID No. 25.

[38] The PD-1/CD3 bispecific antibody or antibody fragment thereof according to any one of the preceding items [1] to [37], wherein the PD-1/CD3 bispecific antibody is an IgG antibody.

[39] The PD-1/CD3 bispecific antibody or antibody fragment thereof according to the preceding item [38], wherein the IgG antibody in the preceding item [38] is an $IgG_1$ or $IgG_4$ antibody.

[40] The PD-1/CD3 bispecific antibody or antibody fragment thereof according to the preceding item [38], wherein the IgG antibody in the preceding item [38] is an $IgG_1$ antibody.

[41] The PD-1/CD3 bispecific antibody or antibody fragment thereof according to the preceding item [38], wherein the IgG antibody in the preceding item [38] is an $IgG_4$ antibody.

[42] The PD-1/CD3 bispecific antibody or antibody fragment thereof according to the preceding item [40], wherein in two heavy chain constant regions of the $IgG_1$ antibody in the preceding item [40], leucines at position 235 according to the EU numbering system are substituted with glycine and/or glycines at position 236 according to the EU numbering system are substituted with arginine, respectively.

[43] The PD-1/CD3 bispecific antibody or antibody fragment thereof according to the preceding item [40] or [42], wherein in a constant region of heavy chain having the VH of the first arm specifically binding to PD-1, both of leucine at position 351 according to the EU numbering system and threonine at position 366 according to the EU numbering system are substituted with lysine, and in a constant region of heavy chain having the VH of the second arm specifically binding to CD3, leucine at position 351 according to the EU numbering system is substituted with aspartic acid and leucine at position 368 according to the EU numbering system is substituted with glutamic acid.

[44] The PD-1/CD3 bispecific antibody or antibody fragment thereof according to the preceding item [40] or [42], wherein in a constant region of heavy chain having the VH of the first arm specifically binding to PD-1, leucine at position 351 according to the EU numbering system is substituted with aspartic acid and leucine at position 368 according to the EU numbering system is substituted with glutamic acid, and in a constant region of heavy chain having the VH of the second arm specifically binding to CD3, both of leucine at position 351 according to the EU numbering system and threonine at position 366 according to the EU numbering system are substituted with lysine.

[45] The PD-1/CD3 bispecific antibody or antibody fragment thereof according to any one of the preceding items [40] and [42] to [44], wherein in two heavy chain constant regions of the $IgG_1$ antibody in any one of the preceding items [40] and [42] to [44], each lysine at position 447 according to the EU numbering system is deleted.

[46] The PD-1/CD3 bispecific antibody or antibody fragment thereof according to the preceding item [41], wherein in two heavy chain constant regions of the $IgG_4$ antibody in the preceding item [41], serines at position 228 according to the EU numbering system are substituted with proline, respectively.

[47] The PD-1/CD3 bispecific antibody or antibody fragment thereof according to any one of the preceding items [1] to [38], [40], [42] and [44], wherein the heavy chain having the VH of the first arm specifically binding to PD-1 has a heavy chain constant region comprising an amino acid sequence set forth in SEQ ID No. 23.

[48] The PD-1/CD3 bispecific antibody or antibody fragment thereof according to any one of the preceding items [1] to [38], [40], [42], [44] and [47], wherein the heavy chain having the VH of the second arm specifically binding to CD3 has a heavy chain constant region comprising an amino acid sequence set forth in SEQ ID No. 24.

[49] The PD-1/CD3 bispecific antibody or antibody fragment thereof according to any one of the preceding items [1] to [48], wherein the light chain having the VL of the first arm specifically binding to PD-1 and/or the light chain having VL of the second arm specifically binding to CD3 has/have a light chain constant region comprising an amino acid sequence set forth in SEQ ID No. 29.

[50] A PD-1/CD3 bispecific antibody or antibody fragment thereof, having the first arm specifically binding to PD-1 and the second arm specifically binding to CD3, wherein:
(A) a heavy chain having the VH of the first arm specifically binding to PD-1 has the VH comprising the amino acid sequence set forth in any one selected from SEQ ID No. 1, SEQ ID No. 2, SEQ ID No. 3, SEQ ID No. 4, and SEQ ID No. 5, and the heavy chain constant region comprising the amino acid sequence set forth in SEQ ID No. 23;
(B) a light chain having the VL of the first arm specifically binding to PD-1 has the VL comprising the amino acid sequence set forth in SEQ ID No. 25, and the light chain constant region comprising the amino acid sequence set forth in SEQ ID No. 29;
(C) a heavy chain having the VH of the second arm specifically binding to CD3, has the VH comprising the amino acid sequence set forth in SEQ ID No. 36, and the heavy chain constant region comprising the amino acid sequence set forth in SEQ ID No. 24; and
(D) a light chain having the VL of the second arm specifically binding to CD3 has the VL comprising the amino acid sequence set forth in SEQ ID No. 25, and the light chain constant region comprising the amino acid sequence set forth in SEQ ID No. 29.

[51] The PD-1/CD3 bispecific antibody or antibody fragment thereof according to any one of the preceding items [1] to [50], wherein the first arm specifically binding to PD-1 allows an interaction between PD-1 and PD-L1.

[52] The PD-1/CD3 bispecific antibody or antibody fragment thereof according to any one of the preceding items [1] to [51], wherein cytokine production is sufficiently reduced.

[53] The PD-1/CD3 bispecific antibody or antibody fragment thereof according to any one of the preceding items [1] to [50], wherein the first arm specifically binding to PD-1 allows the interaction between the PD-1 and PD-L1, and wherein cytokine production is sufficiently reduced.

[54] The PD-1/CD3 bispecific antibody or antibody fragment thereof according to the preceding item [52] or [53], wherein the cytokine includes at least IL-2, IFN-γ or TNF-α.

[55] The PD-1/CD3 bispecific antibody or antibody fragment thereof according to any one of the preceding items [1] to [54], wherein PD-1 is human PD-1, and CD3 is human CD3, respectively.

[56] The PD-1/CD3 bispecific antibody or antibody fragment thereof according to any one of the preceding items [1] to [55], wherein CD3 is CD3ε.

[57] The PD-1/CD3 bispecific antibody or antibody fragment thereof according to any one of the preceding items [1] to [56], wherein the PD-1/CD3 bispecific antibody is a monoclonal antibody.

[58] The PD-1/CD3 bispecific antibody or antibody fragment thereof according to any one of the preceding items [1] to [57], wherein the PD-1/CD3 bispecific antibody is an isolated antibody.

[1-1] A pharmaceutical composition including the PD-1/CD3 bispecific antibody or antibody fragment thereof according to any one of the preceding items [1] to [58] and a pharmaceutically acceptable carrier.

[2-1] A pharmaceutical agent for preventing, suppressing symptom progression or recurrence of, and/or treating autoimmune disease, containing the PD-1/CD3 bispecific antibody or antibody fragment thereof according to any one of the preceding items [1] to [58] as an active ingredient.

[2-2] The pharmaceutical agent according to the preceding item [2-1], wherein the autoimmune disease includes Behcet's disease, systemic lupus erythematosus, chronic discoid lupus erythematosus, multiple sclerosis (systemic scleroderma, and progressive systemic sclerosis), scleroderma, polymyositis, dermatomyositis, periarteritis nodosa (polyarteritis nodosa, and microscopic polyangiitis), aortitis syndrome (Takayasu's arteritis), malignant rheumatoid arthritis, rheumatoid arthritis, juvenile idiopathic arthritis, spondyloarthritis, mixed connective tissue disease, Sjogren's syndrome, adult Still's disease, vasculitis, allergic granulomatous vasculitis, hypersensitivity vasculitis, rheumatoid vasculitis, large vessel vasculitis, ANCA associated vasculitis (e.g., granulomatosis with polyangiitis and eosinophilic granulomatosis with polyangiitis), Cogan's syndrome, RS3PE, temporal arteritis, polymyalgia rheumatica, fibromyalgia, antiphospholipid antibody syndrome, eosinophilic fasciitis, IgG4-related disease (e.g., primary sclerosing cholangitis, autoimmune insulitis), Guillain-Barre syndrome, myasthenia gravis, chronic atrophic gastritis, autoimmune hepatitis, non-alcoholic steatohepatitis, primary biliary cirrhosis, Goodpasture's syndrome, rapidly progressive glomerulonephritis, megaloblastic anemia, autoimmune hemolytic anemia, pernicious anemia, autoimmune neutropenia, idiopathic thrombocytopenic purpura, Basedow disease (Graves' disease (hyperthyroidism)), Hashimoto disease, autoimmune adrenal insufficiency, primary hypothyroidism, Addison's disease (chronic hypoadrenocorticism), idiopathic Addison's disease, type I diabetes mellitus, slowly progressive type I diabetes mellitus (latent autoimmune diabetes in adult), focal scleroderma, psoriasis, psoriatic arthritis, bullous pemphigoid, pemphigus, pemphigoid, gestational herpes, linear IgA bullous dermatosis, acquired epidermolysis bullosa, alopecia areata, vitiligo, vitiligo vulgaris, neuromyelitis optica, chronic inflammatory demyelinating polyneuropathy, multifocal motor neuropathy, sarcoidosis, giant cell arteritis, amyotrophic lateral sclerosis, Harada disease, autoimmune optic neuropathy, idiopathic azoospermia, habitual abortion, inflammatory bowel disease (e.g., ulcerous colitis, and Crohn's disease), celiac disease, ankylosing spondylitis, severe asthma, chronic urticarial, transplantation immunity, familial mediterranean fever, eosinophilic chronic rhinosinusitis, dilated cardiomyopathy, systemic mastocytosis, or inclusion body myositis.

[2-3] A pharmaceutical agent for preventing, suppressing symptom progression or recurrence of, and/or treating graft-versus-host disease (GVHD), containing the PD-1/CD3 bispecific antibody or antibody fragment thereof according to any one of the preceding items [1] to [58] as an active ingredient.

[2-4] A pharmaceutical agent for preventing, suppressing symptom progression or recurrence of, and/or treating type I diabetes mellitus, containing the PD-1/CD3 bispecific antibody or antibody fragment thereof according to any one of the preceding items [1] to [58] as an active ingredient, and being administered together with any one or more selected from an insulin formulation (e.g., human insulin, insulin glargine, insulin lispro, insulin detemir, insulin aspart, and the like.), sulfonylurea agent (e.g., glibenclamide, gliclazide, or glimepiride), quick-acting insulin secretion promoter (e.g., nateglinide), biguanide preparation (e.g., metformin), insulin resistance improving agent (e.g., pioglitazone), α-glucosidase inhibitor (e.g., acarbose, voglibose, and the like.), diabetic neuropathy therapeutic agent (e.g., epalrestat, mexiletine, imidapril, and the like.), GLP-1 analog preparation (e.g., liraglutide, exenatide, lixisenatide, and the like.), and DPP-4 inhibitor (e.g., sitagliptin, vildagliptin, alogliptin, and the like.).

[2-5] A pharmaceutical agent for preventing, suppressing symptom progression or recurrence of, and/or treating multiple sclerosis, containing the PD-1/CD3 bispecific antibody or antibody fragment thereof according to any one of the preceding items [1] to [58] as an active ingredient, and being administered together with any one or more selected from a steroid agent (e.g., cortisone acetate, hydrocortisone, hydrocortisone sodium phosphate, hydrocortisone sodium succinate, fludrocortisone acetate, prednisolone, prednisolone acetate, prednisolone sodium succinate, prednisolone butylacetate, prednisolone sodium phosphate, halopredone acetate, methylprednisolone, methylprednisolone acetate, methylprednisolone sodium succinate, triamsinolone, triamsinolone acetate, triamsinolone acetonide, dexamethasone, dexamethasone acetate, dexamethasone sodium phosphate, dexamethasone palmitate, paramethasone acetate, or betamethasone and the like.), interferon β-1a, interferon β-1b, glatiramer acetate, mitoxantrone, azathioprine, cyclophosphamide, cyclosporin, methotrexate, cladribine, adrenocorticotropic hormone (ACTH), corticotropin, mizoribine, tacrolimus, fingolimod, and alemtuzumab.

[2-6] A pharmaceutical agent for preventing, suppressing symptom progression or recurrence of, and/or treating systemic lupus erythematosus, containing the PD-1/CD3 bispecific antibody or antibody fragment thereof according to any one of the preceding items [1] to [58] as an active ingredient, and being administered together with any one or more selected from a steroid agent (e.g., the steroid agents mentioned in the preceding item [2-5]), an immunosuppressive agent (e.g., cyclosporin, tacrolimus, or fingolimod), and belimumab.

[2-7] A pharmaceutical agent for preventing, suppressing symptom progression or recurrence of, and/or treating rheumatoid arthritis, containing the PD-1/CD3 bispecific antibody or antibody fragment thereof according to any one of the preceding items [1] to [58] as an active ingredient, and being administered together with any one or more selected from a steroid agent (e.g., the steroid agents mentioned in the preceding item [2-5]), anti-rheumatic agent (e.g., methotrexate, sulfasalazine, bucillamine, leflunomide, mizoribine, tacrolimus, and the like.), anti-cytokine agent (e.g., infliximab, adalimumab, tocilizumab, etanercept, golimumab, sertolizumab.), and abatacept.

[2-8] A pharmaceutical agent for preventing, suppressing symptom progression or recurrence of, and/or treating autoimmune disease, containing the PD-1/CD3 bispecific antibody or antibody fragment thereof according to any one of the preceding items [1] to [58] as an active ingredient, and being administered together with any one or more of agents described in the preceding items [2-4] to [2-7].

[2-9] A pharmaceutical agent for preventing, suppressing symptom progression or recurrence of, and/or treating diseases mentioned in the preceding items [2-4] to [2-8], being administered to the patient whom any one or more of drugs mentioned in the preceding items [2-4] to [2-7] is/are administered.

[2-10] A pharmaceutical agent for preventing, suppressing symptom progression or recurrence of, and/or treating diseases mentioned in the preceding items [2-4] to [2-8], being administered after administration of any one or more of drugs mentioned in the preceding items [2-4] to [2-7].

[2-11] A pharmaceutical agent for preventing, suppressing symptom progression or recurrence of, and/or treating diseases mentioned in the preceding items [2-4] to [2-8], being administered before administration of any one or more of drugs mentioned in the preceding items [2-4] to [2-7].

[3-1] An intravenous injection formulation including the PD-1/CD3 bispecific antibody or antibody fragment thereof according to any one of the preceding items [1] to [58] and a pharmaceutically acceptable carrier.

[3-2] The intravenous injection formulation according to the above-mentioned [3-1] for use in prophylaxis, suppression of progress of symptoms, suppression of recurrence and/or therapy for autoimmune disease.

[3-3] The intravenous injection formulation according to the preceding item [3-1] or [3-2] for use in drip infusion.

[4-1] An isolated polynucleotide or fragment thereof encoding a heavy chain having a VH of the first arm specifically binding to PD-1 constituting any one of PD-1/CD3 bispecific antibody selected from the preceding items [1] to [58].

[4-2] An isolated polynucleotide or fragment thereof encoding a VH of the first arm specifically binding to PD-1 constituting any one of PD-1/CD3 bispecific antibody selected from the preceding items [1] to [58].

[4-3] The isolated polynucleotide or fragment thereof according to the preceding items [4-1] or [4-2], wherein the VH of the first arm specifically binding to PD-1 is encoded by a polynucleotide comprising a sequence set forth in any one selected from SEQ ID Nos. 30 to 34.

[4-4] An isolated polynucleotide or a fragment thereof having a polynucleotide comprising a sequence set forth in any one selected from SEQ ID Nos. 30 to 34.

[5-1] An expression vector having a polynucleotide according to any of the preceding items [4-1] to [4-4].

[6-1] An animal cell, into which the expression vector of the preceding item [5-1] is transfected, or which is transformed by the transfected vector.

[7-1] A method for preventing, suppressing symptom progression or recurrence of, and/or treating autoimmune disease, comprising administering an effective amount of the PD-1/CD3 bispecific antibody or antibody fragment thereof according to any one of the preceding items [1] to [58] to a patient.

[8-1] A PD-1/CD3 bispecific antibody or antibody fragment thereof selected from the preceding items [1] to [58] in use for preventing, suppressing symptom progression or recurrence of, and/or treating autoimmune disease.

[9-1] Use of the PD-1/CD3 bispecific antibody or antibody fragment thereof selected from the preceding items [1] to [58] for manufacturing a pharmaceutical for preventing, suppressing symptom progression or recurrence of, and/or treating autoimmune disease.

[10-1] An isolated anti-PD-1 monoclonal antibody or antibody fragment thereof, which cross-competes for binding to PD-1 with an antibody specifically binding to PD-1 having the VH comprising the amino acid sequence set forth in any one selected from SEQ ID No. 1, SEQ ID No. 2, SEQ ID No. 3, SEQ ID No. 4, and SEQ ID No. 5, and the VL comprising the amino acid sequence of SEQ ID No. 25.

[10-2] An isolated anti-PD-1 monoclonal antibody or an antibody fragment thereof, wherein the binding to PD-1 with the isolated anti-PD-1 monoclonal antibody or antibody fragment thereof is cross-competed by an antibody specifically binding to PD-1 having the VH comprising the amino acid sequence set forth in any one selected from SEQ ID No. 1, SEQ ID No. 2, SEQ ID No. 3, SEQ ID No. 4, and SEQ ID No. 5, and the VL comprising the amino acid sequence of SEQ ID No. 25.

[10-3] An isolated anti-PD-1 monoclonal antibody or antibody fragment thereof, having any one of VH selected from:
(A) the VH having:
 (a) the VH-CDR1 comprising the amino acid sequence set forth in SEQ ID No. 6,
 (b) the VH-CDR2 comprising the amino acid sequence set forth in SEQ ID No. 7, and
 (c) the VH-CDR3 comprising the amino acid sequence set forth in SEQ ID No. 8,
(B) the VH having:
 (a) the VH-CDR1 comprising the amino acid sequence set forth in SEQ ID No. 9,
 (b) the VH-CDR2 comprising the amino acid sequence set forth in SEQ ID No. 10, and
 (c) the VH-CDR3 comprising the amino acid sequence set forth in SEQ ID No. 11,
(C) the VH having:
 (a) the VH-CDR1 comprising the amino acid sequence set forth in SEQ ID No. 12,
 (b) the VH-CDR2 comprising the amino acid sequence set forth in SEQ ID No. 13, and
 (c) the VH-CDR3 comprising the amino acid sequence set forth in SEQ ID No. 14,
(D) the VH having:
 (a) the VH-CDR1 comprising the amino acid sequence set forth in SEQ ID No. 15,
 (b) the VH-CDR2 comprising the amino acid sequence set forth in SEQ ID No. 16, and
 (c) the VH-CDR3 comprising the amino acid sequence set forth in SEQ ID No. 17, and
(E) the VH having:
 (a) the VH-CDR1 comprising the amino acid sequence set forth in SEQ ID No. 18,
 (b) the VH-CDR2 comprising the amino acid sequence set forth in SEQ ID No. 19, and
 (c) the VH-CDR3 comprising the amino acid sequence set forth in SEQ ID No. 20, and the
VL having:
 (a) the VL-CDR1 comprising the amino acid sequence set forth in SEQ ID No. 26,
 (b) the VL-CDR2 comprising the amino acid sequence set forth in SEQ ID No. 27, and
 (c) the VL-CDR3 comprising the amino acid sequence set forth in SEQ ID No. 28.

[10-4] The isolated anti-PD-1 monoclonal antibody or antibody fragment thereof according to the preceding item [10-3], wherein one to five arbitrary amino acid residue(s) in any one or more of the CDR(s) selected from the VH-CDR1, VH-CDR2 and VH-CDR3 may be substituted with other amino acid(s) (preferably, conservative amino acid(s) thereof).

[10-5] The isolated anti-PD-1 monoclonal antibody or antibody fragment thereof according to the preceding item [10-3] or [10-4], having the VH comprising the amino acid sequence set forth in any one selected from SEQ ID No. 1, SEQ ID No. 2, SEQ ID No. 3, SEQ ID No. 4, and SEQ ID No. 5, or the VH comprising the amino acid sequence having at least 80%, 90%, 95%, 98% or 99% identity of amino acid sequence thereof, and the VL comprising the amino acid sequence set forth in SEQ ID No. 25.

[10-6] The isolated anti-PD-1 monoclonal antibody or antibody fragment thereof according to any one of the preceding items [10-1] to [10-5], wherein the PD-1 is human PD-1.

[10-7] The isolated anti-PD-1 monoclonal antibody or antibody fragment thereof according to any one of the preceding items [10-1] to [10-6], wherein the anti-PD-1 antibody is an IgG antibody.

[10-8] The isolated anti-PD-1 monoclonal antibody or antibody fragment thereof according to the preceding item [10-7], wherein the IgG antibody described in the preceding item [10-7] is an $IgG_1$ antibody or $IgG_4$ antibody.

[10-9] The isolated anti-PD-1 monoclonal antibody or antibody fragment thereof according to the preceding item [10-7], wherein the IgG antibody described in the preceding item [10-7] is an $IgG_1$ antibody.

[10-10] The isolated anti-PD-1 monoclonal antibody or antibody fragment thereof according to the preceding item [10-7], wherein the IgG antibody described in the preceding item [10-7] is an $IgG_4$ antibody.

Effects of Invention

Since the inducibility of cytokine production of the PD-1/CD3 bispecific antibody of the present invention is reduced, the occurrence of infusion reaction or cytokine release syndrome after administration is suppressed. Furthermore, the PD-1/CD3 bispecific antibody allows interaction between the PD-1 and PD-L1, and is expected to enhance or sustain the effect on prevention, suppression of symptom progression or recurrence of, and/or therapy for autoimmune disease.

BRIEF DESCRIPTION OF THE DRAWINGS

FIG. 1 shows each amino acid sequence of VL and constant region of common light chain.

FIG. 2 shows each CDR amino acid sequence in the VL of common light chain.

FIG. 3 shows the amino acid sequences encoded by germ-line V genes: IGHV7-4-1 and IGHV3-33, respectively.

FIG. 4 shows a sequence alignment among the VH of each clone of antibodies specifically binding to PD-1 (hereinafter, which may be abbreviated as "anti-PD-1 antibody") and germ-line genes IGHV7-4-1 and JH6c. In the drawing, in the amino acid sequence of each clone, "—" represents the same amino acid as that of the corresponding germ-line gene IGHV7-4-1 or JH6c, and a part with simplified characters of each amino acid represents an amino acid different from that of the germ-line gene.

FIG. 5 shows the VH amino acid sequence of each anti-PD-1 antibody clone.

FIG. 6 shows each CDR amino acid sequence in VH of each anti-PD-1 antibody clone.

FIG. 7 shows the VH amino acid sequence of the CD3-2 clone as an antibody specifically binding to CD3 (hereinafter, which may be abbreviated as "anti-CD3 antibody").

FIG. 8 shows the amino acid sequence of each CDR in the VH of the CD3-2 clone as an anti-CD3 antibody.

FIG. 9 shows the amino acid sequence of constant region in each heavy chain of the PD-1/CD3 bispecific monoclonal antibody.

FIG. 10 shows the VH amino acid sequence of the anti-CD3 antibody clone 15C3 described in WO2005/118635. Note here that the underlined amino acid represents the 55th glycine which is converted into alanine in producing the clone CD3-1.

FIG. 11 shows Biacore measurement results demonstrating the binding activity to PD-1 and CD3 of each PD-1/CD3 bispecific monoclonal antibody clone.

DESCRIPTION OF EMBODIMENTS

Figure 12:
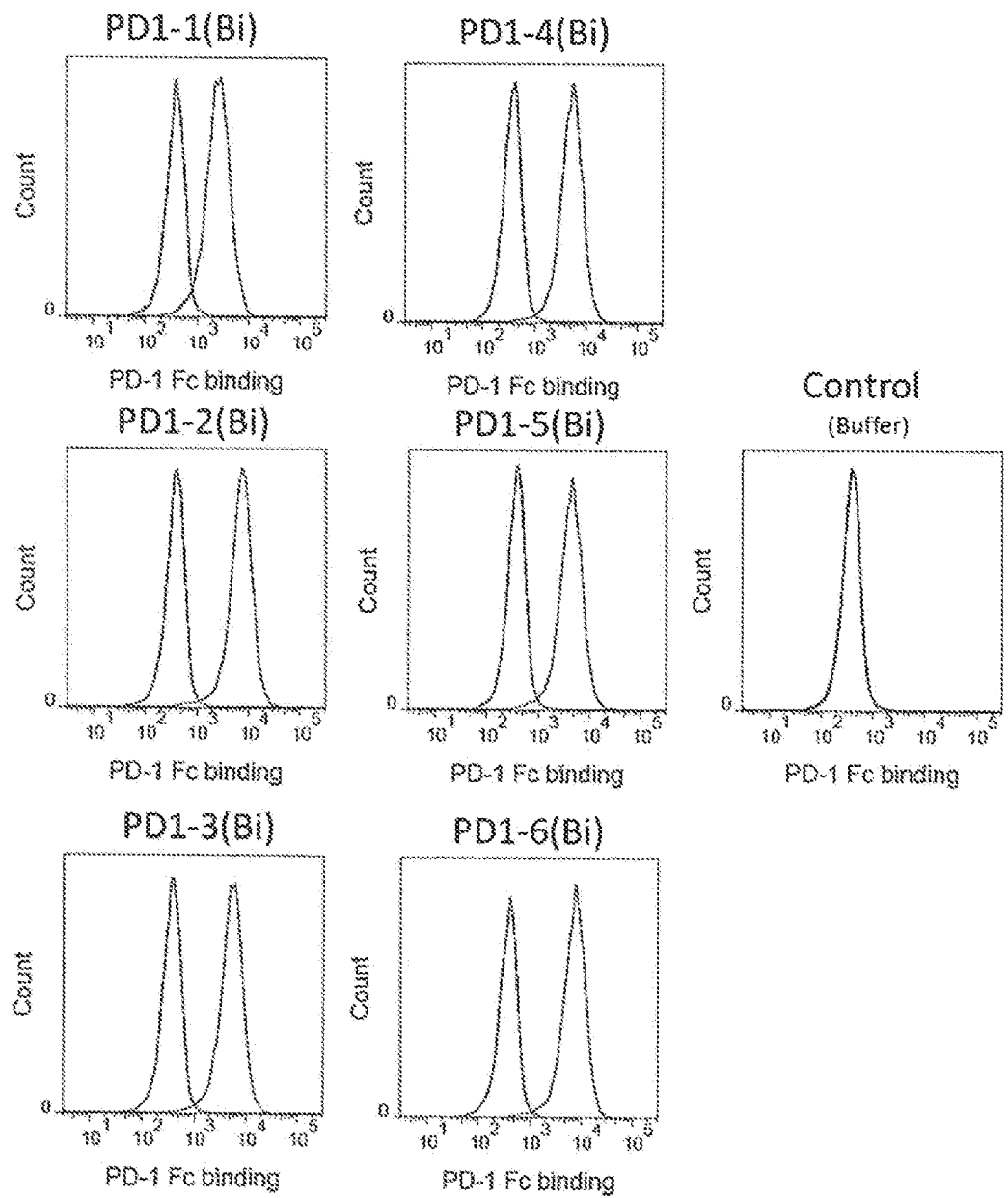
FIG. 12 shows flow cytometry demonstrating the simultaneous binding property to PD-1 and CD3 of each PD-1/CD3 bispecific monoclonal antibody clone.

PD-1 (Programmed Cell Death-1) in human is a membrane-type protein composed of the amino acid sequence represented by GenBank accession number NP_005009. In the present specification, the term "PD-1", unless specifically defined otherwise, may be used as a meaning including all the isoforms thereof, and variants thereof in which epitopes for the "first arm specifically binding to PD-1" in the present inventions are conserved. In the present invention, PD-1 is preferably human PD-1.

CD3 is the membrane-type protein which forms T-cell receptor complex by association with a T-cell receptor. In the present specification, the term "CD3", unless specifically defined otherwise, may be used as a meaning including the subtype (ε, δ, γ and ζ subtype), and variants thereof in which epitopes for the "second arm specifically binding to CD3" of the present inventions are conserved. In the present invention, CD3 is preferably CD3ε, and human CD3, and more preferably human CD3ε.

In the present specification, the term "isolate" means that a single substantially pure component is obtained by being identified, separated and/or purified from impurities containing a plurality of or myriad number of components extracted from a host cell.

In the present specification, the term "monoclonal antibody" means an antibody obtained from a substantially homogeneous antibody group binding to the same specific antigen.

In this specification, the term "bispecific antibody" means an antibody having binding specificity to two different antigen molecules or epitopes in a molecule. Furthermore, the term "bispecific monoclonal antibody" means a bispecific antibody obtained from a substantially homogeneous antibody group.

The present invention relates to a bispecific antibody capable of specifically binding to PD-1 and CD3 (in the present specification, may be abbreviated as "PD-1/CD3 bispecific antibody"). In the present invention, the PD-1/CD3 bispecific antibody is preferably a PD-1/CD3 bispecific monoclonal antibody, and more preferably an isolated PD-1/CD3 bispecific monoclonal antibody, and further preferably an isolated human PD-1/human CD3 bispecific monoclonal antibody. Herein, the "isolated human PD-1/human CD3 bispecific monoclonal antibody" means an isolated bispecific monoclonal antibody for human PD-1 and human CD3.

Exemplified embodiments of the PD-1 bispecific antibody include, e.g., diabodies, bispecific sc(Fv)$_2$, bispecific minibodies, bispecific F(ab')$_2$, bispecific hybrid antibodies, covalent diabodies (bispecific DART), bispecific (FvCys)$_2$, bispecific F(ab'-zipper)$_2$, bispecific (Fv-zipper)$_2$, bispecific three-chain antibodies, and bispecific mAb$^2$, and the like.

The diabody is a dimer of single-chain peptides in which a VH and VL recognizing different antigens are linked to each other with a peptide linker (Proc. Natl. Acad. Sci. USA, 1993, Vol. 90, No. 14, pp. 6444-6448).

The bispecific sc(Fv)$_2$ is a low-molecular antibody modified such that two pairs of VH/VL in two antibodies recognizing different antigens are linked to each other with a peptide linker into a continuous single chain form (see J. Biological Chemistry, 1994, 269: pp. 199-206).

The bispecific F(ab')$_2$ is a low-molecular antibody in which Fab' fragments of antibodies recognizing two different antigens are covalently bonded through, e.g., a disulfide bond.

The bispecific minibody is a low-molecular antibody in which low-molecular antibody fragments modified in such a manner that the constant region CH3 domains of the antibodies are linked to scFv recognizing different antigens is covalently bonded by, e.g., the disulfide bonds on the CH3 domains (see Biochemistry, 1992, Vo. 31, No 0.6, pp. 1579-1584).

The bispecific hybrid antibody is an intact antibody in which heavy chain/light chain complexes recognizing two different antigens are covalently bound each other by, e.g., a disulfide bond.

In the present invention, examples of the form of the preferable bispecific antibody include a bispecific hybrid antibody.

The bispecific hybrid antibody can be produced, e.g., from a hybridoma using a hybrid hybridoma method (see U.S. Pat. No. 4,474,893). Alternatively, the bispecific hybrid antibody can be produced by secretion from a mammal animal cell co-expressing four kinds of cDNAs respectively encoding heavy chain and light chain of antibodies recognizing different antigens.

The monoclonal antibodies used in the present invention can be produced by a hybridoma method (see, e.g., Kohler and Milstein et al., Natur (1975), Vol. 256, p. 495-9'7, Hongo et al., Hybridoma (1995), Vol. 14, No. 3, pp. 253-260, Harlow et al., Antibodies: A Laboratory Manual, (Cold Spring Harbor Laboratory Press (1988), Vol. 2) and Hammerling et al., Monoclonal Antibodies and T-Cell Hybridomas, pp. 563-681 (Elsevier, N.Y., 1981)), a recombinant DNA method (see, e.g., U.S. Pat. No. 4,816,567), a phage display method (see, e.g., Ladner et al., U.S. Pat. Nos. 5,223,409, 5,403,484 and 5,571,698, Dower et al., U.S. Pat. Nos. 5,427,908 and 5,580,717, McCafferty et al., U.S. Pat. Nos. 5,969,108 and 6,172,197, and Griffiths et al., U.S. Pat. Nos. 5,885,793, 6,521,404, 6,544,731, 6,555,313, 6,582,915 and 6,593,081).

An antibody or a monoclonal antibody, when being administered to human, can be produced in a form of a chimeric antibody, a humanized antibody, or a complete human antibody in order to reduce or eliminate its antigenicity.

The term "chimeric antibody" means the antibody of which the constant region sequence and variable region sequence are derived from different mammalian. Examples of the chimeric antibody include an antibody of which the variable region sequence is derived from a mouse antibody and the constant region sequence is derived from a human antibody. The chimeric antibody can be produced by linking a gene encoding an antibody variable region isolated from the above-mentioned antibody-producing hybridoma isolated by a hybridoma method, a recombinant DNA method or a phage display method by well-known techniques, to a gene encoding the constant region of a human-derived antibody using a well-known method (see, e.g., Cabilly et al., U.S. Pat. No. 4,816,567).

The term "humanized antibody" means an antibody prepared by, e.g., grafting a complementarily determining region (CDR) sequence of an antibody derived from a germ line of a mammal other than human, such as mouse, into human framework sequences of a human antibody. Also, the humanized antibody can be produced by linking genes encoding CDR regions of an antibody isolated from the above-mentioned antibody-producing hybridoma isolated by the above-mentioned method, to a gene encoding a framework region of the human-derived antibody using a well-known method (see, e.g., Winter, U.S. Pat. Nos. 5,225, 539 and 5,530,101; Queen et al., U.S. Pat. Nos. 5,585,089 and 6,180,370).

The term "human antibody" or "complete human antibody" means an antibody in which both of a variable region composed of framework regions and CDR regions and a constant region are derived from human germline immunoglobulin sequences. The human antibody to be used in the present invention can be produced by a method using a mouse transformed to produce human antibodies, e.g., Humab mouse (see, e.g., Lonberg and Kay et al. U.S. Pat. Nos. 5,545,806, 5,569,825, 5,625,126, 5,633,425, 5,789, 650, 5,877,397, 5,661,016, 5,814,318, 5,874,299 and 5,770, 429), a KM mouse (see, e.g., Ishida et al., WO2002/43478), a Xeno mouse (see, e.g., U.S. Pat. Nos. 5,939,598, 6,075, 181, 6,114,598, 6,150,584 and 6,162,963), or a Tc mouse (see, e.g., Tomizuka et al., Proc. Natl. Acad. Sci. USA (2000), pp. 722-727). The human antibody can also be prepared using SCID mice into which human immune cells have been reconstructed such that human antibody response is made upon immunization (see, e.g., U.S. Pat. Nos. 5,476, 996 and 5,698,767 to Wilson et al.). Furthermore, the human antibody used in the present invention can also be produced by the above-mentioned phage display method.

In the present specification, the term "antibody fragment" of the PD-1/CD3 bispecific antibody is a part of the full-length antibody and is an antibody having an antigen binding part to PD-1 and an antigen binding part to CD3. Examples thereof include $F(ab')_2$, and the like. Herein, the antigen binding part means a minimum unit of an antibody that can bind to an antigen thereof, and e.g., it is composed of three CDRs in each of VH and VL and framework regions for arranging CDRs such that the target antigen can be recognized by combination of those CDRs.

In the present specification, the term "common light chain" means a light chain that can be associated with two or more different heavy chains, and can exhibit the binding ability to each antigen (De Wildt R M, J. Mol. Biol. (1999), Vol. 285, pp. 895-901, De Kruif et al., J. Mol. Biol. (2009), Vol. 387, pp. 548-58, WO2004/009618, WO2009/157771 and WO2014/051433). Preferable examples of such a common light chain include a light chain encoded by human κ light chain IgVκ1-39*01/IGJκ1*01 (nomenclatures of IMGT database) germ-line gene (hereinafter, abbreviated as "IGVK1-39/JK1 common light chain"). More preferable examples include the light chain containing the VL having the CDR1 comprising the amino acid sequence set forth in SEQ ID No. 26, the CDR2 comprising the amino acid sequence set forth in SEQ ID No. 27, and the CDR3 comprising the amino acid sequence set forth in SEQ ID No. 28, and further preferable examples include the light chain containing the VL comprising the amino acid sequence set forth in SEQ ID No. 25. Furthermore, preferable examples of the constant region of the common light chain include the light chain constant region comprising the amino acid sequence set forth in SEQ ID No. 29. Each amino acid sequence of VL and the constant region of common light chain used in the present invention are shown in FIG. 1, and each CDR amino acid sequence of the variable region is shown in FIG. 2.

In the present specification, the term "isotype" means the antibody class (e.g., IgM or IgG) that is encoded by heavy chain constant region genes. Preferable examples of the isotype for the PD-1/CD3 bispecific antibody of the present invention include IgG, and more preferably, $IgG_1$ or $IgG_4$. The $IgG_1$ used herein is preferably of which the binding to an Fc receptor is eliminated or decreased. Specifically, the $IgG_1$ antibody of which the binding to the Fc receptor is eliminated or decreased can be obtained by substituting, deleting, or inserting arbitrary amino acid of the heavy chain constant region thereof. Examples thereof include an antibody in which leucine at position 235 according to the EU numbering system is substituted with glycine, and/or glycine at position 236 according to the EU numbering system is substituted with arginine on each of two heavy chain constant regions or a hinge region thereof. Furthermore, in order to reduce the heterogeneity of the antibody, the antibody in which an amino acid at C-terminal, e.g., lysine at position 447 according to the EU numbering system has been deleted is preferable. Furthermore, when the bispecific antibody is IgG4, in order to suppress the swapping in an antibody molecule, the variant in which an arbitrary amino acid in the heavy chain constant region thereof is substituted, deleted or inserted is preferable. For example, an antibody of which serine located in the hinge region and at position 228 according to the EU numbering system is substituted with proline is preferable. Note here that in the specification, amino acid positions assigned to CDRs and frameworks in a variable region of an antibody are specified according to Kabat's numbering (see Sequences of Proteins of Immunological Interest (National Institute of Health, Bethesda, Md., 1987 and 1991)). Furthermore, amino acids in the constant region are represented according to the EU numbering system based on Kabat's amino acid positions (see Sequences of proteins of immunological interest, NIH Publication No. 91-3242).

In Fc regions of the PD-1/CD3 bispecific antibody of the present invention, arbitrary amino acids therein may be substituted such that two different heavy chains are easily associated with each other. Examples of the preferable embodiments include a PD-1/CD3 bispecific antibody of which in the constant region of the heavy chain having the VH of the first arm specifically binding to PD-1, leucine at position 351 according to the EU numbering system is substituted with lysine, and threonine at position 366 according to the EU numbering system is substituted with lysine; and of which in the constant region of the heavy chain having the VH of the second arm specifically binding to CD3, leucine at position 351 according to the EU numbering system is substituted with aspartic acid, and leucine at position 368 according to the EU numbering system is substituted with glutamic acid. The examples also include a PD-1/CD3 bispecific antibody of which in the constant region in the heavy chain having the VH of the first arm specifically binding to PD-1, leucine at position 351 according to the EU numbering system is substituted with aspartic acid, and leucine at position 368 is substituted with glutamic acid; and of which in the constant region in the heavy chain having the VH of the second arm specifically binding to CD3, leucine at position 351 according to the EU numbering system is substituted with lysine, and threonine at position 366 according to the EU numbering system is substituted with lysine.

The First Arm Specifically Binding to PD-1

In the present specification, the "first arm specifically binding to PD-1" (hereinafter, which may be abbreviated as "first arm") means a part of an antibody containing at least a VH of an antibody specifically binding to PD-1 (hereinafter, which may be abbreviated as "anti-PD-1 antibody"), regardless of whether it is contained in a part of the antibody or antibody fragment thereof, or exists not as a part but as a single body. For example, such a first arm is composed of a VH of an anti-PD-1 antibody, and a VL of the common light chain constituting the same anti-PD-1 antibody. Furthermore, examples of the first arm also include a Fab part of the antibody including the VH and VL. Herein, the term "specifically binding to PD-1" is used as a feature that it can directly bind to PD-1 with binding activity of at least $1 \times 10^{-5}$ M, preferably $1 \times 10^{-7}$ M, and more preferably more than $1 \times 10^{-9}$ M affinity (dissociation constant (Kd value)), and does not substantially bind to other receptor members belonging to a so-called CD28 family receptor, e.g., at least, CD28, CTLA-4 and ICOS. Furthermore, an "antibody" in the "antibody specifically binding to PD-1" or in the "anti-PD-1 antibody" means a full-length antibody composed of two heavy chains and two light chains linked with disulfide bonds, and preferably a monoclonal antibody thereof.

Herein, examples of the "first arm specifically binding to PD-1" include:

(a) the VH-CDR1 comprising the amino acid sequence represented by HYJ$^1$LH [wherein J$^1$ represents G (glycine) or A (alanine), and herein, alphabets represented by J$^1$ or other represent a one letter amino-acid abbreviation, respectively];

(b) the VH-CDR2 comprising the amino acid sequence represented by WJ$^2$NTNTU$^2$NPTX$^2$AQGFTG [wherein J$^2$ represents L (leucine) or I (isoleucine), U$^2$ represents E (glutamic acid) or G (glycine), X$^2$ represents F (phenylalanine) or Y (tyrosine), and herein, alphabets represented by J$^2$, U$^2$ or X$^2$, or other represent the same as the above, respectively]; and (c) the VH-CDR3 comprising an amino acid sequence represented by GDJ$^3$VVPTTIWNYYU$^3$X$^3$MZ$^3$V [wherein J$^3$ represents M (methionine) or L (leucine), U$^3$ represents H (histidine) or Y (tyrosine), X$^3$ represents F (phenylalanine) or Y (tyrosine), Z$^3$ represents D (aspartic acid) or E (glutamic acid), and herein, alphabets represented by J$^3$, U$^3$, X$^3$ or Z$^3$, or other alphabets represent the same as the above, respectively].

Herein, preferable embodiments of the "first arm specifically binding to PD-1" include those containing:

(1a) a VH having each VH-CDR in which J$^1$ in the HYJ$^1$LH sequence as VH-CDR1 represents G (glycine); in the WJ$^2$NTNTU$^2$NPTX$^2$AQGFTG as VH-CDR2, J$^2$ represents L (leucine), U$^2$ represents E (glutamic acid), and X$^2$ represents F (phenylalanine), respectively; in the GDJ$^3$VVPTTIWNYYU$^3$X$^3$MZ$^3$V sequence as VH-CDR3, J$^3$ represents M (methionine), U$^3$ represents H (histidine), X$^3$ represents F (phenylalanine), and Z$^3$ represents D (aspartic acid), respectively;

(2a) a VH having each VH-CDR in which J$^1$ in the HYJ$^1$LH sequence as VH-CDR1 represents G (glycine); in the WJ$^2$NTNTU$^2$NPTX$^2$AQGFTG as VH-CDR2, J$^2$ represents I (isoleucine), U$^2$ represents G (glycine), and X$^2$ represents Y (tyrosine), respectively; in the GDJ$^3$VVPTTIWNYYU$^3$X$^3$MZ$^3$V sequence as VH-CDR3, J$^3$ represents L (leucine), U$^3$ represents H (histidine), X$^3$ represents Y (tyrosine), and Z$^3$ represents E (glutamic acid), respectively;

(3a) a VH having each VH-CDR in which J$^1$ in the HYJ$^1$LH sequence as VH-CDR1 represents A (alanine); in the WJ$^2$NTNTU$^2$NPTX$^2$AQGFTG as VH-CDR2, J$^2$ represents L (leucine), U$^2$ represents E (glutamic acid), and X$^2$ represents Y (tyrosine), respectively; in the GDJ$^3$VVPTTIWNYYU$^3$X$^3$MZ$^3$V sequence as VH-CDR3, J$^3$ represents M (methionine), U$^3$ represents Y (tyrosine), X$^3$ represents Y (tyrosine), and Z$^3$ represents D (aspartic acid), respectively; and (4a) a VH having each VH-CDR in which J$^1$ in the HYJ$^1$LH sequence as VH-CDR1 represents A (alanine); in the WJ$^2$NTNTU$^2$NPTX$^2$AQGFTG as VH-CDR2, J$^2$ represents L (leucine), U$^2$ represents E (glutamic acid), and X$^2$ represents F (phenylalanine), respectively; J³ represents M (methionine), U³ represents H (histidine), in the GDJ³VVPTTIWNYYU³X³MZ³V sequence as VH-CDR3, X³ represents F (phenylalanine), and Z³ represents D (aspartic acid), respectively.

Furthermore, as preferable examples of another embodiment, the "first arm specifically binding to PD-1" include any one of the VH selected from:

(1b) the VH having VH-CDR1 comprising the amino acid sequence set forth in SEQ ID No. 6, the VH-CDR2 comprising the amino acid sequence set forth in SEQ ID No. 7, and the VH-CDR3 comprising the amino acid sequence set forth in SEQ ID No. 8;

(2b) the VH having VH-CDR1 comprising the amino acid sequence set forth in SEQ ID No. 9, the VH-CDR2 comprising the amino acid sequence set forth in SEQ ID No. 10, and the VH-CDR3 comprising the amino acid sequence set forth in SEQ ID No. 11;

(3b) the VH having the VH-CDR1 comprising the amino acid sequence set forth in SEQ ID No. 12, the VH-CDR2 comprising the amino acid sequence set forth in SEQ ID No. 13, and the VH-CDR3 comprising the amino acid sequence set forth in SEQ ID No. 14;

(4b) the VH having the VH-CDR1 comprising the amino acid sequence set forth in SEQ ID No. 15, the VH-CDR2 comprising the amino acid sequence set forth in SEQ ID No. 16, and the VH-CDR3 comprising the amino acid sequence set forth in SEQ ID No. 17; and (5b) the VH having the VH-CDR1 comprising the amino acid sequence set forth in SEQ ID No. 18, the VH-CDR2 comprising the amino acid sequence set forth in SEQ ID No. 19, and the VH-CDR3 comprising the amino acid sequence set forth in SEQ ID No. 20.

Furthermore, the "first arm specifically binding to PD-1" of the present invention includes those of which 1 to 5 arbitrary amino acid residue(s) is/are substituted with other amino acid(s) (preferably, conservative amino acid(s) thereof) in each VH-CDR of any one of the VH selected from the above-mentioned (1a) to (4a) or (1b) to (5b), and which have substantially the same binding activity to PD-1 as that of the original first arm without any substitutions with the amino acid(s). For example, as to the VH-CDR1, one amino acid residue is substituted with a conservative amino acid thereof. As to the VH-CDR2 or the VH-CDR3, one or two amino acid residues is/are substituted with the conservative amino acid(s) thereof, respectively. Herein, the substitution with a conservative amino acid means the exchangeability with a residue having a similar side-chain. For example, a group of amino acids having an aliphatic side-chain includes glycine, alanine, valine, leucine, and isoleucine; a group of amino acids having an aliphatic hydroxyl side-chain includes serine and threonine; a group of amino acids having amide-containing side-chain includes asparagine and glutamine; a group of amino acids having an aromatic side-chain includes phenylalanine, tyrosine and tryptophane; a group of amino acids having a basic side-chain includes lysine, arginine and histidine; and a group of amino acids having a sulfur-containing side-chain includes cysteine and methionine. Preferable examples of the substitution with a conservative amino acid include a substitution among valine, leucine and isoleucine, a substitution between phenylalanine and tyrosine, a substitution between lysine and arginine, and a substitution between alanine and valine, as well as a substitution between asparagine and glutamine. Furthermore, herein, the sentence "which have substantially the same binding activity to PD-1 as that of the original first arm without any substitutions with the amino acid(s)" mentioned above means that the binding activity to PD-1 of the first arm substituted with the same amino acid(s) is 95% or more, preferably 98% or more, and more preferably 99% or more to that of the original first arm without any substitutions with the same amino acid(s).

Furthermore, the "first arm specifically binding to PD-1" in the present invention includes those containing a VH having each VH-CDR having the above-mentioned specific amino acid sequence and in which the framework of the VH is encoded by a specific germ-line gene or gene thereof with somatic mutation(s). For example, the VH presented by any one selected from the above-mentioned (1a) to (4a) or (1b) to (5b) can be encoded by the VDJ recombinant gene in which the germ-line V gene is IGHV7-4-1 and the germ-line J gene is JH6c or gene thereof with somatic mutation(s). Herein, the amino acid sequence encoded by the germ-line V gene IGHV7-4-1 corresponds to the amino acid sequence set forth in SEQ ID No. 21 (FIG. 3).

The frameworks of the VH of the first arm specifically binding to PD-1 of the present invention may be encoded by the germ-line VDJ recombinant gene with somatic mutation(s). For example, since the FR1, FR2, and FR3 of the VH presented by any one selected from the above-mentioned (1a) to (4a) or (1b) to (5b) of which the germ-line V gene is IGHV7-4-1 is different from an amino acid sequence encoded by the IGHV7-4-1 gene at the position of the amino acid shown in FIG. 4, they undergo somatic mutation at each of the positions. For example, as to the FR1 region, in the amino acid sequence set forth in SEQ ID No. 21, lysine at position 13 may be substituted with glutamine, alanine at position 16 may be substituted with valine, or lysine at position 19 may be substituted with methionine, respectively, or which may be substituted in arbitrary combination of a plurality thereof. As to the FR2 region, valine at position 37 in the amino acid sequence set forth in SEQ ID No. 21 is substituted with leucine. As to the FR3 region, in the amino acid sequence set forth in SEQ ID No. 21, serine at position 77 may be substituted with threonine, or cysteine at position 84 may be substituted with serine or asparagine, respectively, or which may be substituted in arbitrary combination of a plurality thereof. Furthermore, as to the FR4 region of VH presented by any one selected from the above-mentioned (1a) to (4a) or (1b) to (5b), in the amino acid sequence (Trp-Gly-Lys-Gly-Thr-Thr*-Val-Thr-Val-Ser-Ser) (SEQ ID No. 41) of the FR4 region derived from a J gene JH6c, lysine (Lys) may be substituted with glutamine or asparagine, and/or threonine (Thr) marked with an asterisk may be substituted with leucine. Each of the FR1, FR2, FR3 and FR4 including combination of any of amino acid substitution(s) mentioned above have no substantial effect on the functions of the first arm specifically binding to PD-1, and can be used as frameworks.

Furthermore, the "first arm specifically binding to PD-1" of the present invention includes those having each CDR having the above-defined amino acid sequence and in which the FR amino acid sequences in the VH are encoded by a specific germ-line gene or gene thereof with somatic mutation(s). Examples of such a first arm include those having the VH comprising the amino acid sequence set forth in any one selected from SEQ ID Nos. 1 to 5.

Furthermore, examples of such a "first arm specifically binding to PD-1" include those having a VH comprising an amino acid sequence having at least 80% identity, preferably at least 90% identity, more preferably at least 95% identity, furthermore preferably at least 98% identity, and further more preferably at least 99% identity to the amino acid sequence set forth in any one selected from SEQ ID Nos. 1 to 5, and in which the difference from the amino acid sequence of the VH in the original first arm has no substantial effect on the binding activity to PD-1 (hereinafter, may be abbreviated as a "homologous first arm"). Herein, the term "% identity" used in comparison of the identity of amino acid sequences is defined as the percentage of the amino acid sequence identical to the reference amino acid sequence (herein, the reference amino acid sequence in which the gap has been introduced when being needed to maximize the sequence identity.) when two sequences are aligned. Furthermore, herein, the sentence "the different from the amino acid sequence of the VH in the original first arm has no substantial effect on the binding activity to PD-1" means that the binding activity to PD-1 of the homologous first arm is 95% or more, preferably 98% or more, and more preferably 99% or more to the binding activity of the original first arm.

In a yet another embodiment, the "first arm specifically binding to PD-1" of the present invention also includes those having a variable region (herein, the variable region contains a VH and VL constituting it.) of the anti-PD-1 antibody cross-competing for (1) the binding to PD-1 with the first arm having the VH presented by any one selected from the above-mentioned (1a) to (4a) or (1b) to (5b) or the VH comprising the amino acid sequence set forth in any one selected from SEQ ID Nos. 1 to 5 and the VL of the common light chain, or (2) the binding to PD-1 with the variable region of the monoclonal antibody specifically binding to PD-1 having the same VH and VL, and further includes those having the variable region of the anti-PD-1 antibody with which the binding to PD-1 is cross-competed (3) by the first arm having the VH presented by any one selected from the above-mentioned (1a) to (4a) or (1b) to (5b) or the VH comprising the amino acid sequence set forth in any one selected from SEQ ID Nos. 1 to 5 and the VL of the common light chain or (4) by the variable region of the monoclonal antibody specifically binding to PD-1 having the same VH and VL. Herein, the sentence "cross-competing for the binding to PD-1" means that it inhibits the binding of the first arm to PD-1, regardless of the degree thereof, by binding to the epitope which is the same as or partially overlaps with that of the first arm exemplified in this specification, or that the binding to PD-1 of the antibody binding to the epitope which is the same as or partially overlaps with that of the exemplified first arm is inhibited by the exemplified first arm, regardless of the degree thereof. The cross-competition can be evaluated by a competitive binding assay. For example, it can be determined using Biacore analysis, ELISA assay, flow cytometry, enzyme linked immunosorbent assay (ELISA), fluorescence energy transfer method (FRET) and fluorometric microvolume assay technology (FMAT (registered trademark)).

Examples of the first arm cross-competing for the binding to PD-1 with the first arm having the VH presented by the above-mentioned (5b) and the VL of the common light chain include the first arm having the VH presented by any one selected from the above-mentioned (1b) to (4b) and the VL of the common light chain (preferably, the VL having the VL-CDR1 comprising the amino acid sequence set forth in SEQ ID No. 26, the VL-CDR2 comprising the amino acid sequence set forth in SEQ ID No. 27 and the VL-CDR3 comprising the amino acid sequence set forth in SEQ ID No. 28), and further the first arm having the VH comprising the amino acid sequence set forth in any one selected from SEQ ID Nos. 1 to 4 and the VL of the common light chain (preferably, the VL comprising the amino acid sequence set forth in SEQ ID No. 25).

Furthermore, examples of the first arm cross-competing for the binding to PD-1 with the first arm having the VH presented by any one selected from the above-mentioned (1b) to (4b) or the VH comprising the amino acid sequence set forth in any one selected from SEQ ID Nos. 1 to 4 and the VL of the common light chain include the first arm having the VH presented by the above-mentioned (5b) and the VL of the common light chain (preferably, the VL having the VL-CDR1 comprising the amino acid sequence set forth in SEQ ID No. 26, the VL-CDR2 comprising the amino acid sequence set forth in SEQ ID No. 27 and the VL-CDR3 comprising the amino acid sequence set forth in SEQ ID No. 28), and further the first arm having the VH comprising the amino acid sequence set forth in SEQ ID Nos. 5 and the VL of the common light chain (preferably, the VL comprising the amino acid sequence set forth in SEQ ID No. 25).

Herein, preferable examples of the "first arm specifically binding to PD-1" of the present invention include the first arm having the VH presented by any one selected from the above-mentioned (1b) to (5b). Furthermore, as mentioned above, the preferable first arm also includes those in which 1 to 5 arbitrary amino acid residues are substituted with other amino acid(s) (preferably, conservative amino acid(s) thereof) in each CDR of the VH, and the substitution with the amino acid(s) does not substantially affect the binding activity to PD-1. Furthermore, as mentioned above, the preferable first arm includes those having the VH in which the amino acid sequences of frameworks are encoded by the germ-line V gene IGHV7-4-1 or the J gene JH6c or gene(s) thereof with somatic mutation(s). Then, more preferable examples of the first arm include those having the VH comprising the amino acid sequence set forth in any one selected from SEQ ID Nos. 1 to 5.

Furthermore, the first arm specifically binding to PD-1 of the present invention preferably a common light chain, and preferable examples of such a common light chain include a light chain encoded by the IGVK1-39/JK1 common light chain. More preferable examples include the light chain containing a VL having the CDR1 comprising the amino acid sequence set forth in SEQ ID No. 26, the CDR2 comprising the amino acid sequence set forth in SEQ ID No. 27, and the CDR3 comprising the amino acid sequence set forth in SEQ ID No. 28, and further preferable examples include the light chain containing the VL comprising the amino acid sequence set forth in SEQ ID No. 25. Furthermore, preferable examples of the constant region of the common light chain include the light chain constant region comprising the amino acid sequence set forth in SEQ ID No. 29.

Furthermore, preferable examples of the "first arm specifically binding to PD-1," include those which allows the interaction between PD-1 and PD-L1, interaction between PD-1 and PD-L2, or both of those interactions. Herein, the sentence "allows an interaction between PD-1 and PD-L1, interaction between PD-1 and PD-L2, or both of those interactions" means that even when there is the PD-1/CD3 bispecific antibody of the present invention at a 20-fold excess over the concentration of the soluble form PD-L1 or PD-L2, the interaction between PD-L1 and PD-1, interaction between PD-L2 and PD-1, or both of those interactions are maintained 50% or more, preferably 70% or more, and more preferably 80% or more, compared with those when there is no PD-1/CD3 bispecific antibody of the present invention. Furthermore, the definition of "allows the interaction between PD-1 and PD-L1, interaction between PD-1 and PD-L2, or both of those interactions" may have the same meaning as that of "which does not substantially inhibit the interaction between PD-1 and PD-L1, interaction between PD-1 and PD-L2, or both of those interactions."

Correspondence relation between each clone of the anti-PD-1 monoclonal antibody obtained to construct the PD-1/CD3 bispecific antibody of the present invention and the VH amino acid sequence thereof and SEQ ID numbers thereof is shown in FIG. 5. Correspondence relation between each CDR amino acid sequence in VH of each anti-PD-1 monoclonal antibody clone and SEQ ID number thereof is shown in FIG. 6.

The Second Arm Specifically Binding to CD3

In the present specification, the "second arm specifically binding to CD3" (hereinafter, which may be abbreviated as the "second arm") means an antibody portion having at least a VH of an antibody specifically binding to CD3 (hereinafter, which may be abbreviated as an "anti-CD3 antibody"), regardless of whether it is contained in a part of an antibody or antibody fragment, or exists not as a part but as a single body. For example, such a second arm is composed of the VH of the anti-CD3 antibody, and a VL of the common light chain constituting the same anti-CD3 antibody, and further includes a Fab part of an antibody including the VH and VL. Herein, the sentence "specifically binding to CD3" is used as the feature that an antibody can directly bind to CD3 with binding activity of at least $1\times10^{-5}$ M, preferably $1\times10^{-7}$ M, and more preferably more than $1\times10^{-9}$ M affinity (dissociation constant (Kd value)), and does not substantially bind to the other protein. Furthermore, the "antibody" in the "antibody specifically binding to CD3" or the "anti-CD3 antibody" means a full-length antibody, which is composed of two heavy chains and two light chains linked with disulfide bonds, and preferably a monoclonal antibody thereof.

Herein, examples of the "second arm specifically binding to CD3" include those containing the VH having: (1c) the VH-CDR1 comprising the amino acid sequence set forth in SEQ ID No. 37, the VH-CDR2 comprising the amino acid sequence set forth in SEQ ID No. 38, and the VH-CDR3 comprising the amino acid sequence set forth in SEQ ID No. 39.

Furthermore, the "second arm specifically binding to CD3" of the present invention includes those in which 1 to 5 arbitrary amino acid residues are substituted with other amino acid(s) (preferably, conservative amino acid(s) thereof) in each CDR of the VH in the above-mentioned (1c), and which have substantially the same binding activity to CD3 as that of the original second arm without any substitutions with the same amino acid(s). For example, as to the CDR1, one amino acid residue is substituted with a conservative amino acid thereof. As to the CDR2 or the CDR3, one or two amino acid residues is/are substituted with conservative amino acid(s) thereof, respectively. Herein, the sentence "which have substantially the same binding activity to CD3 as that of the original second arm without any substitutions with the same amino acid(s)" mentioned above means that the binding activity to CD3 of the second arm substituted with the amino acid is 95% or more, preferably 98% or more, and more preferably 99% or more to that of the original second arm without any substitutions with the same amino acid(s). Note here that examples of the "substitution with conservative amino acid(s)" in each VH-CDR of the second arm include those of the amino acid substitution in the first arm mentioned above.

Furthermore, the "second arm specifically binding to CD3" in the present invention also includes those containing the VH having each CDR comprising the specific amino acid sequence mentioned above and in which the FR amino acid sequences of the VH are encoded by a specific germ-line gene or gene thereof with somatic mutation(s). For example, the VH of the above-mentioned (1c) is encoded by the VDJ recombinant gene in which the germ-line V gene is IGHV3-33 or gene thereof with somatic mutation(s). Herein, the amino acid sequence encoded by the V gene IGHV3-33 of the germ line (SEQ ID No. 22) is shown in FIG. 3.

Furthermore, the "second arm specifically binding to CD3" of the present invention also those which contain each CDR having the above-mentioned specific amino acid sequence, and in which the amino acid sequences of the FRs in the VH is encoded by a specific germ-line gene or gene thereof with somatic mutation(s). Examples of such a second arm include those having the VH comprising the amino acid sequence set forth in SEQ ID No. 36.

Furthermore, examples of such a "second arm specifically binding to CD3" include those which have a VH comprising an amino acid sequence having at least 80%, preferably at least 90%, more preferably at least 95%, further more preferably at least 98%, and still further preferably at least 99% identity to the amino acid sequence set forth in SEQ ID No. 36, and in which the difference from the VH amino acid sequence of the original second arm has no substantial effect on the binding activity to CD3 (hereinafter, may be abbreviated as a "homologous second arm"). Herein, the sentence "the difference from the VH amino acid sequence of the original second arm has no substantial effect on the binding activity to CD3" means that the binding activity of the homologous second arm to CD3 is 95% or more, preferably 98% or more, and more preferably 99% or more to the binding activity of the original second arm.

In a yet another embodiment, the "second arm specifically binding to CD3" of the present invention includes those containing a variable region of the anti-CD3 antibody (herein, the variable region includes the VH and VL constituting it.) cross-competing for (1) the binding to CD3 with the second arm having the VH presented by the above-mentioned (1c) or the VH comprising the amino acid sequence set forth in SEQ ID No. 36 and the VL of the common light chain, or (2) the binding to CD3 with the variable region of the monoclonal antibody specifically binding to CD3 having the same VH and VL. Herein, the "cross-competing for the binding to CD3" means that it inhibits the binding of the second arm to CD3, regardless of the degree thereof, by binding to the epitope which is the same as or partially overlaps with the second arm exemplified in the present specification. Herein, the cross-competition can be similarly evaluated by the same method as described about the "first arm specifically binding to PD-1".

Herein, preferable examples of the "second arm specifically binding to CD3" of the present invention include the second arm having the VH presented by the above-mentioned (1c). Furthermore, as mentioned above, preferable examples of the second arm also include those in which 1 to 5 arbitrary amino acid residue(s) is/are substituted with other amino acid(s) (preferably, conservative amino acid(s) thereof) in each CDR of the VH, and the substitution with amino acid does not substantially affect the binding activity to CD3. Furthermore, as mentioned above, preferable examples of the second arm include those having the VH in which the amino acid sequences of frameworks are encoded by the germ-line gene IGHV3-33 or gene thereof with somatic mutation(s). Then, more preferable examples of the second arm include those having the VH comprising the amino acid sequence set forth in SEQ ID No. 36.

Hereinafter, correspondence relations between the anti-CD3 antibody clones to construct the PD-1/CD3 bispecific antibodies of the present invention, VH amino acid sequences thereof, and SEQ ID numbers thereof are shown in FIG. 7, respectively. Correspondence relations between the CDR amino acid sequences in the VH of the anti-CD3 antibody clones and SEQ ID numbers thereof are shown in FIG. 8, respectively.

The "second arm specifically binding to CD3" of the present invention preferably contains common light chains, and preferable examples of such a common light chain include the IGVK1-39/JK1 common light chain. More preferable examples include a light chain containing a VL having the CDR1 comprising the amino acid sequence set forth in SEQ ID No. 26, the CDR2 comprising the amino acid sequence set forth in SEQ ID No. 27, and the CDR3 comprising the amino acid sequence set forth in SEQ ID No. 28, and further preferable examples include the light chain containing the VL comprising the amino acid sequence set forth in SEQ ID No. 25. Furthermore, preferable examples of the constant region of the common light chain include the light chain constant region comprising the amino acid sequence set forth in SEQ ID No. 29.

Preferable examples of the "second arm specifically binding to CD3" of the present invention include a second arm specifically binding to CDR.

Examples of a preferable isotype of the PD-1/CD3 bispecific antibody of the present invention include an IgG antibody, further preferably an IgG$_1$ antibody or an IgG4 antibody, and more preferably an IgG$_1$ antibody.

On the other hand, a preferable embodiment of the PD-1/CD3 bispecific antibody of the present invention is, e.g., the PD-1/CD3 bispecific antibody,
wherein the first arm specifically binding to PD-1 contains:
  (A) the VH in which 1 to 5 arbitrary amino acid residue(s) may be substituted with other amino acid(s) (preferably, conservative amino acid(s) thereof) in any one or more of the CDR(s) selected from the VH-CDR1, VH-CDR2 and VH-CDR3 in the VH presented by any one selected from the above-mentioned (1a) to (4a) or (1b) to (5b); and
  (B) the VL of common light chain having the CDR1 comprising the amino acid sequence set forth in SEQ ID No. 26, the CDR2 comprising the amino acid sequence set forth in SEQ ID No. 27, and the CDR3 comprising the amino acid sequence set forth in SEQ ID No. 28; and
wherein the second arm specifically binding to CD3 contains:
  (C) the VH in which 1 to 5 arbitrary amino acid residue(s) may be substituted with other amino acid(s) (preferably, conservative amino acid(s) thereof) in any one or more of the CDR(s) selected from the VH-CDR1, VH-CDR2 and VH-CDR3 in the VH presented by the above mentioned (1c); and
  (D) the VL of common light chain having the CDR1 comprising the amino acid sequence set forth in SEQ ID No. 26, the CDR2 comprising the amino acid sequence set forth in SEQ ID No. 27, and the CDR3 comprising the amino acid sequence set forth in SEQ ID No. 28.

A more preferable embodiment of the PD-1/CD3 bispecific antibody of the present invention is, e.g., the PD-1/CD3 bispecific antibody,
wherein the first arm specifically binding to PD-1 contains:
  (A) the VH presented by any one selected from the above (1a) to (4a) or (1b) to (5b), and
  (B) the VL of common light chain having the CDR1 comprising the amino acid sequence set forth in SEQ ID No. 26, the CDR2 comprising the amino acid sequence set forth in SEQ ID No. 27, and the CDR3 comprising the amino acid sequence set forth in SEQ ID No. 28; and
wherein the second arm specifically binding to CD3 contains:
  (C) the VH presented by the above (1c); and
  (D) the VL of common light chain having the CDR1 comprising the amino acid sequence set forth in SEQ ID No. 26, the CDR2 comprising the amino acid sequence set forth in SEQ ID No. 27, and the CDR3 comprising the amino acid sequence set forth in SEQ ID No. 28.

Furthermore, another preferable embodiment the PD-1/CD3 bispecific antibody of the present invention is, e.g., the PD-1/CD3 bispecific antibody,
wherein the first arm specifically binding to PD-1 contains:
  (A) the VH comprising the amino acid sequence set forth in any one selected from SEQ ID Nos. 1 to 5, or a VH comprising an amino acid sequence having at least 80% identity to the amino acid sequence of the same VH; and
  (B) the VL of common light chain comprising the amino acid sequence set forth in SEQ ID No. 25; and
wherein the second arm specifically binding to CD3 contains,
  (C) the VH comprising the amino acid sequence set forth in SEQ ID No. 36, or a VH comprising an amino acid sequence having an identity of at least 80% to the amino acid sequence of the same VH; and
  (D) the VL of common light chain comprising the amino acid sequence set forth in SEQ ID No. 25.

The other embodiments more preferably include, e.g., the PD-1/CD3 bispecific antibody,
wherein the first arm specifically binding to PD-1 contains:
  (A) the VH comprising the amino acid sequence set forth in any one selected from SEQ ID Nos. 1 to 5; and
  (B) the VL of common light chain comprising the amino acid sequence set forth in SEQ ID No. 25; and
wherein the second arm specifically binding to CD3 contains:
  (C) the VH comprising the amino acid sequence set forth in SEQ ID No. 36; and
  (D) the VL of common light chain comprising the amino acid sequence set forth in SEQ ID No. 25.

In the PD-1/CD3 bispecific antibody of the present invention, in case that the antibody is an IgG$_1$ antibody, the IgG$_1$ antibody in which leucine at position 235 according to the EU numbering system is substituted with glycine, and/or glycine at position 236 according to the EU numbering system is substituted with arginine on two heavy chain constant regions or a hinge region is preferable. Furthermore, a bispecific antibody in which a C-terminal amino acid of heavy chain, e.g., lysine at position 447 according to the EU numbering system has been deleted is preferable. Furthermore, in case that the PD-1/CD3 bispecific antibody is an IgG$_4$ antibody, an antibody in which serine located in a hinge region and at position 228 according to the EU numbering system is substituted with proline is preferable.

Furthermore, the preferable embodiment in case that the PD-1/CD3 bispecific antibody is the IgG$_1$ antibody include those in which in a constant region of the heavy chain having the VH of the first arm specifically binding to PD-1, leucine at position 351 according to the EU numbering system is substituted with lysine and threonine at position 366 is substituted with lysine, and in a constant region of the heavy chain having the VH of the second arm specifically binding to CD3, leucine at position 351 is substituted with aspartic acid and leucine at position 368 is substituted with glutamic acid. Furthermore, the $IgG_1$ antibody in which in a constant region of the heavy chain having the VH of the first arm specifically binding to PD-1, leucine at position 3M according to the EU numbering system is substituted with aspartic acid and leucine at position 368 is substituted with glutamic acid, and in a constant region of the heavy chain having the VH of the second arm specifically binding to CD3, leucine at position 3M is substituted with lysine and threonine at position 366 is substituted with lysine is also preferable.

Examples of the preferable embodiment of the PD-1/CD3 bispecific $IgG_1$ antibody in which all of the above-mentioned amino acid substitutions in the heavy chain constant region are taken include those in which the heavy chain having the VH of the first arm specifically binding to PD-1 contains the heavy chain constant region comprising the amino acid sequence set forth in SEQ ID No. 23, and the heavy chain having the VH of the second arm specifically binding to CD3 contains the heavy chain constant region comprising the amino acid sequence set forth in SEQ ID No. 24. Those amino acid sequences are shown in FIG. 9.

The most preferable embodiments of the PD-1/CD3 bispecific antibody of the present invention are the PD1-1(Bi) clone, PD1-2(Bi) clone, PD1-3(Bi) clone, PD1-4(Bi) clone and PD1-5(Bi) clone generated by the method described in Example 8 of the present specification.

Preferable features of the PD-1/CD3 bispecific antibody of the present invention include: (1) allowing the interaction between PD-1 and PD-L1, interaction between PD-1 and PD-L2, or both of the interactions; and/or (2) sufficiently reducing cytokine production. Herein, the sentence "allowing the interaction between PD-1 and PD-L1, interaction between PD-1 and PD-L2, or both of the interactions" means the same as that described about the "first arm specifically binding to PD-1." On the other hand, the sentence "sufficiently reducing cytokine production" means that, e.g., during intravenous administration or in 24 hours after that administration, by drip infusion of the PD-1/CD3 bispecific antibody of the present invention, e.g., concentration of cytokine containing IL-2, IFN-γ and/or TNF-α in blood or tissue do not increase, or increase to only such a degree that it can be suppressed by steroid administration.

Method for Producing and Purifying the PD-1/CD3 Bispecific Antibody

The PD-1/CD3 bispecific antibody and antibody fragment thereof of the present invention can also be manufactured by the method disclosed in WO2014/051433, WO2013/157953 or WO2013/157954.

Specifically, the PD-1/CD3 bispecific antibody and antibody fragment thereof of the present invention can be manufactured by gene-transferring an expression vector into which (1) a polynucleotide encoding the heavy chain containing the VH of the first arm specifically binding to PD-1, (2) a polynucleotide encoding the heavy chain containing the VH of the second arm specifically binding to CD3, and (3) a polynucleotide encoding the common light chain have been inserted, respectively, into mammalian animal cells to transform them, and then by having them express and secrete both of the heavy chain and common light chain.

Herein, any host cells for expressing the PD-1/CD3 bispecific antibody of the present invention can be used as long as they can be gene-transferred using an expression vector and allow the transferred expression vector to express. The host cells are preferably insect cells such as SF-9 and SF-21, more preferably mammalian cells such as mouse cells such as CHO cells, BHK cells, SP2/0 cells and NS-0 myeloma cells, primate cells such as COS and Vero cells, MDCK cells, BRL 3A cells, hybridoma, tumor cells, immortalized primary cells, W138, HepG2, HeLa, HEK293, HT1080 or embryonic retina cells such as PER.C6. Note here that in selection of the expression system, expression vectors for and hosts as mammalian host cells may be used to ensure that an antibody is appropriately glycosylated. Human cell lines, preferably PER.C6 are advantageously used to obtain an antibody of which glycosylated patterns correspond to those for human.

Protein production in host cells transformed by gene-transfer of expression vectors can be carried out with reference to, e.g., Current Protocols in Protein Science (1995), Coligan J E, Dunn B M, Ploegh H L, Speicher D W, Wingfield P T, ISBN 0-471-11184-8, Bendig, 1988. Furthermore, general guidelines, procedures and practical methods to maximize the productivity of host cell culture can be carried out with reference to Mammalian Cell Biotechnology: a Practical Approach (M. Butler, ed., IRL Press, 1991). Expression of antibodies in host cells is described in, e.g., publication such as EP0120694, EP0314161, EP0481790, EP0523949, U.S. Pat. No. 4,816,567, WO2000/63403, and the like.

Herein, culture conditions of host cells can be optimized by a well-known method, and thereby protein production can be optimized. Examples of culture include, batch culture, feeding culture, continuous culture, and hollow-fiber culture in a petri dish, roller bottle, or reaction chamber. In order to produce recombinant protein by cell culture in a large scale and continuously, it is preferable that cells are proliferated in suspension liquid. Furthermore, it is more preferable that cells are cultured in a condition without animal- or human-derived serum or some components in animal- or human-derived serum.

An antibody expressed in host cells and then recovered from cells or cell culture by well-known methods can be purified using well-known methods. Examples of the purification method include an immunoprecipitation method, centrifugation method, filtration, size-exclusion chromatography, affinity chromatography, cation and/or anion exchange chromatography, hydrophobic interaction chromatography, and the like. Furthermore, protein A or protein G affinity chromatography may be preferably used (see, e.g., U.S. Pat. Nos. 4,801,687 and 5,151,504).

Anti-PD-1 Monoclonal Antibody

The present invention includes a "monoclonal antibody specifically binding to PD-1" (hereinafter, may be abbreviated as an "anti-PD-1 monoclonal antibody") to construct the PD-1/CD3 bispecific antibody of the present invention and antibody fragment thereof.

One embodiment of the anti-PD-1 monoclonal antibody of the present invention is a monoclonal antibody capable of specifically binding to PD-1 by association of a VH and the VL of the common light chain of the present invention. Herein, the sentence "specifically binding to PD-1" is used as a feature that it can directly bind to PD-1 with binding activity (dissociation constant (Kd value)) of at least $1 \times 10^{-5}$ M, preferably $1 \times 10^{-7}$ M, and more preferably more than $1 \times 10^{-9}$ M affinity, and does not substantially bind to receptor members belonging to a so-called CD28 family receptor, e.g., CD28, CTLA-4 and ICOS. Herein, an "antibody" in the "monoclonal antibody specifically binding to PD-1" or the "anti-PD-1 antibody" means a full-length antibody composed of two heavy chains and two light chains linked with disulfide bonds. Furthermore, a "fragment of the monoclonal antibody specifically binding to PD-1" is a part of the full-length antibody, and an antibody including at least an antigen binding part, and examples of which include Fab, Fab', Fv, scFv, F(ab')$_2$, and the like.

Examples of the anti-PD-1 monoclonal antibody of the present invention include those having any one of the VH selected from the above (1a) to (4a) or (1b) to (5b) constituting the VH of the "first arm specifically binding to PD-1" or the VH comprising the amino acid sequence set forth in any one selected from SEQ ID Nos. 1 to 5, and the VL of common light chain of the present specification.

Furthermore, the anti-PD-1 monoclonal antibody of the present invention includes those in which 1 to 5 arbitrary amino acid residue(s) is/are substituted with other amino acid(s) (preferably, conservative amino acid(s) thereof) in each CDR of any one of the VH selected from the above-mentioned (1a) to (4a) or (1b) to (5b), and which have substantially the same binding activity to PD-1 as that of the anti-PD-1 monoclonal antibody having the original VH without any substitutions with the same amino acid(s). For example, as to the CDR1, one amino acid residue is substituted with a conservative amino acid thereof. As to the CDR2 or the CDR3, one or two amino acid residue(s) is/are substituted with conservative amino acids thereof, respectively. Herein, the sentence "which have substantially the same binding activity to PD-1 as that of the anti-PD-1 monoclonal antibody having the original VH without any substitutions with the same amino acid(s)" means that the binding activity to PD-1 of anti-PD-1 monoclonal antibody substituted with the amino acid(s) is 95% or more, preferably 98% or more, and more preferably 99% or more to that of anti-PD-1 monoclonal antibody having the original VH without any substitutions with the same amino acid(s).

Furthermore, examples of the anti-PD-1 monoclonal antibody of the present invention include those which contain a VH having each CDR comprising the specific amino acid sequence mentioned above, and in which the framework amino acid sequences of the VH is encoded by a specific germ-line gene or gene thereof with somatic mutation(s), and examples of which include a specific VH encoded by the specific germ-line gene or gene thereof with somatic mutation(s), as described about the above-mentioned "first arm specifically binding to PD-1."

Furthermore, in the anti-PD-1 monoclonal antibodies of the present invention, examples of those which have a VH containing each CDR in any one of the VH selected from the above (1a) to (4a) or (1b) to (5b), and in which the FR amino acid sequences are encoded by a specific germ-line gene or gene thereof with somatic mutation(s) include those having the VH comprising the amino acid sequence set forth in any one selected from SEQ ID Nos. 1 to 5. Furthermore, examples of such an anti-PD-1 monoclonal antibody include those having a VH amino acid sequence having at least 80%, preferably at least 90%, more preferably at least 95%, further preferably at least 98%, further more preferably at least 99% identity to the amino acid sequence set forth in any one selected from SEQ ID Nos. 1 to 5, and having the binding activity to PD-1 that is substantially the same as that of an anti-PD-1 monoclonal antibody having the original VH. Herein, the sentence "having the binding activity to PD-1 that is substantially the same as that of an anti-PD-1 monoclonal antibody having the original VH" means that it has 95% or more, preferably 98% or more, and more preferably 99% or more of the binding activity to PD-1 to that of the anti-PD-1 monoclonal antibody having the original VH.

Furthermore, other embodiments of the anti-PD-1 monoclonal antibody of the present invention also include an anti-PD-1 monoclonal antibody cross-competing for the binding to PD-1 with an anti-PD-1 monoclonal antibody having any one of the VH selected from the above-mentioned (1a) to (4a) or (1b) to (5b) or the VH amino acid sequence set forth in any one selected from SEQ ID Nos. 1 to 5, and an anti-PD-1 monoclonal antibody with which the binding to PD-1 is cross-competed by an anti-PD-1 monoclonal antibody having any one of the VH selected from the above-mentioned (1a) to (4a) or (1b) to (5b) or the VH comprising the amino acid sequence set forth in any one selected from SEQ ID Nos. 1 to 5.

Preferable features of the anti-PD-1 monoclonal antibody of the present invention include allowing the interaction between PD-1 and PD-L1, interaction between PD-1 and PD-L2, or both of the interactions, as well as the PD-1/CD3 bispecific antibody of the present invention.

Polynucleotide Encoding a PD-1/CD3 Bispecific Antibody

A polynucleotide encoding the PD-1/CD3 bispecific antibody comprises: (1) a polynucleotide encoding the heavy chain having the VH of the first arm specifically binding to PD-1, (2) a polynucleotide encoding the heavy chain having the VH of the second arm specifically binding to CD3, and (3) polynucleotides encoding the common light chains. Herein, the polynucleotide encoding the heavy chain having the VH of the first arm specifically binding to PD-1 comprises a polynucleotide encoding the VH of the first arm specifically binding to PD-1 and a polynucleotide encoding a constant region of the heavy chain having the VH. Similarly, a polynucleotide encoding the heavy chain having the VH of the second arm specifically binding to CD3 comprises a polynucleotide encoding the VH of the second arm specifically binding to CD3 and a polynucleotide encoding a constant region of the heavy chain having the VH.

The polynucleotide encoding the PD-1/CD3 bispecific antibody may be any polynucleotides as long as they encode each of parts constituting the PD-1/CD3 bispecific antibody, and may be any of genome DNA, cDNA, synthesis DNA, RNA, and DNA-RNA hybrid. As a codon encoding one amino acid, one to six types of codons are known. For example, Phe corresponds to TTT or TTC, Leu corresponds to TTA, TTG, CTT, CTC, CTA or CTG, Ile corresponds to ATT, ATC or ATA, Met correspond to ATG, Val corresponds to GTT, GTC, GTA or GTG, Ser corresponds to TCT, TCC, TCA or TCG, Pro corresponds to CCT, CCC, CCA or CCG, Thr corresponds to ACT, ACC, ACA or ACC; Ala corresponds to GCT, GCC, GCA or GCC, Tyr corresponds to TAT or TAC, His corresponds to CAT or CAC, Gln corresponds to CAA or CAG, Asn corresponds to AAT or AAC, Lys corresponds to AAA or AAG, Asp corresponds to GAT or GAC, Glu corresponds to GAA or GAG, Cys corresponds to TGT or TGC, Trp corresponds to TGG, Arg corresponds to CGT, CGC, CGA or CGC, Ser corresponds to AGT or AGC, Arg corresponds to AGA or AGG and Gly corresponds to GGT, GGC, GGA or GGC, respectively. Accordingly, the polynucleotide encoding the PD-1/CD3 bispecific antibody includes polynucleotides in which codons corresponding to each amino acid are arbitrarily combined. Preferable examples of the polynucleotide encoding the VH of the first arm specifically binding to PD-1 include a polynucleotide having the base sequence set forth in any one selected from SEQ ID Nos. 30 to 34 encoding the VHs of the PD1-1 to PD1-5 clones, respectively. Preferable examples of the polynucleotide encoding the VH of the second arm specifically binding to CD3 include a polynucleotide having the base sequence set forth in SEQ ID No. 40. Furthermore, preferable examples of the polynucleotide encoding a variable region of the common light chain include a polypeptide having the base sequence set forth in SEQ ID No. 35.
Pharmaceutical Use The PD-1/CD3 bispecific antibody of the present invention is useful for preventing, suppressing symptom progression or recurrence of, and/or treating autoimmune diseases or graft-versus-host diseases (GVHD).

Examples of diseases which can be prevented, of which symptom progression or recurrence can be suppressed, and/or which can be treated by the PD-1/CD3 bispecific antibody of the present invention include Behcet's disease, systemic lupus erythematosus, chronic discoid lupus erythematosus, multiple sclerosis (systemic scleroderma, and progressive systemic sclerosis), scleroderma, polymyositis, dermatomyositis, periarteritis nodosa (polyarteritis nodosa, and microscopic polyangiitis), aortitis syndrome (Takayasu's arteritis), malignant rheumatoid arthritis, rheumatoid arthritis, juvenile idiopathic arthritis, spondyloarthritis, mixed connective tissue disease, Sjogren's syndrome, adult Still's disease, vasculitis, allergic granulomatous vasculitis, hypersensitivity vasculitis, rheumatoid vasculitis, large vessel vasculitis, ANCA associated vasculitis (e.g., granulomatosis with polyangiitis and eosinophilic granulomatosis with polyangiitis), Cogan's syndrome, RS3PE, temporal arteritis, polymyalgia rheumatica, fibromyalgia, antiphospholipid antibody syndrome, eosinophilic fasciitis, IgG4-related disease (e.g., primary sclerosing cholangitis, autoimmune insulitis), Guillain-Barre syndrome, myasthenia gravis, chronic atrophic gastritis, autoimmune hepatitis, non-alcoholic steatohepatitis, primary biliary cirrhosis, Goodpasture's syndrome, rapidly progressive glomerulonephritis, megaloblastic anemia, autoimmune hemolytic anemia, pernicious anemia, autoimmune neutropenia, idiopathic thrombocytopenic purpura, Basedow disease (Graves' disease (hyperthyroidism)), Hashimoto disease, autoimmune adrenal insufficiency, primary hypothyroidism, Addison's disease (chronic hypoadrenocorticism), idiopathic Addison's disease, type I diabetes mellitus, slowly progressive type I diabetes mellitus (latent autoimmune diabetes in adult), focal scleroderma, psoriasis, psoriatic arthritis, bullous pemphigoid, pemphigus, pemphigoid, gestational herpes, linear IgA bullous dermatosis, acquired epidermolysis bullosa, alopecia areata, vitiligo, vitiligo vulgaris, neuromyelitis optica, chronic inflammatory demyelinating polyneuropathy, multifocal motor neuropathy, sarcoidosis, giant cell arteritis, amyotrophic lateral sclerosis, Harada disease, autoimmune optic neuropathy, idiopathic azoospermia, habitual abortion, inflammatory bowel disease (e.g., ulcerous colitis, and Crohn's disease), celiac disease, ankylosing spondylitis, severe asthma, chronic urticarial, transplantation immunity, familial mediterranean fever, eosinophilic chronic rhinosinusitis, dilated cardiomyopathy, systemic mastocytosis, or inclusion body myositis.

In the present invention, the term "treatment" means cure or improvement of a disease or symptom thereof. The term of "prevention" means that the onset of a disease or symptom thereof is prevented or delayed for a certain period. The term "suppression of symptom progression" means that the progress or deterioration of symptoms is suppressed to stop the progress of disease conditions. The meaning of "prevention" includes suppression of recurrence. The term "suppression of recurrence" means that the recurrence of certain disease or syndrome is prevented or a possibility of recurrence is reduced.

The PD-1/CD3 bispecific antibody of the present invention is usually administered systemically or locally through parenteral administration. Specific examples of such administration methods include injection administration, intranasal administration, transpulmonary administration, percutaneous administration, or the like. Examples of injection administration include intravenous injection, intramuscular injection, and intraperitoneal injection. For intravenous injection, drip intravenous infusion is preferable. The dose thereof varies depending on the age, body weight, symptoms, therapeutic effect, administration method, treating period, and the like. The single dose thereof for one adult patient is usually within a range of 0.1 μg/kg to 300 mg/kg and particularly preferably within a range of 0.1 mg/kg to 10 mg/kg, once to several times per day by parenteral administration, or within a range of one hour to 24 hours per day by intravenous sustaining administration. Needless to say, as mentioned above, since the dose varies depending on various conditions, the sufficient dose may be lower than the above-mentioned dose, or administration more than the above may be needed.

Formulation

When the PD-1/CD3 bispecific antibody of the present invention is formulated to be used as an injection or infusion solution for drip infusion, the injection or infusion solution may be in any form of an aqueous solution, suspension, or emulsion, or may be formulated as a solid agent together with pharmaceutically acceptable carrier such that that agent will be dissolved, suspended, or emulsified in a solvent at the time of use. Examples of the solvent that is used in the injection or the infusion solution for drip infusion include distilled water for injection, physiological saline, glucose solutions, and isotonic solutions (e.g., in which sodium chloride, potassium chloride, glycerin, mannitol, sorbitol, boric acid, borax, propylene glycol or the like is soluble.).

Herein, examples of the pharmaceutically acceptable carriers include stabilizers, solubilizers, suspending agents, emulsifiers, soothing agents, buffering agents, preservatives, antiseptic agents, pH adjusters, and antioxidants. As the stabilizers, various amino acids, albumin, globulin, gelatin, mannitol, glucose, dextran, ethylene glycol, propylene glycol, polyethylene glycol, ascorbic acid, sodium bisulfite, sodium thiosulfate, sodium edetate, sodium citrate, dibutylhydroxytoluene, or the like can be used. As the solubilizers, alcohols (e.g., ethanol), polyols (e.g., propylene glycol, polyethylene glycol and the like), nonionic surfactants (e.g., Polysorbate 20 (registered trademark), Polysorbate 80 (registered trademark), HCO-50 and the like), or the like can be used. As the suspending agents, glyceryl monostearate, aluminum monostearate, methyl cellulose, carboxymethyl cellulose, hydroxymethyl cellulose, sodium lauryl sulfate or the like can be used. As the emulsifiers, gum arabic, sodium alginate, tragacanth, or the like can be used. As the soothing agents, benzyl alcohol, chlorobutanol, sorbitol, or the like can be used. As the buffering agents, phosphate buffer, acetate buffer, borate buffer, carbonate buffer, citrate buffer, Tris buffer, glutamic acid buffer, epsilon aminocaproic acid buffer, or the like can be used. As the preservatives, methyl parahydroxybenzoate, ethyl parahydroxybenzoate, propyl parahydroxybenzoate, butyl parahydroxybenzoate, chlorobutanol, benzyl alcohol, benzalkonium chloride, sodium dehydroacetate, sodium edeate, boric acid, borax, or the like can be used. As the antiseptic agents, benzalkonium chloride, parahydroxybenzoic acid, chlorobutanol, or the like can be used. As the pH adjusters, hydrochloric acid, sodium hydroxide, phosphoric acid, acetic acid, or the like can be used. As the antioxidants, (1) aqueous antioxidants such as ascorbic acid, cysteine hydrochloride, sodium bisulfate, sodium metabisulfite, and sodium sulfite, (2) oil-soluble antioxidants such as ascorbyl palmitate, butylated hydroxy anisole, butylated hydroxy toluene, lecithin, propyl gallate, and α-tocopherol, and (3) metal chelating agents such as citric acid, ethylenediaminetetraacetic acid, sorbitol, tartaric acid, and phosphoric acid, or the like can be used.

The injection or infusion solution for drip infusion can be produced by performing sterilization in the final process, or aseptic manipulation, e.g., performing sterilization by filtration with a filter or the like, and subsequently filling an aseptic container. The injection or infusion solution for drip infusion may be used by dissolving the vacuum dried or lyophilized aseptic powder (which may include a pharmaceutically acceptable carrier powder) in an appropriate solvent at the time of use.

Combination Use or Combination Formulation

Furthermore, the PD-1/CD3 bispecific antibody of the present invention may be used in combination with other agent that is used for preventing, suppressing symptom progression, or recurrence of, and/or treating autoimmune disease. In the present invention, examples of administration form in such combination use with the other agents (combination use) may include a form of combination formulation containing both ingredients in one formulation, or a form being administered in separate formulations. Such combination use can supplement the preventive, symptom progress-suppressive, recurrence-suppressive, and/or therapeutic effect of the other agent, or can maintain or reduce the dose or frequency of administration of the other agent. In the present invention, in a case of separately administering the PD-1/CD3 bispecific antibody and the other agent, the both agents may be simultaneously administered for a certain period of time, and then only the PD-1/CD3 bispecific antibody or the other agent may be administered. Alternatively, the PD-1/CD3 bispecific antibody of the present invention may be firstly administered, and after the completion of the administration, the other agent may be administered. The other agent may be firstly administered, and then the PD-1/CD3 bispecific antibody of the present invention may be administered. The administration method may be the same as or different from each other. The present invention also can provide a kit containing a formulation containing the PD-1/CD3 bispecific antibody of the present invention and a formulation containing the other agent. The dose of the other agent can be appropriately selected based on the dose in clinical use. The other agent may be a combination of two or more kinds of arbitrary agents at an appropriate ratio. Examples of the other agent include not only those already known but also those newly discovered in the future.

For example, when the PD-1/CD3 bispecific antibody of the present invention is applied to prevention, suppression of symptom progression or recurrence and/or treatment of type I diabetes mellitus, it may be used in combination with, e.g., any one or more of agent(s) selected from an insulin preparation (e.g., human insulin, insulin glargine, insulin lispro, insulin detemir, insulin aspart, and the like.), sulfonylurea agent (e.g., glibenclamide, gliclazide, or glimepiride), quick-acting insulin secretion promoter (e.g., nateglinide), biguanide preparation (e.g., metformin), insulin resistance improving agent (e.g., pioglitazone), α-glucosidase inhibitor (e.g., acarbose, voglibose, and the like.), diabetic neuropathy therapeutic agent (e.g., epalrestat, mexiletine, imidapril, and the like.), GLP-1 analog preparation (e.g., liraglutide, exenatide, lixisenatide, and the like.), and DPP-4 inhibitor (e.g., sitagliptin, vildagliptin, alogliptin, and the like.), and the like.

Furthermore, for example, when the PD-1/CD3 bispecific antibody of the present invention is applied to prevention, suppression of symptom progression or recurrence and/or treatment of multiple sclerosis, it may be used in combination with any one or more of agent(s) selected from a steroid agent (e.g., cortisone acetate, hydrocortisone, hydrocortisone sodium phosphate, hydrocortisone sodium succinate, fludrocortisone acetate, prednisolone, prednisolone acetate, prednisolone sodium succinate, prednisolone butylacetate, prednisolone sodium phosphate, halopredone acetate, methylprednisolone, methylprednisolone acetate, methylprednisolone sodium succinate, triamsinolone, triamsinolone acetate, triamsinolone acetonide, dexamethasone, dexamethasone acetate, dexamethasone sodium phosphate, dexamethasone palmitate, paramethasone acetate, or betamethasone), interferon β-1a, interferon β-1 b, glatiramer acetate, mitoxantrone, azathioprine, cyclophosphamide, cyclosporin, methotrexate, cladribine, adrenocorticotropic hormone (ACTH), corticotropin, mizoribine, tacrolimus, fingolimod, or alemtuzumab, and the like.

Furthermore, for example, when the PD-1/CD3 bispecific antibody of the present invention is applied to prevention, suppression of symptom progression or recurrence and/or treatment of systemic lupus erythematosus, it may be used in combination with any one or more of agent(s) selected from a steroid agent (e.g., steroid agents mentioned above), immunosuppressive agent (e.g., cyclosporin, tacrolimus, or fingolimod), and belimumab.

For example, when the PD-1/CD3 bispecific antibody of the present invention is applied to prevention, suppression of symptom progression or recurrence and/or treatment of rheumatoid arthritis, it may be used in combination with any one or more of agent(s) selected from a steroid agent (e.g., the steroid agents mentioned above), anti-rheumatic agent (e.g., methotrexate, sulfasalazine, bucillamine, leflunomide, mizoribine, tacrolimus, and the like.), anti-cytokine agent (e.g., infliximab, adalimumab, tocilizumab, etanercept, golimumab, sertolizumab, and the like.), and abatacept, and the like.

In the case of applying the PD-1/CD3 bispecific antibody of the present invention to prevention, suppression of symptom progression or recurrence and/or treatment of other autoimmune diseases, the PD-1/CD3 bispecific antibody of the present invention may be used in combination with any one or more of the above-mentioned other agent(s).

The present invention will now be described in more detail by the following examples, but the scope of the present invention is not limited thereto. A person skilled in the art can make various changes and modifications, based on the description of the present invention, and such changes and modifications are also included in the present invention.

EXAMPLES

Example 1: Immunization of MeMo Mice Using Recombinant Human PD-1-Fc Fusion Protein As a method for obtaining the first arm specifically binding to PD-1 of the present invention, a method for immunizing MeMo mice (see WO2009/157771) with a recombinant human PD-1 protein is selected. The MeMo mice are those genetically modified such that a gene fragment including a non-recombinant human heavy chain V gene region, D gene region, and J gene region as well as a recombinant human κ light chain IgVκ1-39*01/IGJκ*01 germ-line gene is linked to a mouse constant region gene. By directly immunizing the MeMo mice with a target protein of an antibody, antibodies composed of heavy chains and common light chains, with diversity, can be produced.

Twelve 12- to 16-week-old MeMo MSSB/MS9 mice were immunized with recombinant human PD-1-Fc fusion protein (R&D Systems, serial number 1086-PD) which had been emulsified using Gerbu adjuvant MM (Gerbu Biotechnik, serial number #3001) at an interval of 14 days. On days 0, 14 and 28 after immunization, the recombinant human PD-1-Fc fusion protein was subcutaneously administered. At timing later than that, the recombinant human PD-1-Fc fusion protein dissolved in PBS was subcutaneously administered. On days 21, 35, 56, 77 and 98 after immunization, the antibody titer in serum was evaluated by flow cytometry using a human PD-1 forced-expressed HEK293 T cell lines. When the human PD-1 forced-expressed HEK293T cell lines were stained in 1000-fold diluted serum, mouse lymph tissue of which MFI value was not less than three times higher than that of the human PD-1 non-expressing HEK293T cell lines as a control was used for constructing a phage display library. Mice satisfying the criteria for constructing the library construct were additionally immunized with the recombinant PD-1-Fc fusion protein for three days from the evaluation date of the antibody titer, and of which the spleens and inguinal lymph nodes were collected. Mice in which the antibody titer in serum to human PD-1 and cynomolgus monkey PD-1 was 1/100 or more, and the antibody titer was not increased by additional immunization were also subjected to the same method, and then of which the spleens and inguinal lymph nodes were collected. RNA was extracted from those lymphoid tissues, and then cDNA synthesis was carried out.

Example 2: Construction of Phage Display Library for Obtaining Anti-PD-1 Antibody Having the First Arm Specifically Binding to PD-1 (Protein Immunization)

PCR reaction was carried out using DNA prepared in Example 1 and primers specific to immunoglobulin heavy chain variable region family. The obtained PCR product was digested with restriction enzymes SfiII and XhoI, and inserted into MV1473 phagemid vector [having a gene (human κ light chain IgVκ1-39*01/IGJκ1*01 germ-line gene) encoding the common light chain] digested with the same restriction enzymes to construct the library.

Example 3: Screening of Anti-PD-1 Antibody Having the First Arm Specifically Binding to PD-1

Phage selection based on the binding property to PD-1 was carried out using plates coated with human PD-1-Fc fusion protein, human PD-1-His tag fusion protein, cynomolgus monkey PD-1-His tag fusion protein or mouse PD-1-His tag fusion protein. When using the human PD-1-Fc fusion protein, during incubation with phage, human IgG (SIGMA, serial number 14506) was added to absorb Fc reactive clones. The binding phages which can bind to human PD-1, cynomolgus monkey PD-1 and mouse PD-1 were enriched. The phages which can bind to cynomolgus monkey PD-1 were enriched by using selections on cynomolgus monkey PD-1 expressing HEK293 T cell lines. *Escherichia coli* strain TG1 clones transformed with phages obtained by selection were obtained to produce a master plate.

Furthermore, based on the binding property to PD-1 on a plate coated with human PD-1-Fc fusion protein, phage selection was carried out using a periplasmic space extract of the clones obtained by the above-mentioned selection. Note here that as the criteria for selection, clones with signals three times more than that ($OD_{450}$ value) obtained from negative control wells (PBS) were defined as positive clones.

Example 4: DNA Sequence for Anti-PD-1 Antibody Candidate Clones Having the First Arm Specifically Binding to PD-1

DNA sequence for a heavy chain variable region gene of positive clones obtained by screening in Example 3 was carried out. Analyzed DNA sequences were classified into super clusters (a group having the same length CDR3, and an amino acid sequence of CDR3 is 70% or more homologous) and clusters (a group in which amino acid sequences of the heavy chain CDR3 are the same). Nine hundred and twenty-four clones were obtained, which were classified into 146 types super clusters and 194 types clusters.

Example 5: Screening Based on Binding Property Evaluation to PD-1 Expressing Cells From each of the classified super clusters, anti-PD-1 monoclonal antibody clones satisfying the following conditions were screened to isolate them:
(1) somatic mutation(s) was/were introduced into CDR region(s) with high frequency;
(2) a germ-line gene of VH with high frequency in use was included, and
(3) a high signal was obtained in the binding property screening to human PD-1-Fc fusion protein.

The evaluation was carried out by detecting the binding to human PD-1-expressing CHO-S cell lines and cynomolgus monkey PD-1-expressing CHO-S cell lines with an anti-mouse IgG polyclonal antibody, using Fab fragments contained in these periplasmic space extracts. Among the evaluated 117 clones (105 types of clusters), It was recognized that 22 clones including anti-PD-1 monoclonal antibody PD1-1, PD1-2, PD1-3 and PD1-4 clones can bind to the human PD-1 expressing CHO-S cell lines.

Example 6: Production of an Amino Acid Substituted Product of Anti-PD-1 Monoclonal Antibody Having the First Arm Specifically Binding to PD-1

The PD1-1 and PD1-4 clone include a deamidation motif (Asn-Gly) in the framework 4 of the heavy chain variable region, respectively. In order to obtain the first arm with reduced risk of deamidation, a variant in which the deamidation motif has been converted was produced. The PD1-5 clone was produced such that asparagine (Asn) at position 119 according to the EU numbering system of the PD1-4 clone was altered to glutamine by a well-known site-specific mutation method, which was isolated. The binding property to human PD-1 expressing CHO-S cells of that clone was equal to that of the PD1-4 clone.

Example 7: Screening of Anti-CD3 Monoclonal Antibodies Having the Second Arm Specifically Binding to CD3

In order to obtain a Fab binding to CD3 having more stability and further reduced charge heterogeneity, an anti-CD3 antibody having the "second arm specifically binding to CD3" of the present invention was obtained by the following method, using the anti-CD3 antibody clone having the VH of the anti-CD3 antibody 15C3 clone described in WO2005/118635 and IGVK1-39/JK1 common light chain.

By converting the underlined 55th glycine in the VH amino acid sequence of 15C3 shown in FIG. 10, into alanine, the anti-CD3 antibody CD3-1 clone, having the binding property to human CD3 equal to that clone and having improved charge heterogeneity was obtained.

Furthermore, in order to obtain a plurality of Fabs binding to CD3 to improve the VH/VL interaction with the common light chain (IgVκ1-39*01/IGJκ*01) based on the VH of the CD3-1 clone, a phage display library expressing a plurality of Fabs including VH variants of CD3-1 clone in which that amino acid residue has been substituted was constructed. This phage library was subjected to screening using HBP-ALL cells or recombinant human CD3-Fc protein. A phages binding to the recombinant human CD3ε-Fc protein were chemically eluted, and used for reinfection to bacteria. A plurality of survived bacterial colony were extracted, then phages therefrom were extracted, and then screened by flow cytometry, based on the binding to CD3 expressed on cell surface. All of the phages binding to CD3 were subjected to colony PCR to amplify cDNA encoding its VH, and DNA sequences thereof were determined.

As a result, the obtained anti-CD3 antibody CD3-2 clone having the VH comprising the amino acid sequence set forth in SEQ ID No. 36 showed the binding property to CD3 and charge homogeneity equivalent to those of the CD3-1 clone.

Example 8: Preparation of the PD-1/CD3 Bispecific Monoclonal Antibody

An expression vector expressing each heavy chain of the first arm specifically binding to PD-1 was produced by linking DNAs encoding heavy chain variable regions of the anti-PD-1 monoclonal antibody PD1-1 to PD1-5 and PD1-6 clones, respectively, selected in Example 5, to DNAs encoding IgG$_1$ heavy chain constant regions, respectively. On the other hand, an expression vector expressing a heavy chain of the second arm specifically binding to CD3 was produced by linking a DNA encoding a heavy chain variable region of the anti-CD3 monoclonal antibody CD3-2 clone selected in Example 7 to a DNA encoding an IgG$_1$ heavy chain constant region. Herein, as genes expressing such heavy chain constant regions, as to the first arm specifically binding to PD-1, a gene expressing an Fc region having L351D/L368E variation (DE variation) was used. As to the second arm specifically binding to CD3, a gene expressing an Fc region having L351K/T366K variation (KK variation) was used. These expression vectors were constructed so as to further include a gene encoding the IGVK1-39/JK1 common light chain such that it will be expressed together. Furthermore, genes expressing these heavy chain constant regions have been modified to express those in which leucine at position 235 was substituted with glycine and further glycine at position 236 was substituted with arginine in the heavy chain constant region, in order to eliminate the Fc effector activity, and further lysine at a position 447 at C-terminal of the heavy chain constant region was deleted, in order to avoid processing after translation, were used. Both of these expression vectors were gene-transferred into Free Style 293F cell to produce antibodies in culture supernatants. The culture supernatants were collected and then treated by protein A affinity chromatography, to purify the PD1-1(Bi) clone, the PD1-2(Bi) clone, the PD1-3(Bi) clone, the PD1-4(Bi) clone, and the PD1-5(Bi) clone of the PD-1/CD3 bispecific monoclonal antibody of the present invention, respectively. Furthermore, the PD1-6(Bi) clone was also produced by the same method. Note here that, in that these PD-1/CD3 bispecific monoclonal antibody clones have the first arms specifically binding to PD-1 derived from the anti-PD-1 monoclonal antibody: PD1-1, PD1-2, PD1-3, PD1-4, and PD1-5 clones, as well as PD1-6 clone, used in production thereof, they correspond to those anti-PD-1 monoclonal antibody clones, respectively.

Example 9: Evaluation of the Binding Property of the PD-1/CD3 Bispecific Monoclonal Antibody By Biacore assay using human IgG1-Fc fused human PD-1 extracellular recombinant protein or 6×His tag fused cynomolgus monkey PD-1 extracellular recombinant protein, the binding affinities to each PD-1 recombinant protein of the first arms of the PD-1/CD3 bispecific monoclonal antibodies obtained in Example 8 were evaluated. Note here that for immobilization of the recombinant proteins, Series S Sensor Chip CM5 Sensor Chip (GE Health Care, serial number 29-1049-88) was used. Similarly, by the Biacore assay using a human IgG1-Fc fused CD3δ/CD3ε extracellular recombinant protein, the binding affinities to CD3 of the second arms of the antibodies were evaluated. FIG. 11 shows the binding affinity (Kd value) to PD-1 of the first arm and the binding affinity to CD3δ/CD3ε of the second arm with respect to each clone.

Example 10: Verification of the Binding Property of the PD-1/CD3 Bispecific Monoclonal Antibody It was verified that the PD-1/CD3 bispecific monoclonal antibodies obtained in Example 8 specifically can bind to PD-1 and CD3, simultaneously.

Firstly, the PD1-1(Bi) to PD1-6(Bi) clones were added to human PD-1 deficient Jurkat cell lines (human T cell line) expressing human CD3, respectively, and which were incubated on ice for 15 minutes. After those cells were washed, soluble PD-1 recombinant proteins (R&D systems, serial number 1086-PD-050) labeled with 3-fold amount of biotin were added, and incubated on ice for 15 minutes. After those cells were washed, 100 µL of 1.25 µg/mL Alexa Fluor 488-labeled streptavidin (BioLegend, serial number 405235) was added to them, and which were incubated on ice for 15 minutes. After those cells were washed, a binding amount of the soluble PD-1 recombinant protein was evaluated by flow cytometry. FIG. 12 shows results of the assay.

All of the clones bound to PD-1 and CD3 simultaneously. Note here that nonspecific binding in this binding system was not detected.

Figure 13:
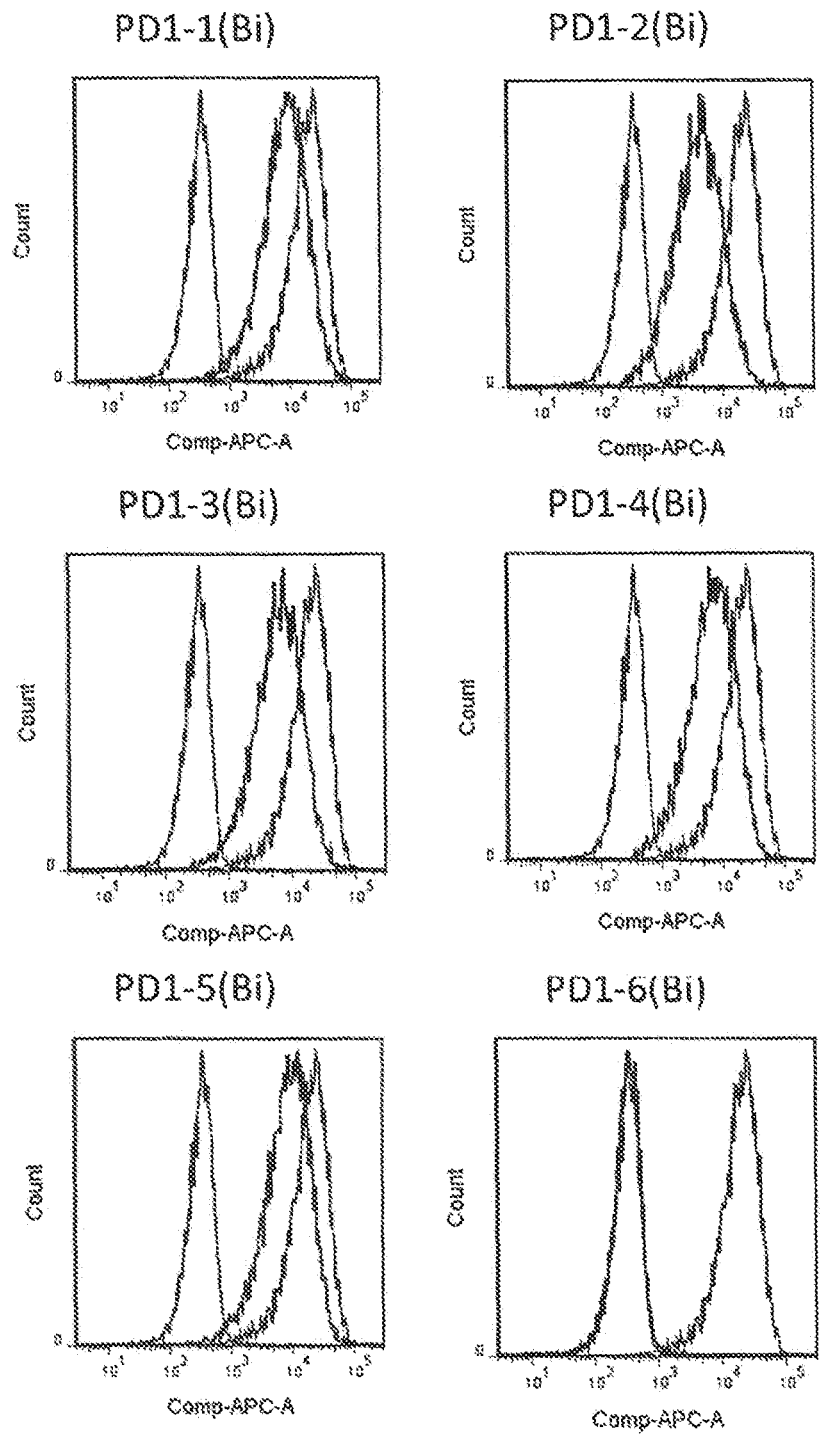
FIG. 13 shows flow cytometry demonstrating influence on the PD-1/PD-L1 interaction of each PD-1/CD3 bispecific monoclonal antibody clone.

Example 11: Evaluation of the Binding Property of the First Arm of the PD-1/CD3 Bispecific Monoclonal Antibody In order to evaluate effects on the PD-1/PD-L1 binding of the first arms of the PD-1/CD3 bispecific monoclonal antibodies obtained in Example 8, a competitive binding assay with respect to the binding to PD-1 of the bispecific monoclonal antibody clones and soluble PD-L1 recombinant proteins was carried out. Firstly, the PD1-1(Bi) to PD1-6(Bi) clones were added to human PD-1 expressing CHO-S cell lines, respectively, and which were incubated on ice for 30 minutes. The soluble PD-L1 recombinant proteins (R&D systems, serial number 156-B7-100) labeled with ¹⁄₂₀ amount of biotin were added to them, and which were incubated on ice for 30 minutes. After those cells were washed, PE-labeled streptavidin (BD Pharmingen, serial number 554061) was added to them, and which were incubated on ice for 30 minutes. After those cells were washed, a binding amount of the soluble PD-L1 recombinant proteins was evaluated by flow cytometry. FIG. 13 shows its results of the assay.

Although there are the clones PD1-1(Bi) to PD1-5(Bi) at the amount of 20 times more than that of the soluble PD-L1 recombinant protein, they allowed the soluble PD-L1 recombinant protein to bind to PD-1. On the other hand, PD1-6(Bi) completely inhibited the binding to PD-1 of the soluble PD-L1 recombinant protein in the same conditions.

Figure 14:
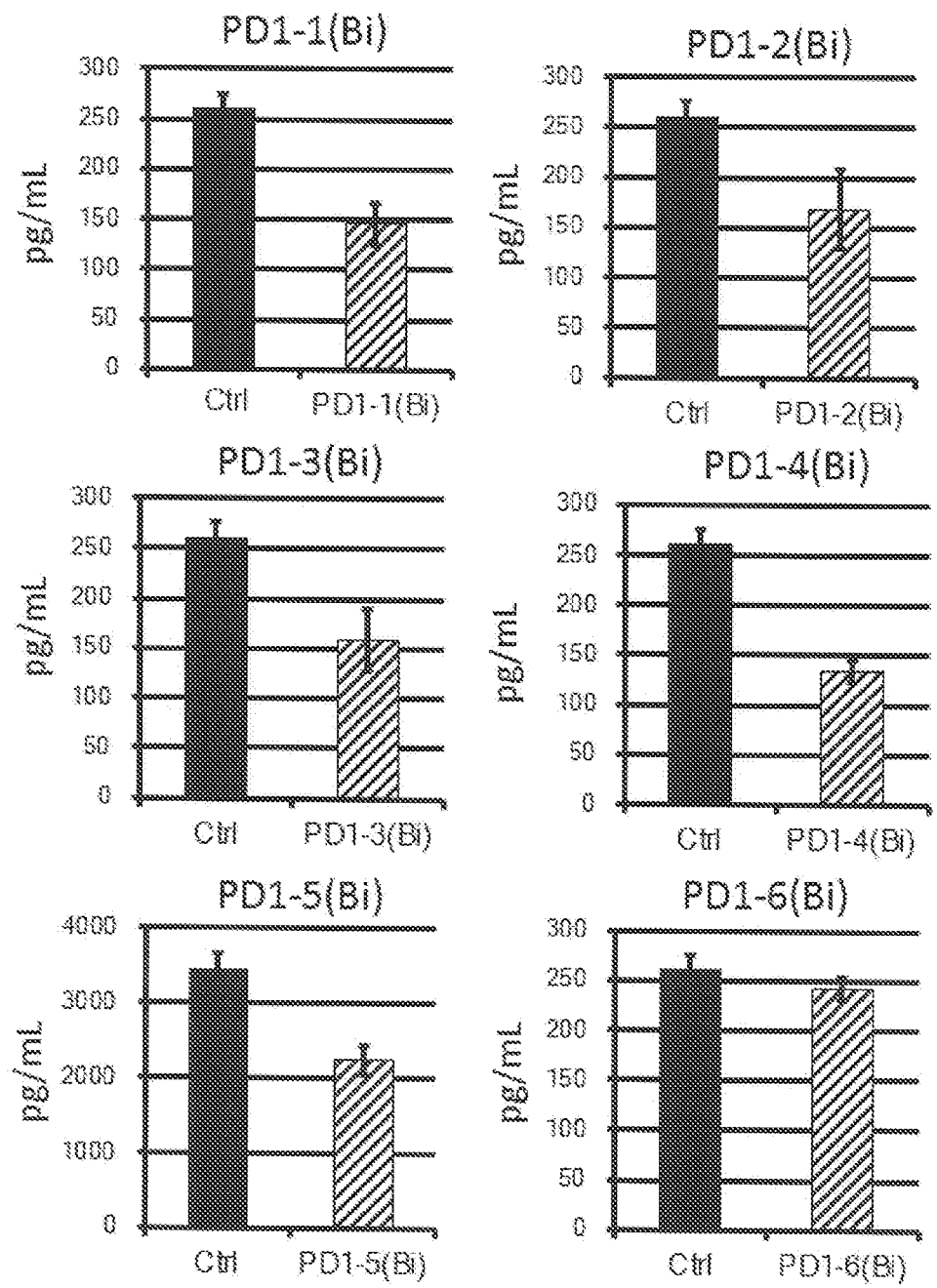
FIG. 14 shows effects on IFN-γ production from activated human T cells of each PD-1/CD3 bispecific monoclonal antibody clone. Note here that in the drawing, "Ctrl" represents control group.

Example 12: In Vitro Suppressive Effects of the PD-1/CD3 Bispecific Monoclonal Antibody on Activated CD4 T Cells Suppressive effects of activated T cells on IFN-γ production were evaluated using CD4 positive T cells derived from healthy human peripheral blood (LONZA, serial number 2W-200) (human T cells). Human T cells were seeded on a cell culture plate on which anti-human TCRVβ8 antibodies (Thermo Scientific, serial number TCR1750) have been solid-phased, anti-human CD28 antibodies (BioLegend, serial number 302923) were added thereto, and subjected to activation treatment for 72 hours. Next, the human T cells that have been subjected to activation treatment were cultured overnight in a fresh medium containing 100 Units/mL human IL-2 (R&D systems, serial number 202-IL). Furthermore, the collected human T cells were seeded on another cell culture plate on which anti-human TCRVβ8 antibodies have been solid-phased, and anti-human CD28 antibodies were added thereto, as well, and then activation treatment was carried out again. At this time, the PD1-1(Bi) to PD1-6(Bi) clones were added thereto, respectively, and then IFN-γ contained in the culture supernatant 96 hours after the reactivation treatment was quantified by ELISA (pg/mL). FIG. 14 shows its results. Suppressive activities of IFN-γ production of the PD1-1(Bi) to PD1-5(Bi) clones were confirmed. Suppressive activity of IFN-γ production of the PD1-6(Bi) clone trends to decrease more than other clones. An antibody obtained by immunization of tetanus toxoid by the same technique as that to obtain the first arm, which is a non-specific antibody, was used as a control antibody.

Example 13: In Vivo Effects of the PD-1/CD3 Bispecific Monoclonal Antibody on Experimental Allergic Encephalomyelitis Mouse Model (EAE Model)

Figure 15:
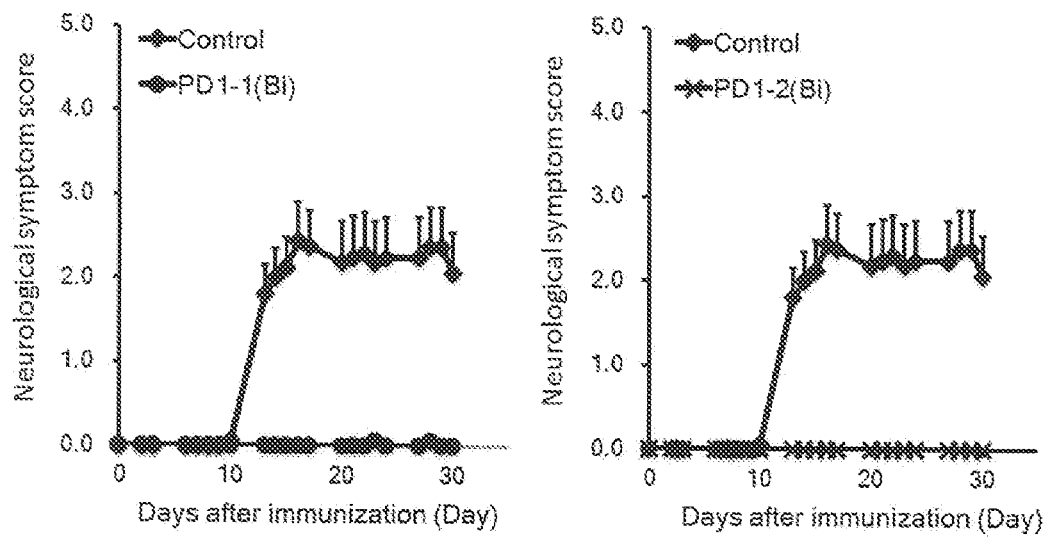
FIG. 15 shows therapeutic effects of the PD-1/CD3 bispecific monoclonal antibody clones (PD1-1(Bi) and PD1-2 (Bi)) in an experimental allergic encephalomyelitis mouse model (EAE model).
Figure 16:
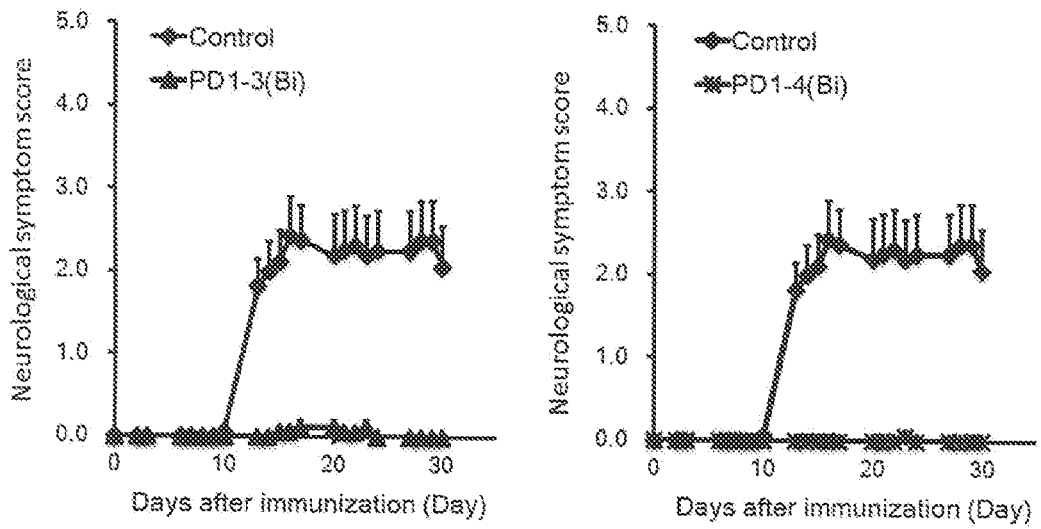
FIG. 16 shows therapeutic effects of the PD-1/CD3 bispecific monoclonal antibody clones (PD1-3(Bi) and PD1-4 (Bi)) in an experimental allergic encephalomyelitis mouse model.
Figure 17:
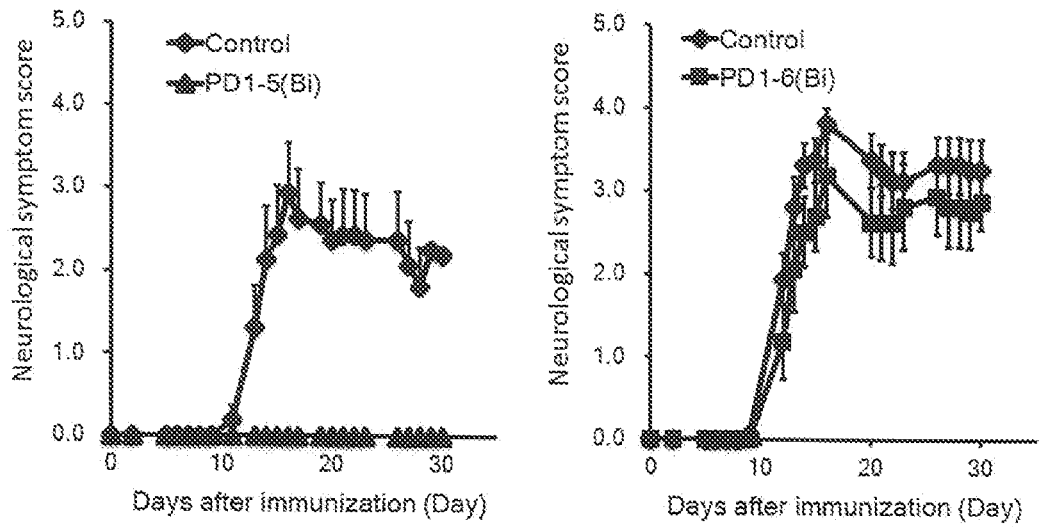
FIG. 17 shows therapeutic effects of the PD-1/CD3 bispecific monoclonal antibody clones (PD1-5(Bi) and PD1-6 (Bi)) in an experimental allergic encephalomyelitis mouse model.

In vivo effects of the PD-1/CD3 bispecific monoclonal antibody of the present invention were evaluated in an EAE model using a human CD3ε/human PD-1 knock-in C57BL/6 mice in which CD3c gene and PD-1 gene have been substituted with human CD3ε gene and human PD-1 gene, respectively. Killed *Mycobacterium tuberculosis* H37Ra (BD Biosciences, serial number 231141) and incomplete Freund's adjuvant (BD Biosciences, serial number 263910) were mixed with each other to prepare a complete Freund's adjuvant (CFA) containing 4 mg/mL killed *Mycobacterium tuberculosis* H37Ra. 1 mg/mL MOG peptide (ANASPEC, serial number AS-60130) and the equal amount of CFA were mixed with each other to prepare a emulsion as an eliciting agent of the EAE model. The 200 μL eliciting agents were subcutaneously administered to tail head of the C57BL/6 mice. On the treatment day of the immunization and on day 2, 200 μL of 1 μg/mL of pertussis toxin (SIGMA-ALDRICH, serial number P7208) were administered in tail vein, respectively. Next, on day 6 and 7 of immunization, 2 mg/kg of the PD1-1 (Bi) to PD1-6 (Bi) clones were intraperitoneally administered to the C57BL/6 mice once a day, respectively. The neurological symptoms after the immunization were evaluated in accordance with the method of Onuki, et al. (Onuki M, et al., Microsc Res Tech 2001; 52: 731-9). The degrees of neurological symptoms were scored (normal: score 0, tail relaxation: score 1, hind limb partial paralysis: score 2, hind limb paralysis: score 3, forelimb paralysis: score 4, and dying or death: score 5). If a plurality of neurological symptoms were observed, the higher score was employed as the neurological symptom on the evaluation day. The neurological symptom of died mice was scored to 5 until completion of the observation. FIGS. 15 to 17 show its evaluation results. Note here that the human CD3ε/human PD-1 knock-in C57BL/6 mice were produced by mating the human CD3ε knock-in mouse produced, according to the method described in Genesis. 2009 June; 47(6): 414-22, with the human PD-1 knock-in mouse by a well-known method.

In the EAE model, the onset of the neurological symptoms was remarkably suppressed with respect to any of the PD1-1 to PD1-5(Bi) clones, but significant suppressive effect was not observed with respect to the PD1-6(Bi) clone.

Figure 18:
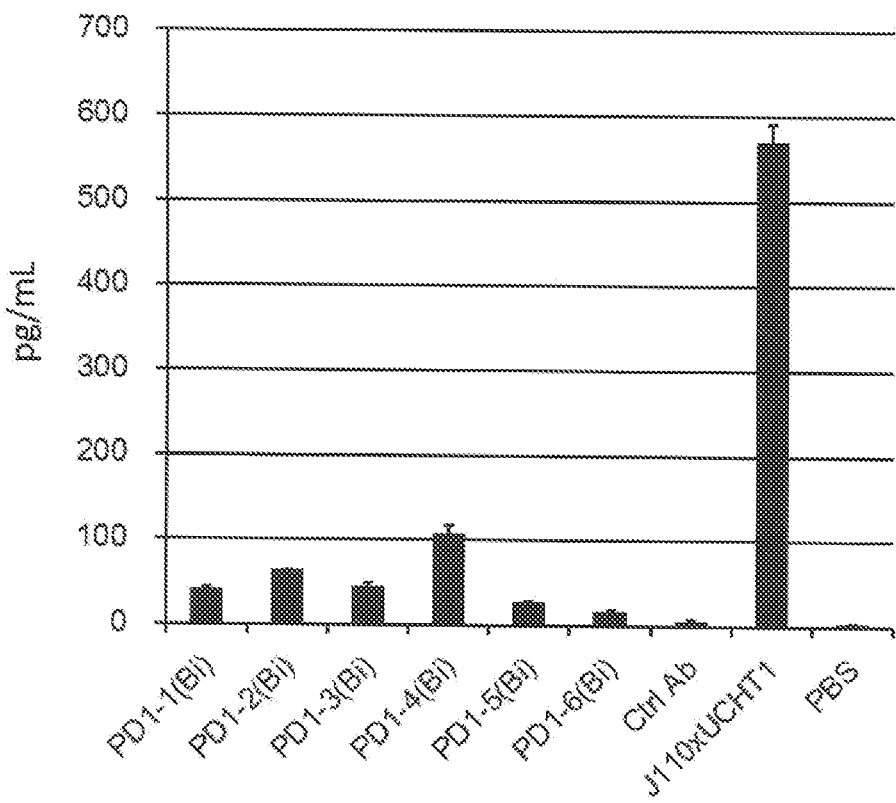
FIG. 18 shows the results of effect on cytokine production from human peripheral blood mononuclear cell of each PD-1/CD3 bispecific monoclonal antibody clone.

Example 14: Evaluation of In Vitro Effect of PD-1/CD3 Bispecific Monoclonal Antibody on Cytokine Release from Human Peripheral Blood Monocyte For the purpose of analyzing the cytokine releasing activity of the PD-1/CD3 bispecific monoclonal antibody, the experiment in which the PD-1/CD3 bispecific monoclonal antibody clones of the present invention or the PD-1/CD3 bispecific scDb (J110×UCHT1) disclosed in Patent Literature 2 are added to human peripheral blood mononuclear cells (hereinafter, referred to as "human PBMC") was carried out. Each clone of the PD-1/CD3 bispecific monoclonal antibodies and J110×UCHT1 were added to human PBMC (LONZA, serial number CC-2702) such that their concentrations were 30 μg/mL and 10 μg/mL, respectively, and then which were cultured for 24 hours. After culture for 24 hours, each IL-2 contained in their culture supernatants was quantified by multiplex immunoassay (BIO-RAD, serial number M50000007A). FIG. 18 shows its results. Note here that the amount of IL-2 production (pg/mL) in the figure are presented by mean value±standard error (N=3).

J110×UCHT1 remarkably induced IL-2 production. However, IL-2 productions with respect to any clone of the PD-1/CD3 bispecific monoclonal antibodies were low.

Example 15: Evaluation of Cross-Competitive Activity for Binding to PD-1 of Each Clone of the PD-1/CD3 Bispecific Monoclonal Antibodies with the PD1-5(Bi)

Cross-competition assay was conducted to evaluate cross-competitive activity for binding to PD-1 of each PD1-1(Bi) to PD1-5(Bi) clones of the PD-1/CD3 bispecific monoclonal antibody, obtained in Example 8, with the PD1-5(Bi).

Figure 19:
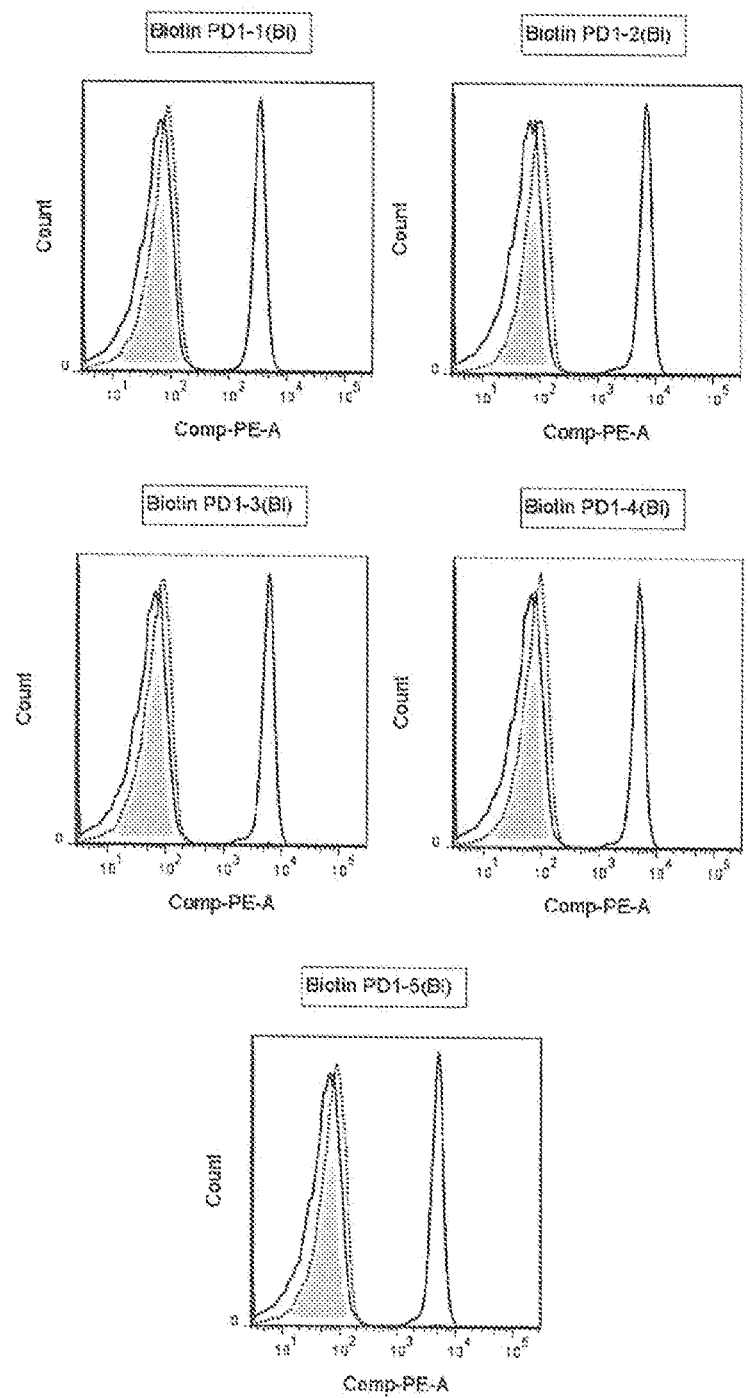
FIG. 19 shows the cross-competitive activity of PD1-5 (Bi) against the binding to PD-1 of each PD-1/CD3 bispecific monoclonal antibody clone.

At first, the PD1-5(Bi) clone was added to human PD-1-expressing CHO-S line cells, then which were incubated on ice for twenty minutes. Further, one-hundredth amount of the biotin-labeled clones PD1-1(Bi) to PD1-5(Bi) compared to that of the already-added PD1-5(Bi) clone were added to those cells, respectively, then which were incubated on ice for 20 minutes. Those cells were washed, to which PE-labeled streptavidin (BD Pharmingen, model number 554061) was added, and then were incubated on ice for 20 minutes. After washing those cells, the binding amount of the biotin-labeled clones PD1-1(Bi) to PD1-5(Bi) were measured using flow cytometry. FIG. 19 shows that result.

It was demonstrated that the PD1-5(Bi) clone can inhibit each binding to PD-1 of the PD1-1(Bi) to PD1-5(Bi) clones, and thus that the PD1-5(Bi) clone can cross-compete with their binding to PD-1.

INDUSTRIAL APPLICABILITY

The PD-1/CD3 bispecific antibody or an antibody fragment thereof of the present invention is useful for preventing, suppressing symptom progression or recurrence of, and/or treating autoimmune diseases or graft-versus-host diseases (GVHD).

Sequence Listing

The invention claimed is:

1. A bispecific antibody specifically binding to PD-1 and CD3 or an antibody fragment thereof, comprising a first arm specifically binding to PD-1 and a second arm specifically binding to CD3,
wherein the first arm specifically binding to PD-1 comprises any one of VH selected from (A)-(E) and a VL of (F):
(A) a VH having
 (a) a VH-CDR1 comprising the amino acid sequence set forth in SEQ ID NO: 6;
 (b) a VH-CDR2 comprising the amino acid sequence set forth in SEQ ID NO: 7; and
 (c) a VH-CDR3 comprising the amino acid sequence set forth in SEQ ID NO: 8;
(B) a VH having
 (a) a VH-CDR1 comprising the amino acid sequence set forth in SEQ ID NO: 9;
 (b) a VH-CDR2 comprising the amino acid sequence set forth in SEQ ID NO: 10; and
 (c) a VH-CDR3 comprising the amino acid sequence set forth in SEQ ID NO: 11;
(C) a VH having
 (a) a VH-CDR1 comprising the amino acid sequence set forth in SEQ ID NO: 12;
 (b) a VH-CDR2 comprising the amino acid sequence set forth in SEQ ID NO: 13; and
 (c) a VH-CDR3 comprising the amino acid sequence set forth in SEQ ID NO: 14;
(D) a VH having
 (a) a VH-CDR1 comprising the amino acid sequence set forth in SEQ ID NO: 15;
 (b) a VH-CDR2 comprising the amino acid sequence set forth in SEQ ID NO: 16; and
 (c) a VH-CDR3 comprising the amino acid sequence set forth in SEQ ID NO: 17; and
(E) a VH having
 (a) a VH-CDR1 comprising the amino acid sequence set forth in SEQ ID NO: 18;
 (b) a VH-CDR2 comprising the amino acid sequence set forth in SEQ ID NO: 19; and
 (c) a VH-CDR3 comprising the amino acid sequence set forth in SEQ ID NO: 20; and
(F) a VL having
 (a) a VL-CDR1 comprising the amino acid sequence set forth in SEQ ID NO: 26;
 (b) a VL-CDR2 comprising the amino acid sequence set forth in SEQ ID NO: 27; and
 (c) a VL-CDR3 comprising the amino acid sequence set forth in SEQ ID NO: 28; and
wherein the second arm specifically binding to CD3 comprises a VH of (G) and a VL of (H):
(G) a VH having
 (a) a VH-CDR1 comprising the amino acid sequence set forth in SEQ ID NO: 37;
 (b) a VH-CDR2 comprising the amino acid sequence set forth in SEQ ID NO: 38; and
 (c) a VH-CDR3 comprising the amino acid sequence set forth in SEQ ID NO: 39; and
(H) a VL having
 (a) a VL-CDR1 comprising the amino acid sequence set forth in SEQ ID NO: 26;
 (b) a VL-CDR2 comprising the amino acid sequence set forth in SEQ ID NO: 27; and
 (c) a VL-CDR3 comprising the amino acid sequence set forth in SEQ ID NO: 28.

2. The bispecific antibody specifically binding to PD-1 and CD3 or antibody fragment thereof according to claim 1, wherein
(i) the VH of the first arm specifically binding to PD-1 has:
 (a) the VH-CDR1 comprising the amino acid sequence set forth in SEQ ID NO: 6,
 (b) the VH-CDR2 comprising the amino acid sequence set forth in SEQ ID NO: 7, and
 (c) the VH-CDR3 comprising the amino acid sequence set forth in SEQ ID NO: 8; and
(ii) the VH of the second arm specifically binding to CD3 has:
 (a) the VH-CDR1 comprising the amino acid sequence set forth in SEQ ID NO: 37,
 (b) the VH-CDR2 comprising the amino acid sequence set forth in SEQ ID NO: 38, and
 (c) the VH-CDR3 comprising the amino acid sequence set forth in SEQ ID NO: 39.

3. The bispecific antibody specifically binding to PD-1 and CD3 or antibody fragment thereof according to claim 1, wherein
(i) the VH of the first arm specifically binding to PD-1 has:
 (a) the VH-CDR1 comprising the amino acid sequence set forth in SEQ ID NO: 9,
 (b) the VH-CDR2 comprising the amino acid sequence set forth in SEQ ID NO: 10, and
 (c) the VH-CDR3 comprising the amino acid sequence set forth in SEQ ID NO: 11; and
(ii) the VH of the second arm specifically binding to CD3 has:
 (a) the VH-CDR1 comprising the amino acid sequence set forth in SEQ ID NO: 37,
 (b) the VH-CDR2 comprising the amino acid sequence set forth in SEQ ID NO: 38, and
 (c) the VH-CDR3 comprising the amino acid sequence set forth in SEQ ID NO: 39.

4. The bispecific antibody specifically binding to PD-1 and CD3 or antibody fragment thereof according to claim 1, wherein
(i) the VH of the first arm specifically binding to PD-1 has
 (a) the VH-CDR1 comprising the amino acid sequence set forth in SEQ ID NO: 12,
 (b) the VH-CDR2 comprising the amino acid sequence set forth in SEQ ID NO: 13, and
 (c) the VH-CDR3 comprising the amino acid sequence set forth in SEQ ID NO: 14; and
(ii) the VH of the second arm specifically binding to CD3 has:
 (a) the VH-CDR1 comprising the amino acid sequence set forth in SEQ ID NO: 37,
 (b) the VH-CDR2 comprising the amino acid sequence set forth in SEQ ID NO: 38, and
 (c) the VH-CDR3 comprising the amino acid sequence set forth in SEQ ID NO: 39.

5. The bispecific antibody specifically binding to PD-1 and CD3 or antibody fragment thereof according to claim 1, wherein
(i) the VH of the first arm specifically binding to PD-1 has:
 (a) the VH-CDR1 comprising the amino acid sequence set forth in SEQ ID NO: 15,
 (b) the VH-CDR2 comprising the amino acid sequence set forth in SEQ ID NO: 16, and
 (c) the VH-CDR3 comprising the amino acid sequence set forth in SEQ ID NO: 17; and (ii) the VH of the second arm specifically binding to CD3 has:
(a) the VH-CDR1 comprising the amino acid sequence set forth in SEQ ID NO: 37,
(b) the VH-CDR2 comprising the amino acid sequence set forth in SEQ ID NO: 38, and
(c) the VH-CDR3 comprising the amino acid sequence set forth in SEQ ID NO: 39.

6. The bispecific antibody specifically binding to PD-1 and CD3 or antibody fragment thereof according to claim 1, wherein
(i) the VH of the first arm specifically binding to PD-1 has:
(a) the VH-CDR1 comprising the amino acid sequence set forth in SEQ ID NO: 18,
(b) the VH-CDR2 comprising the amino acid sequence set forth in SEQ ID NO: 19, and
(c) the VH-CDR3 comprising the amino acid sequence set forth in SEQ ID NO: 20; and
(ii) the VH of the second arm specifically binding to CD3 has:
(a) the VH-CDR1 comprising the amino acid sequence set forth in SEQ ID NO: 37,
(b) the VH-CDR2 comprising the amino acid sequence set forth in SEQ ID NO: 38, and
(c) the VH-CDR3 comprising the amino acid sequence set forth in SEQ ID NO: 39.

7. The bispecific antibody specifically binding to PD-1 and CD3 or antibody fragment thereof according to claim 1, wherein an FR1, an FR2 and an FR3 regions of the VH of the first arm specifically binding to PD-1 correspond to an amino acid sequence encoded by a germline V gene IGHV7-4-1 with one or more somatic mutations, and an FR4 region comprises an amino acid sequence encoded by a germ-line J gene JH6c with one or more somatic mutations, excluding the amino acid sequence included in the VH-CDR3 region.

8. The bispecific antibody specifically binding to PD-1 and CD3 or antibody fragment thereof according to claim 1, wherein the VH of the first arm specifically binding to PD-1 comprises the amino acid sequence set forth in any one selected from SEQ ID NO: 1, SEQ ID NO: 2, SEQ ID NO: 3, SEQ ID NO: 4, and SEQ ID NO: 5, or an amino acid sequence having at least 80% identity to VH amino acid sequence thereof.

9. The bispecific antibody specifically binding to PD-1 and CD3 or antibody fragment thereof according to claim 1, wherein the VH of the second arm specifically binding to CD3 comprises the amino acid sequence set forth in SEQ ID NO: 36, or an amino acid sequence having an identity of at least 80% to VH amino acid sequence thereof.

10. The bispecific antibody specifically binding to PD-1 and CD3 or antibody fragment thereof according to claim 1, wherein the VH of the first arm specifically binding to PD-1 comprises the amino acid sequence set forth in any one selected from SEQ ID NO: 1, SEQ ID NO: 2, SEQ ID NO: 3, SEQ ID NO: 4, and SEQ ID NO: 5; and the VH of the second arm specifically binding to CD3 comprises the amino acid sequence set forth in SEQ ID NO: 36.

11. The bispecific antibody specifically binding to PD-1 and CD3 or antibody fragment thereof according to claim 3, wherein the VH of the first arm specifically binding to PD-1 comprises the amino acid sequence set forth in SEQ ID NO: 1; and the VH of the second arm specifically binding to CD3 comprises the amino acid sequence set forth in SEQ ID NO: 36.

12. The bispecific antibody specifically binding to PD-1 and CD3 or antibody fragment thereof according to claim 4, wherein the VH of the first arm specifically binding to PD-1 comprises the amino acid sequence set forth in SEQ ID NO: 2; and the VH of the second arm specifically binding to CD3 comprises the amino acid sequence set forth in SEQ ID NO: 36.

13. The bispecific antibody specifically binding to PD-1 and CD3 or antibody fragment thereof according to claim 5, wherein the VH of the first arm specifically binding to PD-1 comprises the amino acid sequence set forth in SEQ ID NO: 3; and the VH of the second arm specifically binding to CD3 comprises the amino acid sequence set forth in SEQ ID NO: 36.

14. The bispecific antibody specifically binding to PD-1 and CD3 or antibody fragment thereof according to claim 6, wherein the VH of the first arm specifically binding to PD-1 comprises the amino acid sequence set forth in SEQ ID NO: 4; and the VH of the second arm specifically binding to CD3 comprises the amino acid sequence set forth in SEQ ID NO: 36.

15. The bispecific antibody specifically binding to PD-1 and CD3 or antibody fragment thereof according to claim 7, wherein the VH of the first arm specifically binding to PD-1 comprises the amino acid sequence set forth in SEQ ID NO: 5; and the VH of the second arm specifically binding to CD3 comprises the amino acid sequence set forth in SEQ ID NO: 36.

16. The bispecific antibody specifically binding to PD-1 and CD3 or antibody fragment thereof according to claim 1, wherein the first arm specifically binding to PD-1 and/or the second arm specifically binding to CD3 have the VL comprising the amino acid sequence set forth in SEQ ID NO: 25.

17. A bispecific antibody specifically binding to PD-1 and CD3 or antibody fragment thereof, having a first arm specifically binding to PD-1 and a second arm specifically binding to CD3, wherein
(A) the first arm specifically binding to PD-1 has a VH comprising the amino acid sequence set forth in any one selected from SEQ ID NO: 1, SEQ ID NO: 2, SEQ ID NO: 3, SEQ ID NO: 4, and SEQ ID NO: 5, and a VL comprising the amino acid sequence set forth in SEQ ID NO: 25; and
(B) the second arm specifically binding to CD3 has a VH comprising the amino acid sequence set forth in SEQ ID NO: 36; and a VL comprising the amino acid sequence set forth in SEQ ID NO: 25.

18. A bispecific antibody specifically binding to PD-1 and CD3 or antibody fragment thereof, having a first arm specifically binding to PD-1 and a second arm specifically binding to CD3, wherein the binding to PD-1 with the first arm specifically binding to PD-1 is cross-competed (1) by a first arm specifically binding to PD-1 having a VH comprising the amino acid sequence set forth in any one selected from SEQ ID NO: 1, SEQ ID NO: 2, SEQ ID NO: 3, SEQ ID NO: 4, and SEQ ID NO: 5; and a VL comprising the amino acid sequence set forth in SEQ ID NO: 25, or (2) by a variable region of a monoclonal antibody specifically binding to PD-1 having a VH and a VL that are the same as the bispecific antibody.

19. The bispecific antibody specifically binding to PD-1 and CD3 or antibody fragment thereof according to claim 1, wherein the first arm specifically binding to PD-1 allows interaction between the PD-1 and PD-L1.

20. The bispecific antibody specifically binding to PD-1 and CD3 or antibody fragment thereof according to claim 1, which reduces cytokine production.

21. The bispecific antibody specifically binding to PD-1 and CD3 or antibody fragment thereof according to claim 20, wherein the cytokine is at least one of IL-2, IFN-γ, or TNF-α.

22. The bispecific antibody specifically binding to PD-1 and CD3 or antibody fragment thereof according to claim 1, wherein the PD-1/CD3 bispecific antibody is an IgG antibody.

23. The bispecific antibody specifically binding to PD-1 and CD3 or antibody fragment thereof according to claim 22, which is an IgG$_1$ antibody or an IgG$_4$ antibody.

24. The bispecific antibody specifically binding to PD-1 and CD3 or an antibody fragment thereof according to claim 22, which is an IgG$_1$ antibody.

25. The bispecific antibody specifically binding to PD-1 and CD3 or antibody fragment thereof according to claim 24, wherein the binding to an Fc receptor is eliminated or reduced.

26. The bispecific antibody specifically binding to PD-1 and CD3 or antibody fragment thereof according to claim 25, wherein in two heavy chain constant regions of the PD-1/CD3 bispecific IgG$_1$ antibody, leucine at position 235 according to the EU numbering system is substituted with glycine, and/or glycine at position 236 according to the EU numbering system is substituted with arginine.

27. The bispecific antibody specifically binding to PD-1 and CD3 or an antibody fragment thereof according to claim 24, wherein in a constant region of a heavy chain having a VH of the first arm specifically binding to PD-1, leucine at position 351 according to the EU numbering system is substituted with lysine, and threonine at position 366 according to the EU numbering system is substituted with lysine; and in a constant region of a heavy chain having a VH of the second arm specifically binding to CD3, leucine at position 351 according to the EU numbering system is substituted with aspartic acid, and leucine at position 368 according to the EU numbering system is substituted with glutamic acid.

28. The bispecific antibody specifically binding to PD-1 and CD3 or antibody fragment thereof according to claim 24, wherein in a constant region of a heavy chain having a VH of the first arm specifically binding to PD-1, leucine at position 351 according to the EU numbering system is substituted with aspartic acid, and leucine at position 368 is substituted with glutamic acid; and in a constant region of a heavy chain having a VH of the second arm specifically binding to CD3, leucine at position 351 according to the EU numbering system is substituted with lysine, and threonine at position 366 according to the EU numbering system is substituted with lysine.

29. The bispecific antibody specifically binding to PD-1 and CD3 or antibody fragment thereof according to claim 24, wherein in two heavy chain constant regions, lysine at position 447 according to the EU numbering system is deleted.

30. The bispecific antibody specifically binding to PD-1 and CD3 or antibody fragment thereof according to claim 23, wherein the PD-1/CD3 bispecific antibody is an IgG$_4$ antibody, and in two heavy chain constant regions, serine at position 228 according to the EU numbering system is substituted with proline.

31. The bispecific antibody specifically binding to PD-1 and CD3 or antibody fragment thereof according to claim 1, wherein a heavy chain having the VH of the first arm specifically binding to PD-1 has a heavy chain constant region comprising the amino acid sequence set forth in SEQ ID NO: 23.

32. The bispecific antibody specifically binding to PD-1 and CD3 or antibody fragment thereof according to claim 1, wherein a heavy chain having the VH of the second arm specifically binding to CD3 has a heavy chain constant region comprising the amino acid sequence set forth in SEQ ID NO: 24.

33. The bispecific antibody specifically binding to PD-1 and CD3 or antibody fragment thereof according to claim 1, wherein a light chain having the VL of the first arm specifically binding to PD-1 and/or the light chain having VL of the second arm specifically binding to CD3 have a light chain constant region comprising the amino acid sequence set forth in SEQ ID NO: 29.

34. A pharmaceutical composition comprising the bispecific antibody specifically binding to PD-1 and CD3 or antibody fragment thereof of claim 1 and a pharmaceutically acceptable carrier.

35. The bispecific antibody specifically binding to PD-1 and CD3 or antibody fragment thereof according to claim 1, wherein the bispecific antibody is a monoclonal antibody.

36. The bispecific antibody specifically binding to PD-1 and CD3 or antibody fragment thereof according to claim 1, wherein the bispecific antibody is an isolated antibody.

* * * * *

UNITED STATES PATENT AND TRADEMARK OFFICE
CERTIFICATE OF CORRECTION

| | |
|---|---|
| PATENT NO. | : 12,091,461 B2 |
| APPLICATION NO. | : 17/366878 |
| DATED | : September 17, 2024 |
| INVENTOR(S) | : Shiro Shibayama et al. |

It is certified that error appears in the above-identified patent and that said Letters Patent is hereby corrected as shown below:

On the Title Page

Page 3, Column 1, OTHER PUBLICATIONS, Line 21, delete "Bioinfomatics" and insert --Bioinformatics",-- therefor;

Page 3, Column 1, OTHER PUBLICATIONS, Line 59, delete "ofa" and insert --of a-- therefor;

In the Claims

In Claim 4, Column 72, Line 42, after "has", insert --:--;

In Claim 11, Column 73, Line 60, delete "claim 3," and insert --claim 2,-- therefor;

In Claim 12, Column 73, Line 67, delete "claim 4," and insert --claim 3,-- therefor;

In Claim 13, Column 74, Line 7, delete "claim 5," and insert --claim 4,-- therefor;

In Claim 14, Column 74, Line 14, delete "claim 6," and insert --claim 5,-- therefor;

In Claim 15, Column 74, Line 22, delete "claim 7," and insert --claim 6,-- therefor.

Signed and Sealed this
Twenty-fifth Day of February, 2025

Coke Morgan Stewart
*Acting Director of the United States Patent and Trademark Office*

```
                        SEQUENCE LISTING

<160> NUMBER OF SEQ ID NOS: 41

<210> SEQ ID NO 1
<211> LENGTH: 127
<212> TYPE: PRT
<213> ORGANISM: Homo sapiens

<400> SEQUENCE: 1

Gln Val Gln Leu Val Gln Ser Gly Ser Glu Leu Lys Gln Pro Gly Ala
1               5                   10                  15

Ser Val Lys Val Ser Cys Lys Ala Ser Gly Tyr Thr Phe Thr His Tyr
            20                  25                  30

Gly Leu His Trp Val Arg Gln Ala Pro Gly Gln Gly Leu Glu Trp Met
        35                  40                  45

Gly Trp Leu Asn Thr Asn Thr Glu Asn Pro Thr Phe Ala Gln Gly Phe
    50                  55                  60

Thr Gly Arg Phe Val Phe Ser Leu Asp Thr Ser Val Thr Thr Ala Tyr
65                  70                  75                  80

Leu Gln Ile Ser Ser Leu Lys Ala Glu Asp Thr Ala Val Tyr Tyr Cys
                85                  90                  95

Ala Arg Gly Asp Met Val Val Pro Thr Thr Ile Trp Asn Tyr Tyr His
            100                 105                 110

Phe Met Asp Val Trp Gly Asn Gly Thr Leu Val Thr Val Ser Ser
        115                 120                 125

<210> SEQ ID NO 2
<211> LENGTH: 127
<212> TYPE: PRT
<213> ORGANISM: Homo sapiens

<400> SEQUENCE: 2

Gln Val Gln Leu Val Gln Ser Gly Ser Glu Leu Lys Gln Pro Gly Val
1               5                   10                  15

Ser Val Lys Val Ser Cys Lys Ala Ser Gly Tyr Thr Phe Thr His Tyr
            20                  25                  30

Gly Leu His Trp Val Arg Gln Ala Pro Gly Gln Gly Leu Glu Trp Met
        35                  40                  45

Gly Trp Ile Asn Thr Asn Thr Gly Asn Pro Thr Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Gly Asp Leu Val Val Pro Thr Thr Ile Trp Asn Tyr Tyr His
            100                 105                 110

Tyr Met Glu Val Trp Gly Lys Gly Thr Leu Val Thr Val Ser Ser
        115                 120                 125
```

<210> SEQ ID NO 3
<211> LENGTH: 127
<212> TYPE: PRT
<213> ORGANISM: Homo sapiens

<400> SEQUENCE: 3

Gln Val Gln Leu Val Gln Ser Gly Ser Glu Leu Lys Lys Pro Gly Ala
1               5                   10                  15
Ser Val Met Val Ser Cys Lys Ala Ser Gly Tyr Thr Phe Thr His Tyr
            20                  25                  30
Ala Leu His Trp Val Arg Gln Ala Pro Gly Gln Gly Leu Glu Trp Met
        35                  40                  45
Gly Trp Leu Asn Thr Asn Thr Glu Asn Pro Thr Tyr Ala Gln Gly Phe
    50                  55                  60
Thr Gly Arg Phe Val Phe Ser Leu Asp Thr Ser Val Thr Thr Ala Tyr
65                  70                  75                  80
Leu Gln Ile Asn Ser Leu Lys Ala Glu Asp Thr Ala Val Tyr Tyr Cys
                85                  90                  95
Ala Arg Gly Asp Met Val Val Pro Thr Thr Ile Trp Asn Tyr Tyr Tyr
            100                 105                 110
Tyr Met Asp Val Trp Gly Lys Gly Thr Thr Val Thr Val Ser Ser
        115                 120                 125

<210> SEQ ID NO 4
<211> LENGTH: 127
<212> TYPE: PRT
<213> ORGANISM: Homo sapiens

<400> SEQUENCE: 4

Gln Val Gln Leu Val Gln Ser Gly Ser Glu Leu Lys Gln Pro Gly Ala
1               5                   10                  15
Ser Val Lys Val Ser Cys Lys Ala Ser Gly Tyr Thr Phe Thr His Tyr
            20                  25                  30
Ala Leu His Trp Leu Arg Gln Ala Pro Gly Gln Gly Leu Glu Trp Met
        35                  40                  45
Gly Trp Leu Asn Thr Asn Thr Glu Asn Pro Thr Phe Ala Gln Gly Phe
    50                  55                  60
Thr Gly Arg Phe Val Phe Ser Leu Asp Thr Ser Val Thr Thr Ala Tyr
65                  70                  75                  80
Leu Gln Ile Ser Ser Leu Lys Ala Glu Asp Thr Ala Val Tyr Tyr Cys
                85                  90                  95
Ala Arg Gly Asp Met Val Val Pro Thr Thr Ile Trp Asn Tyr Tyr His
            100                 105                 110
Phe Met Asp Val Trp Gly Asn Gly Thr Thr Val Thr Val Ser Ser
        115                 120                 125

<210> SEQ ID NO 5
<211> LENGTH: 127
<212> TYPE: PRT
<213> ORGANISM: Homo sapiens

<400> SEQUENCE: 5

Gln Val Gln Leu Val Gln Ser Gly Ser Glu Leu Lys Gln Pro Gly Ala
1               5                   10                  15
Ser Val Lys Val Ser Cys Lys Ala Ser Gly Tyr Thr Phe Thr His Tyr
            20                  25                  30
Ala Leu His Trp Leu Arg Gln Ala Pro Gly Gln Gly Leu Glu Trp Met

```
                35                  40                  45
Gly Trp Leu Asn Thr Asn Thr Glu Asn Pro Thr Phe Ala Gln Gly Phe
    50                  55                  60

Thr Gly Arg Phe Val Phe Ser Leu Asp Thr Ser Val Thr Thr Ala Tyr
65                  70                  75                  80

Leu Gln Ile Ser Ser Leu Lys Ala Glu Asp Thr Ala Val Tyr Tyr Cys
                85                  90                  95

Ala Arg Gly Asp Met Val Val Pro Thr Thr Ile Trp Asn Tyr Tyr His
            100                 105                 110

Phe Met Asp Val Trp Gly Gln Gly Thr Thr Val Thr Val Ser Ser
        115                 120                 125

<210> SEQ ID NO 6
<211> LENGTH: 5
<212> TYPE: PRT
<213> ORGANISM: Homo sapiens

<400> SEQUENCE: 6

His Tyr Gly Leu His
1               5

<210> SEQ ID NO 7
<211> LENGTH: 17
<212> TYPE: PRT
<213> ORGANISM: Homo sapiens

<400> SEQUENCE: 7

Trp Leu Asn Thr Asn Thr Glu Asn Pro Thr Phe Ala Gln Gly Phe Thr
1               5                   10                  15

Gly

<210> SEQ ID NO 8
<211> LENGTH: 18
<212> TYPE: PRT
<213> ORGANISM: Homo sapiens

<400> SEQUENCE: 8

Gly Asp Met Val Val Pro Thr Thr Ile Trp Asn Tyr Tyr His Phe Met
1               5                   10                  15

Asp Val

<210> SEQ ID NO 9
<211> LENGTH: 5
<212> TYPE: PRT
<213> ORGANISM: Homo sapiens

<400> SEQUENCE: 9

His Tyr Gly Leu His
1               5

<210> SEQ ID NO 10
<211> LENGTH: 17
<212> TYPE: PRT
<213> ORGANISM: Homo sapiens

<400> SEQUENCE: 10

Trp Ile Asn Thr Asn Thr Gly Asn Pro Thr Tyr Ala Gln Gly Phe Thr
1               5                   10                  15

Gly
```

```
<210> SEQ ID NO 11
<211> LENGTH: 18
<212> TYPE: PRT
<213> ORGANISM: Homo sapiens

<400> SEQUENCE: 11

Gly Asp Leu Val Val Pro Thr Thr Ile Trp Asn Tyr Tyr His Tyr Met
1               5                   10                  15
Glu Val

<210> SEQ ID NO 12
<211> LENGTH: 5
<212> TYPE: PRT
<213> ORGANISM: Homo sapiens

<400> SEQUENCE: 12

His Tyr Ala Leu His
1               5

<210> SEQ ID NO 13
<211> LENGTH: 17
<212> TYPE: PRT
<213> ORGANISM: Homo sapiens

<400> SEQUENCE: 13

Trp Leu Asn Thr Asn Thr Glu Asn Pro Thr Tyr Ala Gln Gly Phe Thr
1               5                   10                  15
Gly

<210> SEQ ID NO 14
<211> LENGTH: 18
<212> TYPE: PRT
<213> ORGANISM: Homo sapiens

<400> SEQUENCE: 14

Gly Asp Met Val Val Pro Thr Thr Ile Trp Asn Tyr Tyr Tyr Tyr Met
1               5                   10                  15
Asp Val

<210> SEQ ID NO 15
<211> LENGTH: 5
<212> TYPE: PRT
<213> ORGANISM: Homo sapiens

<400> SEQUENCE: 15

His Tyr Ala Leu His
1               5

<210> SEQ ID NO 16
<211> LENGTH: 17
<212> TYPE: PRT
<213> ORGANISM: Homo sapiens

<400> SEQUENCE: 16

Trp Leu Asn Thr Asn Thr Glu Asn Pro Thr Phe Ala Gln Gly Phe Thr
1               5                   10                  15
Gly

<210> SEQ ID NO 17
<211> LENGTH: 18
<212> TYPE: PRT
<213> ORGANISM: Homo sapiens
```

-continued

```
<400> SEQUENCE: 17

Gly Asp Met Val Val Pro Thr Thr Ile Trp Asn Tyr Tyr His Phe Met
1               5                   10                  15

Asp Val

<210> SEQ ID NO 18
<211> LENGTH: 5
<212> TYPE: PRT
<213> ORGANISM: Homo sapiens

<400> SEQUENCE: 18

His Tyr Ala Leu His
1               5

<210> SEQ ID NO 19
<211> LENGTH: 17
<212> TYPE: PRT
<213> ORGANISM: Homo sapiens

<400> SEQUENCE: 19

Trp Leu Asn Thr Asn Thr Glu Asn Pro Thr Phe Ala Gln Gly Phe Thr
1               5                   10                  15

Gly

<210> SEQ ID NO 20
<211> LENGTH: 18
<212> TYPE: PRT
<213> ORGANISM: Homo sapiens

<400> SEQUENCE: 20

Gly Asp Met Val Val Pro Thr Thr Ile Trp Asn Tyr Tyr His Phe Met
1               5                   10                  15

Asp Val

<210> SEQ ID NO 21
<211> LENGTH: 98
<212> TYPE: PRT
<213> ORGANISM: Homo sapiens

<400> SEQUENCE: 21

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Ser Tyr
                20                  25                  30

Ala Met Asn Trp Val Arg Gln Ala Pro Gly Gln Gly Leu Glu Trp Met
            35                  40                  45

Gly Trp Ile Asn Thr Asn Thr Gly Asn Pro Thr Tyr Ala Gln Gly Phe
        50                  55                  60

Thr Gly Arg Phe Val Phe Ser Leu Asp Thr Ser Val Ser Thr Ala Tyr
65                  70                  75                  80

Leu Gln Ile Cys Ser Leu Lys Ala Glu Asp Thr Ala Val Tyr Tyr Cys
                85                  90                  95

Ala Arg

<210> SEQ ID NO 22
<211> LENGTH: 98
<212> TYPE: PRT
<213> ORGANISM: Homo sapiens

<400> SEQUENCE: 22
```

Gln Val Gln Leu Val Glu Ser Gly Gly Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Trp Tyr Asp Gly Ser Asn Lys Tyr Tyr Ala Asp Ser Val
50                      55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 23
<211> LENGTH: 329
<212> TYPE: PRT
<213> ORGANISM: Homo sapiens

<400> SEQUENCE: 23

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Gly Arg Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Asp Pro Pro Ser Arg Glu Glu
225                 230                 235                 240

Met Thr Lys Asn Gln Val Ser Leu Thr Cys Glu Val Lys Gly Phe Tyr
                245                 250                 255

Pro Ser Asp Ile Ala Val Glu Trp Glu Ser Asn Gly Gln Pro Glu Asn
            260                 265                 270

```
Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly
            325

<210> SEQ ID NO 24
<211> LENGTH: 329
<212> TYPE: PRT
<213> ORGANISM: Homo sapiens

<400> SEQUENCE: 24

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Gly Arg Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Lys Pro Pro Ser Arg Glu Glu
225                 230                 235                 240

Met Thr Lys Asn Gln Val Ser Leu Lys Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
```

```
                         305                 310                 315                 320
Gln Lys Ser Leu Ser Leu Ser Pro Gly
                    325

<210> SEQ ID NO 25
<211> LENGTH: 107
<212> TYPE: PRT
<213> ORGANISM: Homo sapiens

<400> SEQUENCE: 25

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Thr Phe Gly Gln Gly Thr Lys Val Glu Ile Lys
            100                 105

<210> SEQ ID NO 26
<211> LENGTH: 11
<212> TYPE: PRT
<213> ORGANISM: Homo sapiens

<400> SEQUENCE: 26

Arg Ala Ser Gln Ser Ile Ser Ser Tyr Leu Asn
1               5                   10

<210> SEQ ID NO 27
<211> LENGTH: 7
<212> TYPE: PRT
<213> ORGANISM: Homo sapiens

<400> SEQUENCE: 27

Ala Ala Ser Ser Leu Gln Ser
1               5

<210> SEQ ID NO 28
<211> LENGTH: 9
<212> TYPE: PRT
<213> ORGANISM: Homo sapiens

<400> SEQUENCE: 28

Gln Gln Ser Tyr Ser Thr Pro Pro Thr
1               5

<210> SEQ ID NO 29
<211> LENGTH: 107
<212> TYPE: PRT
<213> ORGANISM: Homo sapiens

<400> SEQUENCE: 29

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
```

```
                   20                  25                  30
Tyr Pro Arg Glu Ala Lys Val Gln Trp Lys Val Asp Asn Ala Leu Gln
             35                  40                  45

Ser Gly Asn Ser Gln Glu Ser Val Thr Glu Gln Asp Ser Lys Asp Ser
         50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
            100                 105

<210> SEQ ID NO 30
<211> LENGTH: 381
<212> TYPE: DNA
<213> ORGANISM: Homo sapiens
<220> FEATURE:
<221> NAME/KEY: CDS
<222> LOCATION: (1)..(381)

<400> SEQUENCE: 30 cag gtg cag ctg gtg caa tct ggg tct gag ttg aag cag cct ggg gcc    48
Gln Val Gln Leu Val Gln Ser Gly Ser Glu Leu Lys Gln Pro Gly Ala
1               5                  10                  15 tca gtg aag gtt tcc tgt aag gct tct gga tac acc ttc act cac tat    96
Ser Val Lys Val Ser Cys Lys Ala Ser Gly Tyr Thr Phe Thr His Tyr
             20                  25                  30 ggt ttg cat tgg gtg cga cag gcc cct gga caa ggg ctt gag tgg atg   144
Gly Leu His Trp Val Arg Gln Ala Pro Gly Gln Gly Leu Glu Trp Met
         35                  40                  45 gga tgg ctc aac acc aac act gag aac cca acg ttt gcc cag ggc ttc   192
Gly Trp Leu Asn Thr Asn Thr Glu Asn Pro Thr Phe Ala Gln Gly Phe
     50                  55                  60 aca gga cgg ttt gtc ttc tcc ttg gac acc tct gtc acc acg gca tat   240
Thr Gly Arg Phe Val Phe Ser Leu Asp Thr Ser Val Thr Thr Ala Tyr
65                  70                  75                  80 ctg cag atc agc agc ctg aag gct gag gac act gcc gta tat tac tgt   288
Leu Gln Ile Ser Ser Leu Lys Ala Glu Asp Thr Ala Val Tyr Tyr Cys
                 85                  90                  95 gcg aga ggg gat atg gta gta ccg act act ata tgg aac tac tac cac   336
Ala Arg Gly Asp Met Val Val Pro Thr Thr Ile Trp Asn Tyr Tyr His
            100                 105                 110 ttc atg gac gtc tgg ggc aac ggc acc ctg gtc acc gtc tcg agt       381
Phe Met Asp Val Trp Gly Asn Gly Thr Leu Val Thr Val Ser Ser
        115                 120                 125

<210> SEQ ID NO 31
<211> LENGTH: 381
<212> TYPE: DNA
<213> ORGANISM: Homo sapiens
<220> FEATURE:
<221> NAME/KEY: CDS
<222> LOCATION: (1)..(381)

<400> SEQUENCE: 31 cag gtg cag ctg gtg caa tct ggg tct gag ttg aag cag cct ggg gtc    48
Gln Val Gln Leu Val Gln Ser Gly Ser Glu Leu Lys Gln Pro Gly Val
1               5                  10                  15 tca gtg aag gtt tcc tgc aag gct tct gga tac acc ttc act cac tat    96
Ser Val Lys Val Ser Cys Lys Ala Ser Gly Tyr Thr Phe Thr His Tyr
             20                  25                  30
```

| | | | | | | | | | | | | | | | | |
|---|---|---|---|---|---|---|---|---|---|---|---|---|---|---|---|---|
| ggt | tta | cat | tgg | gtg | cga | cag | gcc | cct | gga | caa | ggg | ctt | gag | tgg | atg | 144 |
| Gly | Leu | His | Trp | Val | Arg | Gln | Ala | Pro | Gly | Gln | Gly | Leu | Glu | Trp | Met | |
| | | 35 | | | | | 40 | | | | | 45 | | | | |
| gga | tgg | atc | aac | acc | aac | act | ggg | aac | cca | acg | tat | gcc | cag | ggc | ttc | 192 |
| Gly | Trp | Ile | Asn | Thr | Asn | Thr | Gly | Asn | Pro | Thr | Tyr | Ala | Gln | Gly | Phe | |
| 50 | | | | | 55 | | | | | 60 | | | | | | |
| aca | gga | cgg | ttt | gtc | ttc | tcc | ttg | gac | acc | tct | gtc | agc | acg | gca | tat | 240 |
| Thr | Gly | Arg | Phe | Val | Phe | Ser | Leu | Asp | Thr | Ser | Val | Ser | Thr | Ala | Tyr | |
| 65 | | | | 70 | | | | | 75 | | | | | 80 | | |
| ctg | cag | atc | agc | agc | cta | aag | gct | gaa | gac | act | gcc | gtg | tat | tac | tgt | 288 |
| Leu | Gln | Ile | Ser | Ser | Leu | Lys | Ala | Glu | Asp | Thr | Ala | Val | Tyr | Tyr | Cys | |
| | | | | 85 | | | | | 90 | | | | | 95 | | |
| gcg | aga | ggg | gat | tta | gta | gta | cca | act | act | ata | tgg | aac | tac | tac | cac | 336 |
| Ala | Arg | Gly | Asp | Leu | Val | Val | Pro | Thr | Thr | Ile | Trp | Asn | Tyr | Tyr | His | |
| | | | 100 | | | | | 105 | | | | | 110 | | | |
| tac | atg | gag | gtc | tgg | ggc | aaa | ggc | acc | ctg | gtc | acc | gtc | tcg | agt | | 381 |
| Tyr | Met | Glu | Val | Trp | Gly | Lys | Gly | Thr | Leu | Val | Thr | Val | Ser | Ser | | |
| | | | 115 | | | | 120 | | | | | 125 | | | | |

<210> SEQ ID NO 32
<211> LENGTH: 381
<212> TYPE: DNA
<213> ORGANISM: Homo sapiens
<220> FEATURE:
<221> NAME/KEY: CDS
<222> LOCATION: (1)..(381)

<400> SEQUENCE: 32

| | | | | | | | | | | | | | | | | |
|---|---|---|---|---|---|---|---|---|---|---|---|---|---|---|---|---|
| cag | gtg | cag | ctg | gtg | caa | tct | ggg | tct | gag | ttg | aag | aag | cct | ggg | gcc | 48 |
| Gln | Val | Gln | Leu | Val | Gln | Ser | Gly | Ser | Glu | Leu | Lys | Lys | Pro | Gly | Ala | |
| 1 | | | | 5 | | | | | 10 | | | | | 15 | | |
| tca | gtg | atg | gtt | tcc | tgc | aag | gct | tct | gga | tac | acc | ttc | act | cac | tat | 96 |
| Ser | Val | Met | Val | Ser | Cys | Lys | Ala | Ser | Gly | Tyr | Thr | Phe | Thr | His | Tyr | |
| | | 20 | | | | | 25 | | | | | 30 | | | | |
| gct | ttg | cat | tgg | gtg | cgc | cag | gcc | cct | gga | caa | ggg | ctt | gag | tgg | atg | 144 |
| Ala | Leu | His | Trp | Val | Arg | Gln | Ala | Pro | Gly | Gln | Gly | Leu | Glu | Trp | Met | |
| | | 35 | | | | | 40 | | | | | 45 | | | | |
| gga | tgg | ctc | aat | acc | aac | act | gag | aat | cca | acg | tat | gcc | cag | ggc | ttc | 192 |
| Gly | Trp | Leu | Asn | Thr | Asn | Thr | Glu | Asn | Pro | Thr | Tyr | Ala | Gln | Gly | Phe | |
| 50 | | | | | 55 | | | | | 60 | | | | | | |
| aca | gga | cgg | ttt | gtc | ttc | tcc | ttg | gac | acc | tct | gtc | acc | acg | gca | tat | 240 |
| Thr | Gly | Arg | Phe | Val | Phe | Ser | Leu | Asp | Thr | Ser | Val | Thr | Thr | Ala | Tyr | |
| 65 | | | | 70 | | | | | 75 | | | | | 80 | | |
| ctg | cag | atc | aac | agc | cta | aag | gct | gag | gac | act | gcc | gtg | tat | tac | tgt | 288 |
| Leu | Gln | Ile | Asn | Ser | Leu | Lys | Ala | Glu | Asp | Thr | Ala | Val | Tyr | Tyr | Cys | |
| | | | | 85 | | | | | 90 | | | | | 95 | | |
| gcg | aga | ggg | gat | atg | gta | gta | cca | act | act | ata | tgg | aac | tac | tac | tac | 336 |
| Ala | Arg | Gly | Asp | Met | Val | Val | Pro | Thr | Thr | Ile | Trp | Asn | Tyr | Tyr | Tyr | |
| | | | 100 | | | | | 105 | | | | | 110 | | | |
| tac | atg | gac | gtc | tgg | ggc | aaa | ggg | acc | acg | gtc | acc | gtc | tcg | agt | | 381 |
| Tyr | Met | Asp | Val | Trp | Gly | Lys | Gly | Thr | Thr | Val | Thr | Val | Ser | Ser | | |
| | | | 115 | | | | 120 | | | | | 125 | | | | |

<210> SEQ ID NO 33
<211> LENGTH: 381
<212> TYPE: DNA
<213> ORGANISM: Homo sapiens
<220> FEATURE:
<221> NAME/KEY: CDS
<222> LOCATION: (1)..(381)

<400> SEQUENCE: 33

| | | | | | | | | | | | | | | | | |
|---|---|---|---|---|---|---|---|---|---|---|---|---|---|---|---|---|
| cag | gtg | cag | ctg | gtg | caa | tct | ggg | tct | gag | ttg | aag | cag | cct | ggg | gcc | 48 |

```
                Gln Val Gln Leu Val Gln Ser Gly Ser Glu Leu Lys Gln Pro Gly Ala
                1               5                   10                  15 tca gtg aag gtt tcc tgt aag gct tct gga tac acc ttc act cac tat        96
Ser Val Lys Val Ser Cys Lys Ala Ser Gly Tyr Thr Phe Thr His Tyr
                20                  25                  30 gct ttg cat tgg ttg cga cag gcc cct gga caa ggg ctt gag tgg atg        144
Ala Leu His Trp Leu Arg Gln Ala Pro Gly Gln Gly Leu Glu Trp Met
            35                  40                  45 gga tgg ctc aac acc aac act gag aac cca acg ttt gcc cag ggc ttc        192
Gly Trp Leu Asn Thr Asn Thr Glu Asn Pro Thr Phe Ala Gln Gly Phe
    50                  55                  60 aca gga cgt ttt gtc ttc tct ttg gac acc tct gtc acc acg gca tat        240
Thr Gly Arg Phe Val Phe Ser Leu Asp Thr Ser Val Thr Thr Ala Tyr
65                  70                  75                  80 ctg cag atc agc agc ctg aag gct gag gac act gcc gta tat tac tgt        288
Leu Gln Ile Ser Ser Leu Lys Ala Glu Asp Thr Ala Val Tyr Tyr Cys
                85                  90                  95 gcg aga ggg gat atg gta gta ccg act act ata tgg aac tac tac cac        336
Ala Arg Gly Asp Met Val Val Pro Thr Thr Ile Trp Asn Tyr Tyr His
            100                 105                 110 ttc atg gac gtc tgg ggc aac ggg acc acg gtc acc gtc tcg agt            381
Phe Met Asp Val Trp Gly Asn Gly Thr Thr Val Thr Val Ser Ser
    115                 120                 125

<210> SEQ ID NO 34
<211> LENGTH: 381
<212> TYPE: DNA
<213> ORGANISM: Homo sapiens
<220> FEATURE:
<221> NAME/KEY: CDS
<222> LOCATION: (1)..(381)

<400> SEQUENCE: 34 cag gtg cag ctg gtg caa tct ggg tct gag ttg aag cag cct ggg gcc        48
Gln Val Gln Leu Val Gln Ser Gly Ser Glu Leu Lys Gln Pro Gly Ala
1               5                   10                  15 tca gtg aag gtt tcc tgt aag gct tct gga tac acc ttc act cac tat        96
Ser Val Lys Val Ser Cys Lys Ala Ser Gly Tyr Thr Phe Thr His Tyr
                20                  25                  30 gct ttg cat tgg ttg cga cag gcc cct gga caa ggg ctt gag tgg atg        144
Ala Leu His Trp Leu Arg Gln Ala Pro Gly Gln Gly Leu Glu Trp Met
            35                  40                  45 gga tgg ctc aac acc aac act gag aac cca acg ttt gcc cag ggc ttc        192
Gly Trp Leu Asn Thr Asn Thr Glu Asn Pro Thr Phe Ala Gln Gly Phe
    50                  55                  60 aca gga cgt ttt gtc ttc tct ttg gac acc tct gtc acc acg gca tat        240
Thr Gly Arg Phe Val Phe Ser Leu Asp Thr Ser Val Thr Thr Ala Tyr
65                  70                  75                  80 ctg cag atc agc agc ctg aag gct gag gac act gcc gta tat tac tgt        288
Leu Gln Ile Ser Ser Leu Lys Ala Glu Asp Thr Ala Val Tyr Tyr Cys
                85                  90                  95 gcg aga ggg gat atg gta gta ccg act act ata tgg aac tac tac cac        336
Ala Arg Gly Asp Met Val Val Pro Thr Thr Ile Trp Asn Tyr Tyr His
            100                 105                 110 ttc atg gac gtc tgg ggc cag ggg acc acg gtc acc gtc tcg agt            381
Phe Met Asp Val Trp Gly Gln Gly Thr Thr Val Thr Val Ser Ser
    115                 120                 125

<210> SEQ ID NO 35
<211> LENGTH: 321
<212> TYPE: DNA
<213> ORGANISM: Homo sapiens
```

```
<220> FEATURE:
<221> NAME/KEY: CDS
<222> LOCATION: (1)..(321)

<400> SEQUENCE: 35 gac atc cag atg acc cag tct cca tcc tcc ctg tct gca tct gta gga      48
Asp Ile Gln Met Thr Gln Ser Pro Ser Ser Leu Ser Ala Ser Val Gly
1               5                   10                  15 gac aga gtc acc atc act tgc cgg gca agt cag agc att agc agc tac      96
Asp Arg Val Thr Ile Thr Cys Arg Ala Ser Gln Ser Ile Ser Ser Tyr
            20                  25                  30 tta aat tgg tat cag cag aaa cca ggg aaa gcc cct aag ctc ctg atc     144
Leu Asn Trp Tyr Gln Gln Lys Pro Gly Lys Ala Pro Lys Leu Leu Ile
        35                  40                  45 tat gct gca tcc agt ttg caa agt ggg gtc cca tca agg ttc agt ggc     192
Tyr Ala Ala Ser Ser Leu Gln Ser Gly Val Pro Ser Arg Phe Ser Gly
50                  55                  60 agt gga tct ggg aca gat ttc act ctc acc atc agc agt ctg caa cct     240
Ser Gly Ser Gly Thr Asp Phe Thr Leu Thr Ile Ser Ser Leu Gln Pro
65                  70                  75                  80 gaa gat ttt gca act tac tac tgt caa cag agt tac agt acc cct cca     288
Glu Asp Phe Ala Thr Tyr Tyr Cys Gln Gln Ser Tyr Ser Thr Pro Pro
                85                  90                  95 acg ttc ggc caa ggg acc aag gtg gag atc aaa                         321
Thr Phe Gly Gln Gly Thr Lys Val Glu Ile Lys
            100                 105

<210> SEQ ID NO 36
<211> LENGTH: 118
<212> TYPE: PRT
<213> ORGANISM: Homo sapiens

<400> SEQUENCE: 36

Gln Val Gln Leu Val Gln Ser Gly Gly Gly Val Val Gln Pro Gly Arg
1               5                   10                  15

Ser Leu Arg Leu Ser Cys Val Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Gln Ile Trp Tyr Asn Ala Arg Lys Gln Glu Tyr Ser Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Gly Thr Gly Tyr Asn Trp Phe Asp Pro Trp Gly Gln Gly Thr
            100                 105                 110

Leu Val Thr Val Ser Ser
        115

<210> SEQ ID NO 37
<211> LENGTH: 5
<212> TYPE: PRT
<213> ORGANISM: Homo sapiens

<400> SEQUENCE: 37

Ser Tyr Gly Met His
1               5

<210> SEQ ID NO 38
```

-continued

```
<211> LENGTH: 17
<212> TYPE: PRT
<213> ORGANISM: Homo sapiens

<400> SEQUENCE: 38

Gln Ile Trp Tyr Asn Ala Arg Lys Gln Glu Tyr Ser Asp Ser Val Lys
1               5                   10                  15
Gly

<210> SEQ ID NO 39
<211> LENGTH: 9
<212> TYPE: PRT
<213> ORGANISM: Homo sapiens

<400> SEQUENCE: 39

Gly Thr Gly Tyr Asn Trp Phe Asp Pro
1               5

<210> SEQ ID NO 40
<211> LENGTH: 354
<212> TYPE: DNA
<213> ORGANISM: Homo sapiens
<220> FEATURE:
<221> NAME/KEY: CDS
<222> LOCATION: (1)..(354)

<400> SEQUENCE: 40 cag gtg cag ctg gtg cag tct ggc ggc gga gtg gtg cag ccc ggc aga      48
Gln Val Gln Leu Val Gln Ser Gly Gly Gly Val Val Gln Pro Gly Arg
1               5                   10                  15 agc ctg aga ctg agc tgc gtg gcc agc ggc ttc acc ttc agc agc tac      96
Ser Leu Arg Leu Ser Cys Val Ala Ser Gly Phe Thr Phe Ser Ser Tyr
                20                  25                  30 ggc atg cac tgg gtc cgc cag gcc cct ggc aag gga ctg gaa tgg gtg     144
Gly Met His Trp Val Arg Gln Ala Pro Gly Lys Gly Leu Glu Trp Val
            35                  40                  45 gcc cag atc tgg tac aac gcc cgg aag cag gaa tac tct gac agc gtg     192
Ala Gln Ile Trp Tyr Asn Ala Arg Lys Gln Glu Tyr Ser Asp Ser Val
        50                  55                  60 aag ggc cgg ttc acc atc agc cgg gac aac agc aag aac acc ctg tac     240
Lys Gly Arg Phe Thr Ile Ser Arg Asp Asn Ser Lys Asn Thr Leu Tyr
65                  70                  75                  80 ctg cag atg aac agc ctc cgg gcc gag gac acc gcc gtg tac tac tgt     288
Leu Gln Met Asn Ser Leu Arg Ala Glu Asp Thr Ala Val Tyr Tyr Cys
                85                  90                  95 acc cgg ggc acc ggc tac aat tgg ttc gac cct tgg ggc cag ggc acc     336
Thr Arg Gly Thr Gly Tyr Asn Trp Phe Asp Pro Trp Gly Gln Gly Thr
            100                 105                 110 ctg gtc acc gtc tcc agt                                              354
Leu Val Thr Val Ser Ser
        115

<210> SEQ ID NO 41
<211> LENGTH: 11
<212> TYPE: PRT
<213> ORGANISM: Homo sapiens

<400> SEQUENCE: 41

Trp Gly Lys Gly Thr Thr Val Thr Val Ser Ser
1               5                   10
```